(12) United States Patent
Jaschinski et al.

(10) Patent No.: US 9,926,563 B2
(45) Date of Patent: Mar. 27, 2018

(54) MODIFIED TGF-BETA OLIGONUCLEOTIDES

(71) Applicant: ISARNA Therapeutics GmbH, München (DE)

(72) Inventors: Frank Jaschinski, Obertraubling (DE); Michel Janicot, Brussels (BE); Eugen Uhlmann, Glashütten (DE)

(73) Assignee: ISARNA THERAPEUTICS GMBH, München (DE)

( * ) Notice: Subject to any disclaimer, the term of this patent is extended or adjusted under 35 U.S.C. 154(b) by 0 days.

(21) Appl. No.: 14/780,043

(22) PCT Filed: Mar. 27, 2014

(86) PCT No.: PCT/EP2014/056221
§ 371 (c)(1),
(2) Date: Sep. 25, 2015

(87) PCT Pub. No.: WO2014/154835
PCT Pub. Date: Oct. 2, 2014

(65) Prior Publication Data
US 2016/0076037 A1     Mar. 17, 2016

(30) Foreign Application Priority Data

Mar. 27, 2013 (EP) .................................. 13161474
Jun. 20, 2013 (EP) .................................. 13173078
Dec. 30, 2013 (EP) .................................. 13199826

(51) Int. Cl.
C12N 15/113 (2010.01)

(52) U.S. Cl.
CPC ...... *C12N 15/1136* (2013.01); *C12N 2310/11* (2013.01); *C12N 2310/3231* (2013.01); *C12N 2310/341* (2013.01); *C12N 2310/351* (2013.01)

(58) Field of Classification Search
None
See application file for complete search history.

(56) References Cited

U.S. PATENT DOCUMENTS

| | | | |
|---|---|---|---|
| 2004/0006030 A1* | 1/2004 | Monia | C07H 21/04 514/44 A |
| 2011/0136893 A1 | 6/2011 | Schlingensiepen | |

FOREIGN PATENT DOCUMENTS

| | | |
|---|---|---|
| EP | 1008649 A2 | 6/2000 |
| EP | 2399611 A2 | 12/2011 |
| EP | 2453017 A1 | 5/2012 |
| WO | 1994025588 A2 | 11/1994 |
| WO | 2004005552 A1 | 1/2004 |
| WO | 2005084712 A2 | 9/2005 |
| WO | 2011154542 A1 | 12/2011 |

OTHER PUBLICATIONS

Stanton, Robert, et al., "Chemical Modification Study of Antisense Gapmers," Nucleic Acid Therapeutics, Oct. 2012, pp. 344-359, vol. 22, No. 5.
Gordon, Kelly J., et al., "Role of transforming growth factor-beta superfamily signaling pathways in human disease," Biochimica ET Biophysica Acta, Molecular Basis of Disease, Feb. 11, 2008, pp. 197-228, vol. 1782, No. 4.
Takagi-Sato, Miho, et al., "Design of ENA® gapmers as fine-tuning antisense oligonucleotides with sequence-specific inhibitory activity on mouse PADI4 mRNA expression," Nucleic Acids Symposium Series, 2006, pp. 319-320, No. 50.
Prendes, Mark A, et al., "The role of transforming growth factor beta in glaucoma and the therapeutic implications," British Journal of Ophthalmology, Jan. 15, 2013, pp. 680-686, vol. 97, No. 6.

* cited by examiner

*Primary Examiner* — J. E. Angell
(74) *Attorney, Agent, or Firm* — Gianna Julian-Arnold; Saul Ewing Arnstein & Lehr LLP

(57) ABSTRACT

The invention refers to an oligonucleotide consisting of 10 to 20 nucleotides of selected regions of the TGF-beta1, TGF-beta2 or TGF-beta3 nucleic acid sequence, which comprises modified nucleotides such as LNA, ENA, poly-alkylene oxide-, 2'-fluoro, 2'-O-methoxy and/or 2'-O-methyl modified nucleotides. The selected regions are preferably the region of nucleic acid no. 1380 to 1510, no. 1660 to 1680, no. 2390 to 2410, or no. 2740 to 2810 of the TGF-beta2 nucleic acid sequence of SEQ ID NO. 1, specific regions of the TGF-beta1 nucleic acid sequence of SEQ ID NO. 149, or specific regions of the TGF-beta3 nucleic acid sequence of SEQ ID No. 267. The invention further relates to pharmaceutical compositions comprising such oligonucleotide, wherein the composition or the oligonucleotide is used in the prevention and/or treatment of a malignant and/or benign tumor, an immunologic disease, fibrosis, glaucoma, etc.

10 Claims, 44 Drawing Sheets

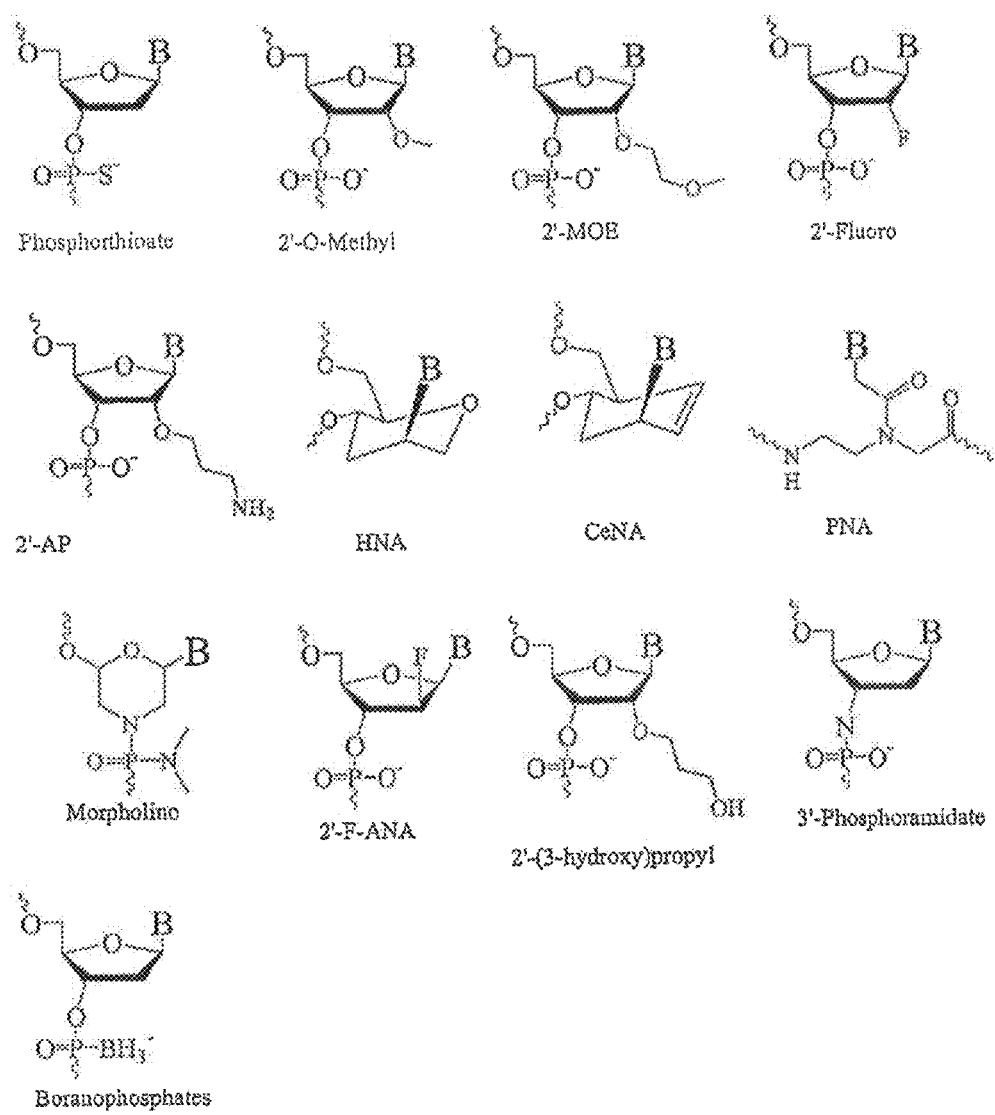
Fig. 1: Nucleotide modifications

Fig. 2a: Nucleic acid sequence of human TGF-beta 2 (SEQ ID NO. 1)

```
   1 gtgatgttat ctgctggcag cagaaggttc gctccgagcg gagctccaga agctcctgac
  61 aagagaaaga cagattgaga tagagataga aagagaaaga gagaaagaga cagcagagcg
 121 agagcgcaag tgaaagaggc aggggagggg gatggagaat attagcctga cggtctaggg
 181 agtcatccag gaacaaactg aggggctgcc cggctgcaga caggaggaga cagagaggat
 241 ctattttagg gtggcaagtg cctacctacc ctaagcgagc aattccacgt tggggagaag
 301 ccagcagagg ttgggaaagg gtgggagtcc aagggagccc ctgcgcaacc ccctcaggaa
 361 taaaactccc cagccagggt gtcgcaaggg ctgccgttgt gatccgcagg gggtgaacgc
 421 aaccgcgacg gctgatcgtc tgtggctggg ttggcgtttg gagcaagaga aggaggagca
 481 ggagaaggag ggagctggag gctggaagcg tttgcaagcg gcggcggcag caacgtggag
 541 taaccaagcg ggtcagcgcg cgcccgccag ggtgtaggcc acggagcgca gctcccagag
 601 caggatccgc gccgcctcag cagcctctgc ggccctgcg gcacccgacc gagtaccgag
 661 cgcctgcga agcgcaccct cctcccgcg gtgcgctggg ctcgcccca gcgcgcgcac
 721 acgcacacac acacacacac acacacacg acgcacacac gtgtgcgctt ctctgctccg
 781 gagctgctgc tgctcctgct ctcagcgccg cagtggaagg caggaccgaa ccgctccttc
 841 tttaaatata taaatttcag cccaggtcag cctcggcggc ccccctcacc gcgctcccgg
 901 cgccctccc gtcagttcgc cagctgccag ccccgggacc ttttcatctc ttcccttttg
 961 gccggaggag ccgagttcag atccgccact ccgcacccga gactgacaca ctgaactcca
1021 cttcctcctc ttaaatttat ttctacttaa tagccactcg tctctttttt tccccatctc
1081 attgctccaa gaatttttt cttcttactc gccaaagtca gggttccctc tgcccgtccc
1141 gtattaatat ttccactttt ggaactactg gccttttctt tttaaaggaa ttcaagcagg
1201 atacgttttt ctgttgggca ttgactagat tgtttgcaaa agtttcgcat caaaaacaac
1261 aacaacaaaa aaccaaacaa ctctccttga tctatacttt gagaattgtt gatttctttt
1321 ttttattctg acttttaaaa acaacttttt tttccacttt tttaaaaaat gcactactgt
1381 gtgctgagcg cttttctgat cctgcatctg gtcacggtcg cgctcagcct gtctacctgc
1441 agcacactcg atatggacca gttcatgcgc aagaggatcg aggcgatccg cgggcagatc
1501 ctgagcaagc tgaagctcac cagtccccca gaagactatc ctgagcccga ggaagtcccc
1561 ccggaggtga tttccatcta caacagcacc agggacttgc tccaggagaa ggcgagccgg
1621 agggcggccg cctgcgagcg cgagaggagc gacgaagagt actacgccaa ggaggtttac
1681 aaaatagaca tgccgccctt cttcccctcc gaaaatgcca tcccgccac tttctacaga
1741 ccctacttca gaattgttcg atttgacgtc tcagcaatgg agaagaatgc ttccaatttg
1801 gtgaaagcag agttcagagt ctttcgtttg cagaacccaa agccagagt gcctgaacaa
1861 cggattgagc tatatcagat tctcaagtcc aaagatttaa catctccaac ccagcgctac
1921 atcgacagca aagtgtgaa aacaagagca gaaggcgaat ggctctcctt cgatgtaact
1981 gatgctgttc atgaatgct tcaccataaa gacaggaacc tgggatttaa aataagctta
2041 cactgtcct gctgcacttt tgtaccatct aataattaca tcatcccaaa taaaagtgaa
2101 gaactagaag caagatttgc aggtattgat ggcacctcca catataccag tggtgatcag
2161 aaaactataa agtccactag gaaaaaaaac agtgggaaga cccacatct cctgctaatg
2221 ttattgcccc cctacagact tgagtcacaa cagaccaacc ggcggaagaa gcgtgctttg
2281 gatgcggcct attgctttag aaatgtgcag gataattgct gcctacgtcc acttttacatt
2341 gatttcaaga gggatctagg gtggaaatgg atacacgaac ccaaagggta caatgccaac
2401 ttctgtgctg gagcatgccc gtatttatgg agttcagaca ctcagcacag cagggtcctg
2461 agcttatata ataccataaa tccagaagca tctgcttctc cttgctgcgt gtccaagat
2521 ttagaacctc taaccattct ctactacatt ggcaaaacac ccaagattga acagctttct
2581 aatatgattg taaagtcttg caaatgcagc taaaattctt ggaaaagtgg caagaccaaa
2641 atgacaatga tgatgataat gatgatgacg acgacaacga tgatgcttgt aacaagaaaa
2701 cataagagag ccttggttca tcagtgttaa aaattttg aaaggcggt actagttcag
2761 acactttgga agttgtgtt ctgtttgtta aaactgcat ctgacacaaa aaagttgaa
2821 ggccttattc tacatttcac ctactttgta agtgagagag acaagaagca aattttttt
2881 aaagaaaaaa ataaacactg gaagaattta ttagtgttaa ttatgtgaac aacgacaaca
2941 acaacaacaa caacaaacag gaaaatccca ttaagtggag ttgctgtacg taccgttcct
3001 atcccgcgcc tcacttgatt tttctgtatt gctatgcaat aggcacccct cccattctta
3061 ctcttagagt taacagtgag ttatttattg tgtgttacta tataatgaac gtttcattgc
3121 ccttggaaaa taaacaggt gtataaagtg gagaccaaat actttgccag aaactcatgg
3181 atggcttaag gaacttgaac tcaaacgagc cagaaaaaaa gaggtcatat taatgggatg
3241 aaaaccccaag tgagttatta tatgaccgag aaagtctgca ttaagataaa gaccctgaaa
3301 acacatgtta tgtatcagct gcctaaggaa gcttcttgta aggtccaaaa actaaaaaga
```

Fig. 2b

```
3361 ctgttaataa aagaaacttt cagtcagaat aagtctgtaa gttttttttt ttctttttaa
3421 ttgtaaatgg ttctttgtca gtttagtaaa ccagtgaaat gttgaaatgt tttgacatgt
3481 actggtcaaa cttcagacct taaaatattg ctgtatagct atgctatagg ttttttcctt
3541 tgttttggta tatgtaacca tacctatatt attaaaatag atggatatag aagccagcat
3601 aattgaaaac acatctgcag atctcttttg caaactatta aatcaaaaca ttaactactt
3661 tatgtgtaat gtgtaaattt ttaccatatt ttttatattc tgtaataatg tcaactatga
3721 tttagattga cttaaatttg ggctctttt aatgatcact cacaaatgta tgtttctttt
3781 agctggccag tacttttgag taaagcccct atagtttgac ttgcactaca aatgcatttt
3841 ttttttaata acatttgccc tacttgtgct ttgtgtttct tcattatta tgacataagc
3901 tacctgggtc cacttgtctt ttctttttt tgtttcacag aaaagatggg ttcgagttca
3961 gtggtcttca tcttccaagc atcattacta accaagtcag acgttaacaa attttatgt
4021 taggaaaagg aggaatgtta tagatacata gaaaattgaa gtaaaatgtt ttcattttag
4081 caaggattta gggttctaac taaaactcag aatctttatt gagttaagaa aagtttctct
4141 accttggttt aatcaatatt tttgtaaaat cctattgtta ttacaaagag gacacttcat
4201 aggaaacatc ttttctttta gtcaggtttt taatattcag ggggaaattg aaagatatat
4261 attttagtcg attttcaaa aggggaaaaa agtccaggtc agcataagtc attttgtgta
4321 tttcactgaa gttataaggt ttttataaat gttctttgaa ggggaaaagg cacaagccaa
4381 ttttttcctat gatcaaaaaa ttctttcttt cctctgagtg agagttatct atatctgagg
4441 ctaaagttta ccttgcttta ataaataatt tgccacatca ttgcagaaga ggtatcctca
4501 tgctgggtt aatagaatat gtcagtttat cacttgtcgc ttatttagct ttaaaataaa
4561 aattaatagg caaagcaatg gaatatttgc agtttcacct aaagagcagc ataaggaggc
4621 gggaatccaa agtgaagttg tttgatatgg tctacttctt ttttggaatt tcctgaccat
4681 taattaaaga attggatttg caagtttgaa aactggaaaa gcaagagatg ggatgccata
4741 atagtaaaca gcccttgtgt tggatgtaac ccaatccag atttgagtgt gtgttgatta
4801 ttttttttgtc ttccacttt ctattatgtg taaatcactt ttatttctgc agacattttc
4861 ctctcagata ggatgacatt ttgttttgta ttattttgtc tttcctcatg aatgcactga
4921 taatatttta aatgctctat tttaagatct cttgaatctg tttttttttt ttttaatttg
4981 ggggttctgt aaggtcttta ttttcccataa gtaaatattg ccatgggagg ggggtggagg
5041 tggcaaggaa ggggtgaagt gctagtatgc aagtgggcag caattatttt tgtgttaatc
5101 agcagtacaa tttgatcgtt ggcatggtta aaaatggaa tataagatta gctgttttgt
5161 attttgatga ccaattacgc tgtattttaa cacgatgtat gtctgttttt gtggtgctct
5221 agtggtaaat aaattatttc gatgatatgt ggatgtcttt ttcctatcag taccatcatc
5281 gagtctagaa aacacctgtg atgcaataag actatctcaa gctggaaaag tcataccacc
5341 tttccgattg ccctctgtgc tttctccctt aaggacagtc acttcagaag tcatgcttta
5401 aagcacaaga gtcaggccat atccatcaag gatagaagaa atccctgtgc cgtctttta
5461 ttcccttatt tattgctatt tggtaattgt ttgagattta gtttccatcc agcttgactg
5521 ccgaccagaa aaatgcaga gagatgtttg caccatgctt tggctttctg gttctatgtt
5581 ctgccaacgc cagggccaaa agaactggtc tagacagtat ccctgtagc cccataactt
5641 ggatagttgc tgagccagcc agatataaca agagccacgt gctttctggg gttggttgtt
5701 tgggatcagc tacttgcctg tcagtttcac tggtaccact gcaccacaaa caaaaaaacc
5761 cacccattt cctccaattt ttttggctgc tacctacaag accagactcc tcaaacgagt
5821 tgccaatctc ttaataaata ggattaataa aaaaagtaat tgtgactcaa aaaaaaaaaa
5881 aa
```

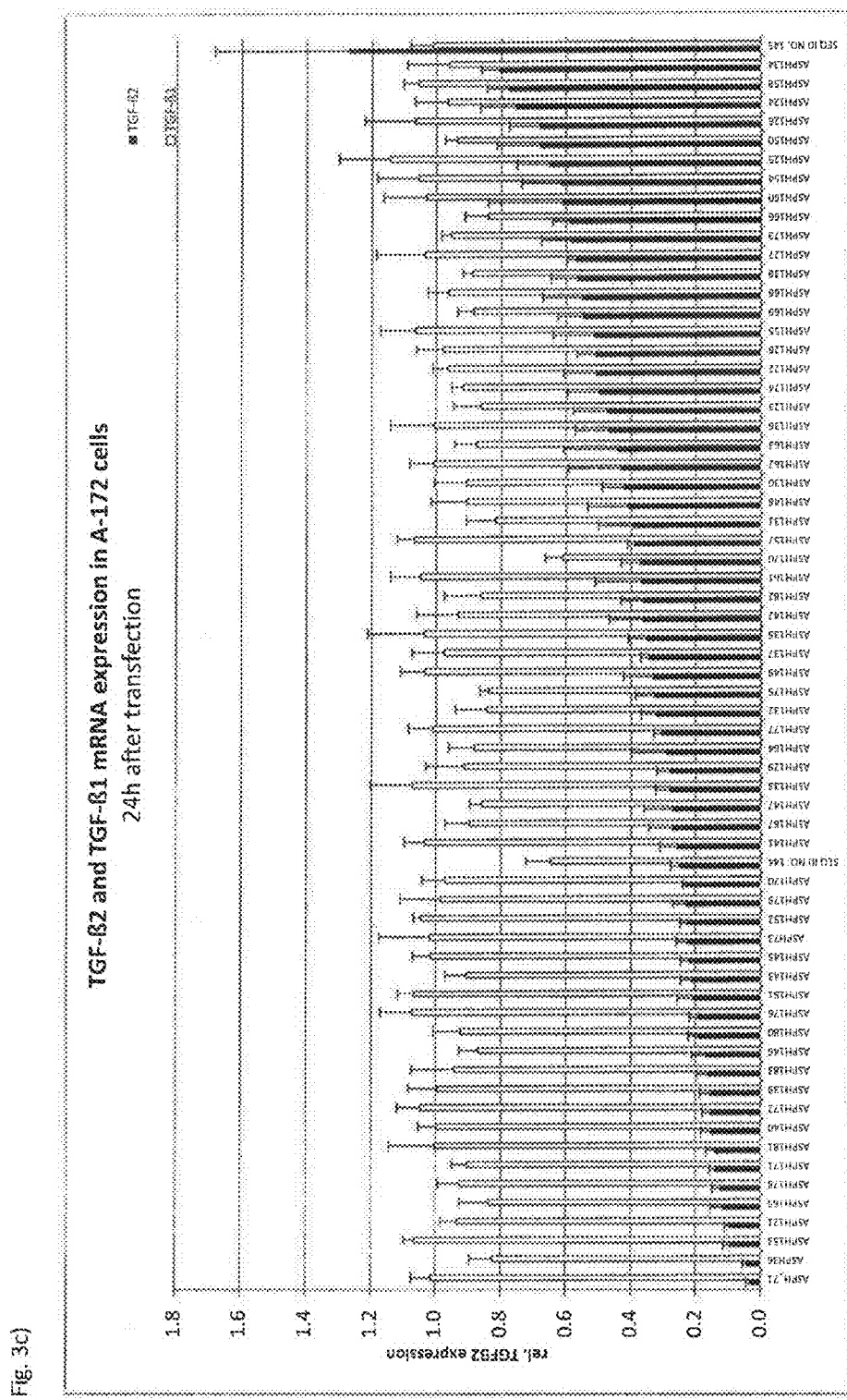

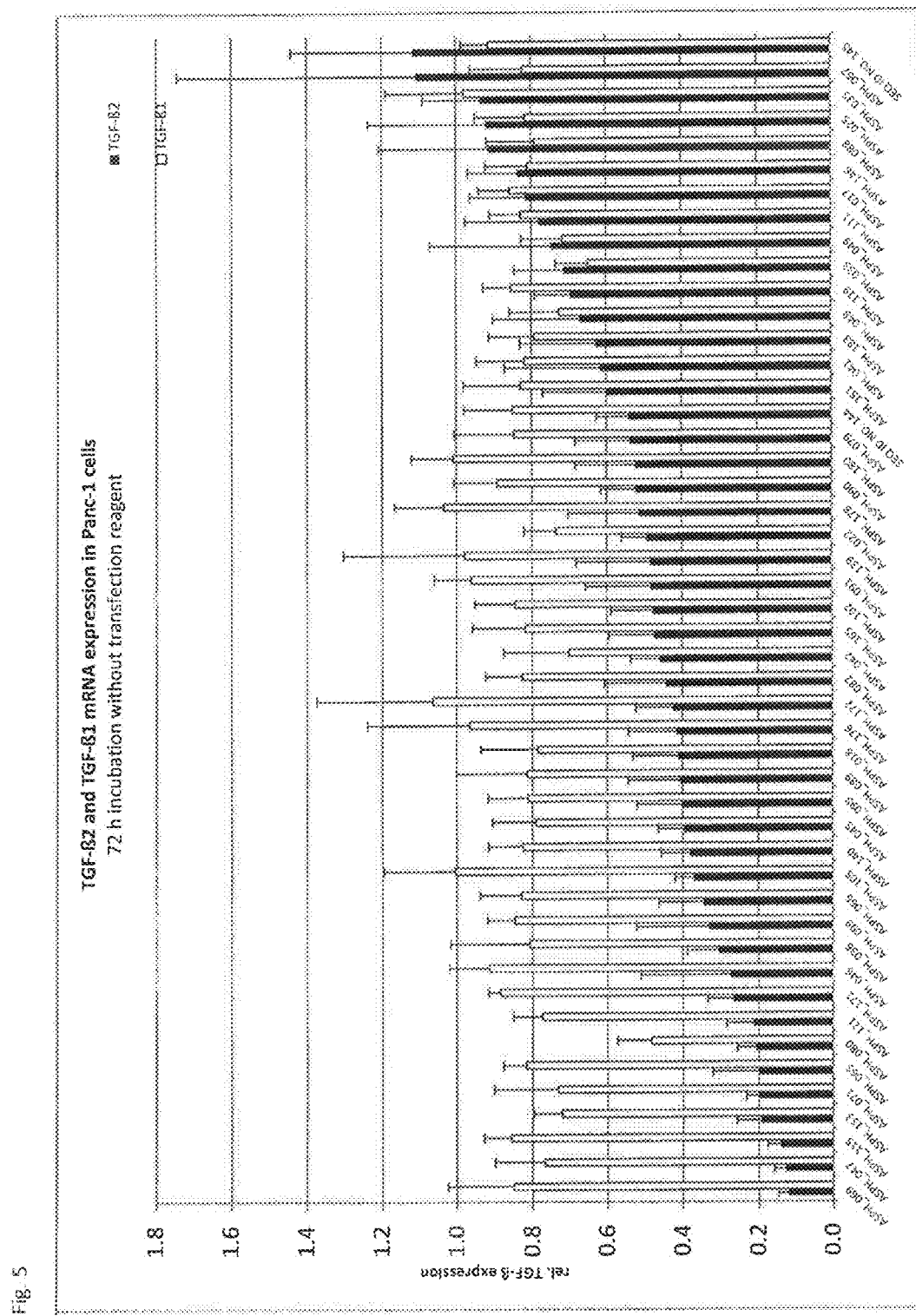

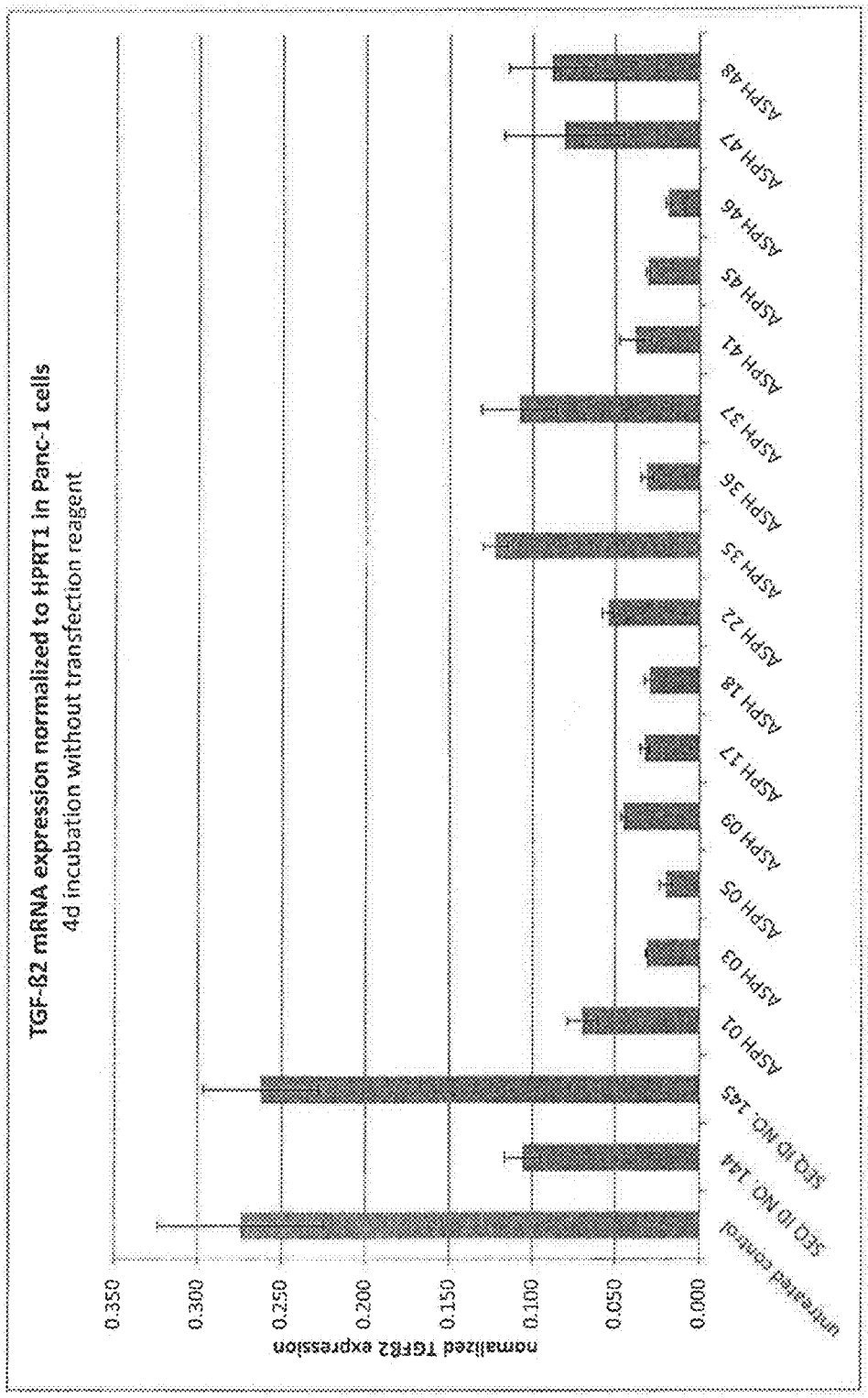

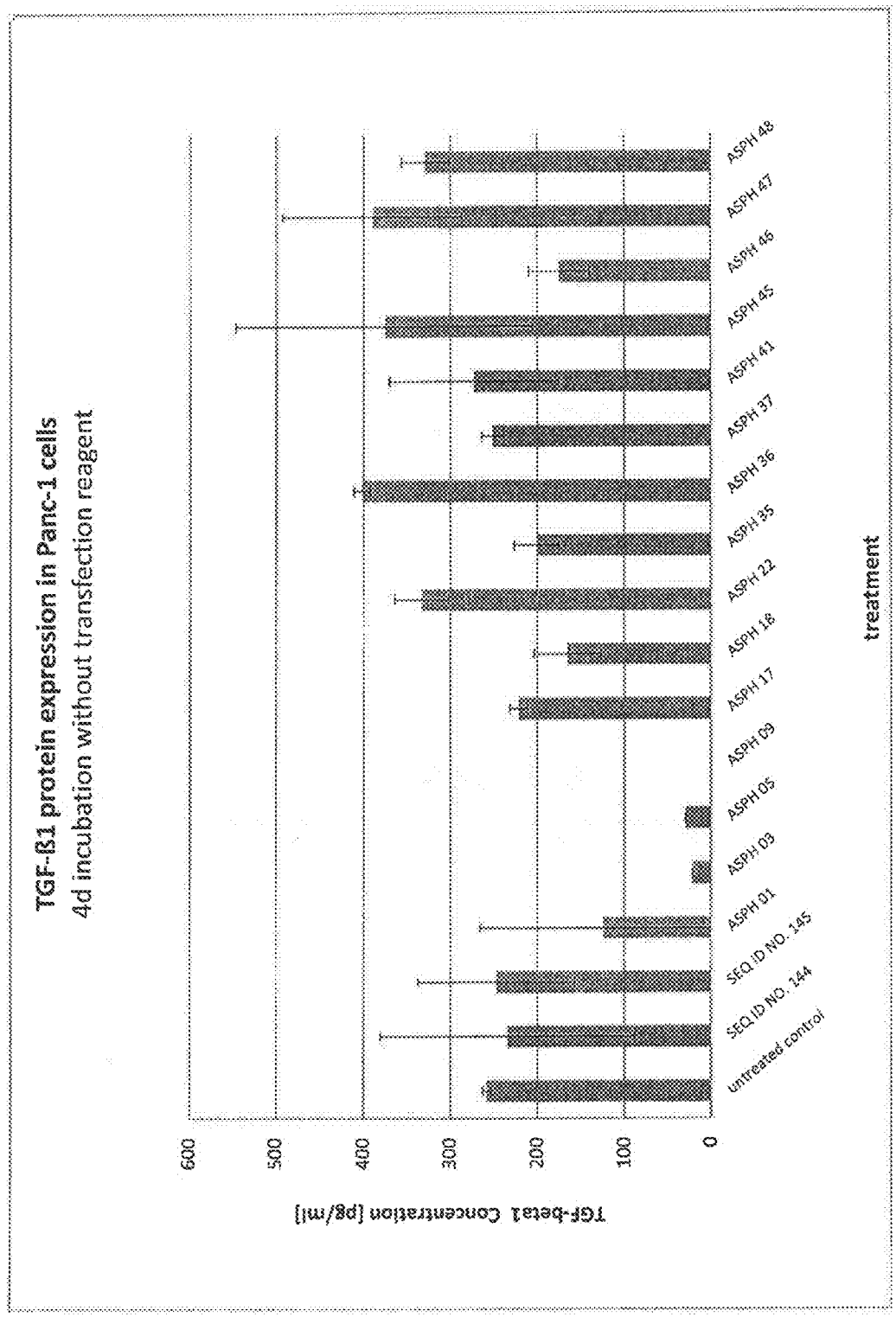

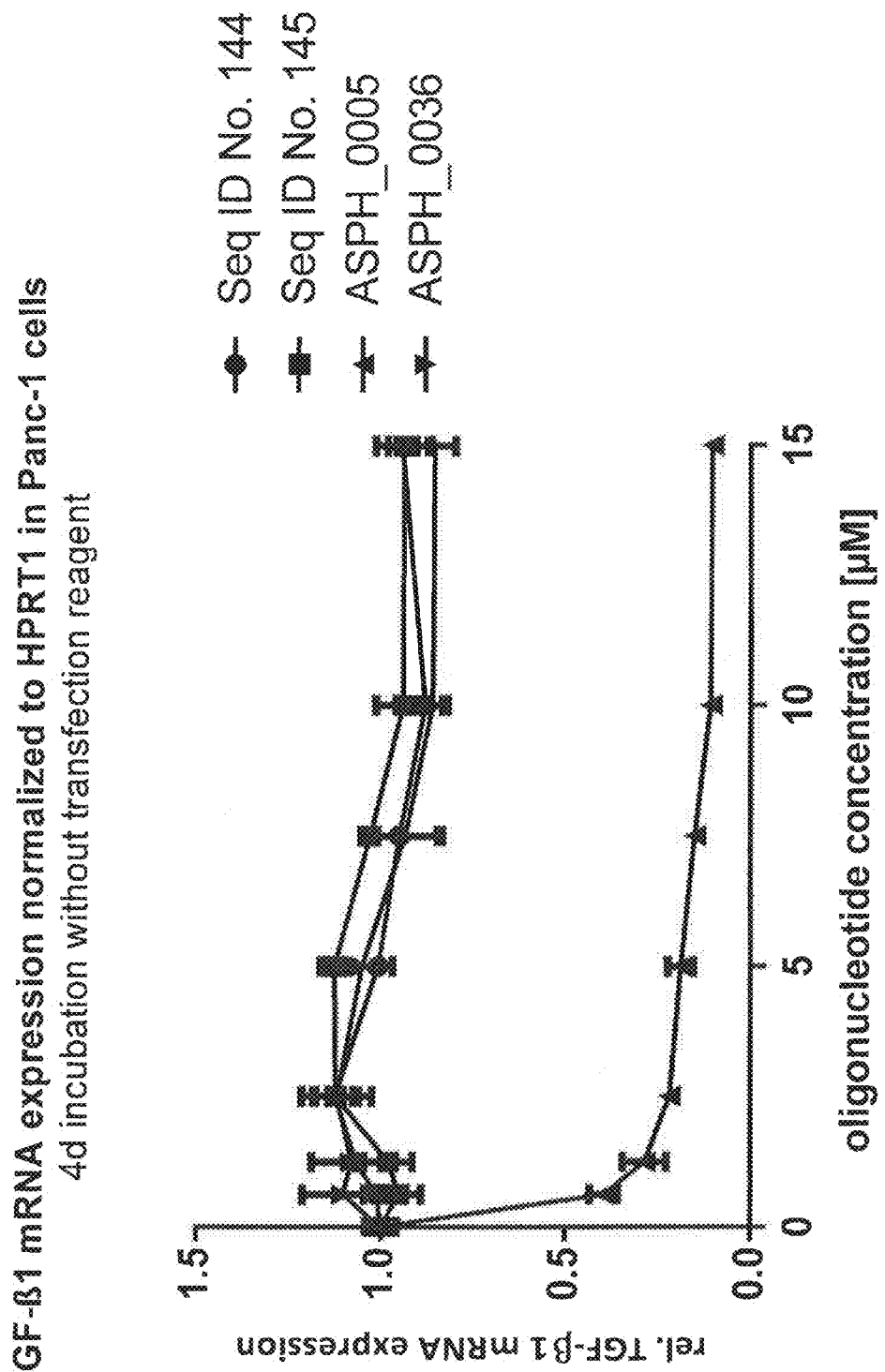

Fig. 12: Nucleic acid sequence of human TGF-beta1 (SEQ ID No. 149)
Human TGF-beta 1 mRNA (NCBI Reference Sequence: NM_000660.4)
ORIGIN

```
   1 cccgccgcc gccgccttc gcgcctggg ccatctccct cccacctccc tccgcggagc
  61 agccagacag cgagggcccc ggccggggc aggggggacg cccgtccgg ggcaccccc
 121 cggctctgag ccgcccgcgg ggccggcctc ggcccggagc ggaggaagga gtcgccgagg
 181 agcagcctga ggcccagag tctgagacga gccgccgccg ccccgccac tgcggggagg
 241 aggggagga ggagcgggag gagggacgag ctggtcggga gaagagggaa aaaacttttg
 301 agacttttcc gttgccgctg ggagccggag gcgcgggga ctcttggcgc gacgctgccc
 361 cgcgaggagg caggacttgg ggacccaga ccgcctcct ttgccgccgg ggacgcttgc
 421 tccctccctg cccctacac ggcgtcctc aggcgcccc attccggacc agcctcggg
 481 agtcgccgac ccggcctcc gcaaagactt ttccccagac ctcgggcgca ccccctgcac
 541 gccgccttca tccccggcct gtctcctgag ccccgcgca tcctagaccc tttctcctcc
 601 aggagacgga tctctctccg acctgccaca gatcccctat tcaagaccac ccaccttctg
 661 gtaccagatc gcgcccatct aggttatttc cgtgggatac tgagacaccc cggtccaag
 721 cctcccctcc accactgcgc ccttctccct gaggacctca gctttccctc gaggcctcc
 781 tacctttgc cgggagaccc ccagcctg caggggcggg gcctcccac cacaccagcc
 841 ctgttcgcgc tctcggcagt gccggggggc gccgcctcc ccatgccgcc ctcgggctg
 901 cggctgctgc cgctgctgct accgctgctg tggctactgg tgctgacgcc tggccggccg
 961 gccgcgggac tatccacctg caagactatc gacatggagc tggtgaagcg gaagcgcatc
1021 gaggccatcc gcggccagat cctgtccaag ctgcggctcg ccagcccccc gagccagggg
1081 gaggtgccgc ccggccgct gcccgaggcc gtgctcgccc tgtacaacag caccgcgac
1141 cgggtggccg gggagagtgc agaaccggag cccgagcctg aggccgacta ctacgccaag
1201 gaggtcaccc gcgtgctaat ggtggaaacc cacaacgaaa tctatgacaa gttcaagcag
1261 agtacacaca gcatatatat gttcttcaac acatcagagc tccgagaagc ggtacctgaa
1321 cccgtgttgc tctcccgggc agagctgcgt ctgctgaggc tcaagttaaa agtggagcag
1381 cacgtggaga tgtaccagaa atacagcaac aattcctggc gatacctcag caaccggctg
1441 ctggcaccca gcgactcgcc agagtggtta tcttttgatg tcaccggagt tgtgcggcag
1501 tggttgagcc gtggagggga aattgagggc tttcgcctta gcgcccactg ctcctgtgac
1561 agcaggata acacactgca agtggacatc aacgggttca ctaccggccg ccgaggtgac
1621 ctggccacca ttcatggcat gaaccggcct ttcctgcttc tcatggccac cccgctggag
1681 agggccagc atctgcaaag ctccggcac cgccgagccc tggacaccaa ctattgcttc
1741 agctccacgg agaagaactg ctgcgtgcgg cagctgtaca ttgacttccg caaggacctc
1801 ggctggaagt ggatccacga gcccaagggc taccatgcca acttctgcct cgggccctgc
1861 ccctacattt ggagcctgga cacgcagtac agcaaggtcc tggccctgta caaccagcat
1921 aaccggggcg cctcggcggc gccgtgctgc gtgccgcagg cgctggagcc gctgcccatc
1981 gtgtactacg tgggccgcaa gcccaaggtg gagcagctgt ccaacatgat cgtgcgctcc
2041 tgcaagtgca gctgaggtcc cgccccgcc cgcccgccc ggcaggccc ggcccaccc
2101 cgccccgccc ccgctgcctt gccatggggg ctgtatttta aggacacccg tgcccaagc
2161 ccacctgggg ccccattaaa gatggagaga ggactgcgga aaaaaaaaa aaaaaa
//
```

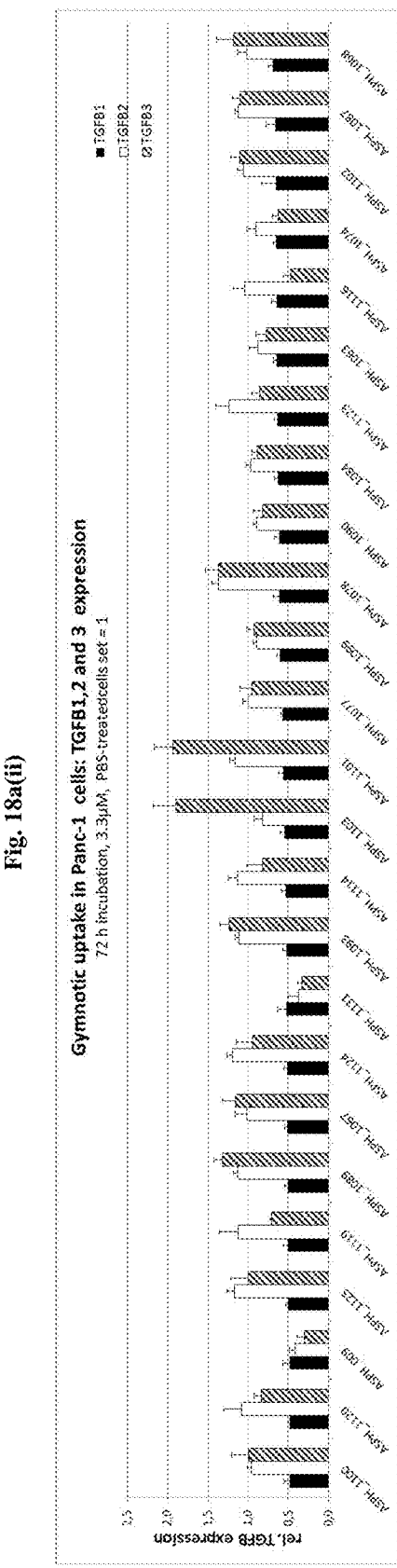
Fig. 18a(ii)

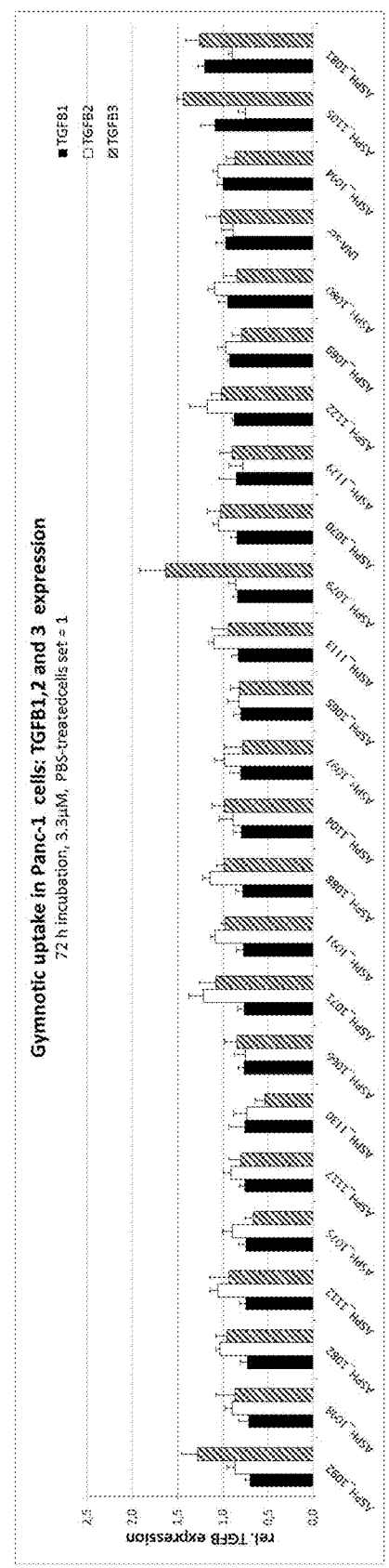
Fig. 18a(iii)

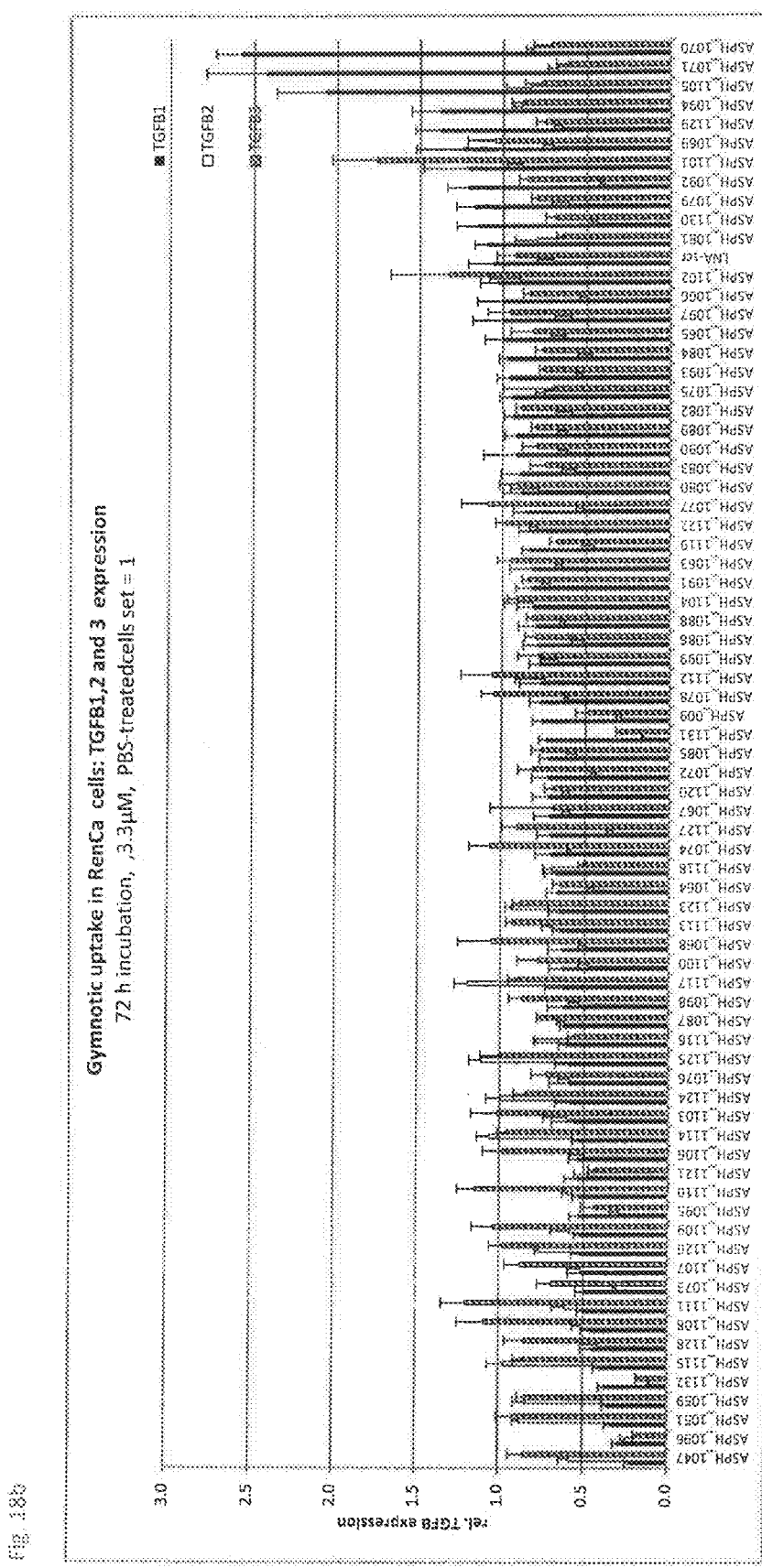

Fig. 19: Homology of ASPH_1024 and ASPH_1096 with human mRNAs

ASPH_1024 and ASPH_1096: 100% homology to human TGF-beta1 a) Position of ASPH_0009, ASPH_10024, and ASPH_1096 on human TGF-beta 2 mRNA

2361 GTGGAAATGGATACACGAACCCAAAGGGTACAATGCCAACTTCTGTGCTGGAGCATGCCC (1024: bolt+underligned, 1096: yellow shadow)

Alignment of ASPH_1096 and ASPH_1024 with human TGF-beta2 mRNA

5' AGAAGTTGGCATGGT 3' ASPH_1096
3' TCTTCAACCGTAACA 5' human TGF-beta2

5' ATGGTAGCCCTTGG 3' ASPH_1024
3' TAACATGGGAAACC 5' human TGF-beta2 b) Position of ASPH_0009, ASPH_10024, and ASPH_1096 on human TGF-beta 3 mRNA

1851 GGGTCCATGAACCTAAGGGCTACTATGCCAACTTCTGCTCAGGCCCTTGCCCATACCTCCGC (1024: bolt+underligned, 1096: yellow shadow)

Alignment of ASPH_1096 and ASPH_1024 with human TGF-beta3 mRNA

5' AGAAGTTGGCATGGT 3' ASPH_1096
3' TCTTCAACCGTATCA 5' human TGF-beta3

5' ATGGTAGCCCTTGG 3' ASPH_1024
3' TATCATCGGGAATC 3' human TGF-beta3

Fig. 20: Homology of ASPH_1131 and ASPH_1132 with human mRNAs

100% homology with human TGF-beta1 (1123-1136) and TGF-beta3 (1073-1086)

Position on human TGF-beta2 mRNA

1561 CCGGAGGTGA TTTCCATCTA CAACAGCACC AGGGACTTGC TCCAGGAGAA GGCGAGCCGG alignment with human TGF-beta 2
5' CGGGTGCTGTTGTA 3' ASPH_1132
3' GACCACGACAACAT 5' human TGF-beta2

5' CGGGTGCTGTTGTA 3' ASPH_1131
3' GACCACGACAACAT 5' human TGF-beta2

Fig. 21: Homology of ASPH_1131 and ASPH_1132 with murine mRNAs

Position on mouse TGF-beta1 mRNA

1081 CCGCTGCCCG AGGCGGTGCT CGCTTTGTAC AACAGCACCC GCGACCGGGT GGCAGGCGAG alignment with mouse TGF-beta1 mRNA
5' CGGGTGCTGTTGTA 3' ASPH_1132
3' GCCCACGACAACAT 3' mouse TGF-beta 1

5' CGGGTGCTGTTGTA 3' ASPH_1131
3' GCCCACGACAACAT 3' mouse TGF-beta1

➔ 100% homology with mouse TGF-beta 1

Position on mouse TGF-beta2 mRNA 1401 tgaggtcccc ccggaggtga tttccatcta caacagtacc aggg Alignment with mouse TGF-beta2
5' CGGGTGCTGTTGTA 3' ASPH_1132
3' GACCATGACAACAT 5' mouse TGF-beta2

5' CGGGTGCTGTTGTA 3' ASPH_1131
3' GACCATGACAACAT 5' mouse TGF-beta2

Position on mouse TGF-beta3 mRNA 1321 cactttacaa cagcacccgg gagttgctgg aagagatgca cggggagagg gaggaaggct Alignment with mouse TGF-beta3
5' CGGGTGCTGTTGTA 3' ASPH_1132
3' GCCCACGACAACAT 5' mouse TGF-beta3

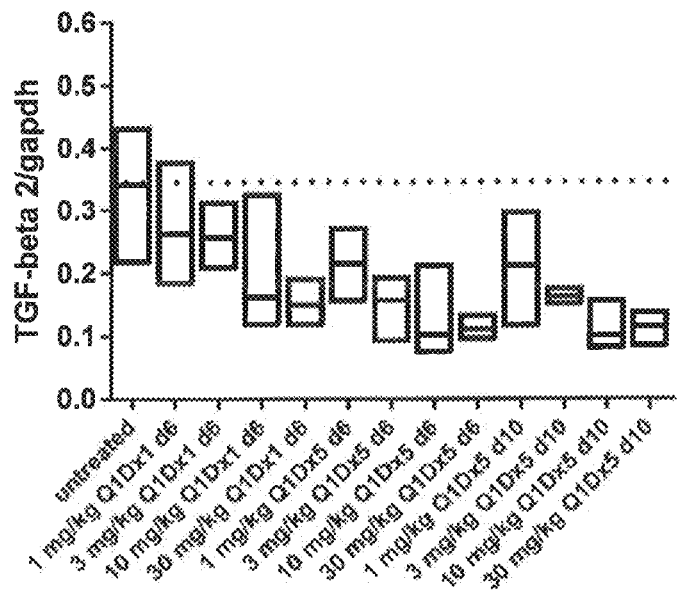
Fig. 22: TGF-beta down-regulation in kidney
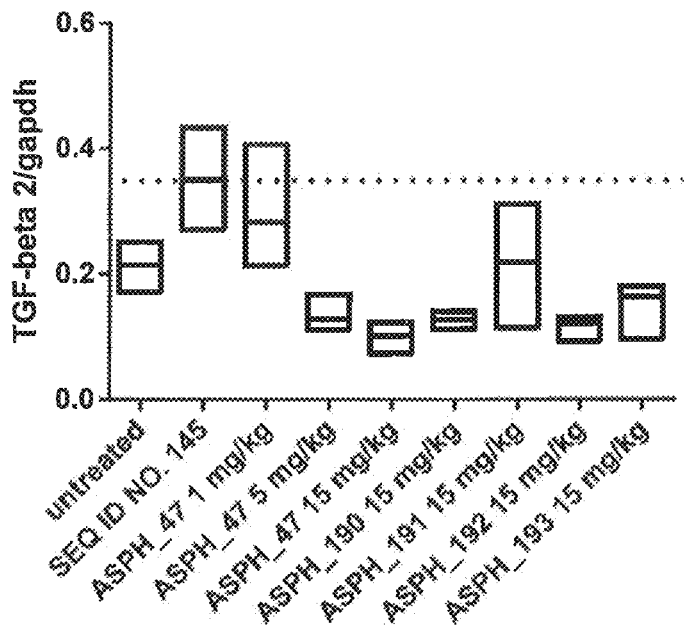
Fig. 23: TGF-beta down-regulation in human pancreatic carcinoma Panc-1 tumors Fig. 25: Nucleic acid sequence of human TGF-beta3 (SEQ ID NO. 336) – human TGF-beta3 mRNA (NCBI Reference Sequence NM_003239.2)

```
   1 gacagaagca atggccgagg cagaagacaa gccgaggtgc tggtgaccct gggcgtctga
  61 gtggatgatt ggggctgctg cgctcagagg cctgcctccc tgccttccaa tgcatataac
 121 cccacacccc agccaatgaa gacgagaggc agcgtgaaca aagtcattta gaaagccccc
 181 gaggaagtgt aaacaaaaga gaaagcatga atggagtgcc tgagagacaa gtgtgtcctg
 241 tactgccccc acctttagct gggccagcaa ctgccggcc ctgcttctcc ccacctactc
 301 actggtgatc tttttttttt tacttttttt tcccttttct tttccattct cttttcttat
 361 tttctttcaa ggcaaggcaa ggatttttgat tttgggaccc agccatggtc cttctgcttc
 421 ttctttaaaa tacccacttt ctcccatcg ccaagcggcg tttggcaata tcagatatcc
 481 actctattta ttttaccta aggaaaaact ccagctccct tccactccc agctgccttg
 541 ccacccctcc cagccctctg cttgccctcc acctggcctg ctgggagtca gagcccagca
 601 aaacctgttt agacacatgg acaagaatcc cagcgctaca aggcacacag tccgcttctt
 661 cgtcctcagg gttgccagcg cttcctggaa gtcctgaagc tctcgcagtg cagtgagttc
 721 atgcaccttc ttgccaagcc tcagtctttg ggatctgggg aggccgcctg gttttcctcc
 781 ctccttctgc acgtctgctg gggtctcttc ctctccaggc cttgccgtcc cctggcctc
 841 tcttcccagc tcacacatga agatgcactt gcaaagggct ctggtggtcc tggccctgct
 901 gaactttgcc acggtcagcc tctctctgtc cacttgcacc accttggact tggccacat
 961 caagaagaag agggtggaag ccattagggg acagatcttg agcaagctca ggctcaccag
1021 ccccctgag ccaacggtga tgacccacgt ccctatcag gtcctggccc tttacaacag
1081 caccggggag ctgctggagg agatgcatgg ggagagggag gaaggctgca cccaggaaaa
1141 caccgagtcg gaatactatg ccaaagaaat ccataaattc gacatgatcc agggctggc
1201 ggagcacaac gaactggctg tctgccctaa aggaattacc tccaaggttt tccgcttcaa
1261 tgtgtcctca gtggagaaaa atagaaccaa cctattccga gcagaattcc gggtcttgcg
1321 ggtgcccaac cccagctcta agcggaatga gcagaggatc gagctcttcc agatccttcg
1381 gccagatgag cacattgcca acagcgcta tcggtggc aagaatctgc ccacgggg
1441 cactgccgag tggctgtcct ttgatgtcac tgacactgtg cgtgagtggc tgttgagaag
1501 agagtccaac ttaggtctag aaatcagcat tcactgtcca tgtcacacct tcagcccaa
1561 tggagatatc ctggaaaaca ttcacgaggt gatggaaatc aaattcaaag gcgtggacaa
1621 tgaggatgac catggccgtg gagatctggg cgcctcaag aagcagaagg atcaccacaa
1681 ccctcatcta atcctcatga tgattccccc cacacggctc gacaacccgg gccaggggg
1741 tcagaggaag aagcgggctt tggacaccaa ttactgcttc cgcaacttgg aggagaactg
1801 ctgtgtgcgc ccctctaca ttgacttccg acaggatctg ggctggaagt gggtccatga
1861 acctaaggc tactatgcca acttctgctc aggcccttgc ccatacctcc gcagtgcaga
1921 cacaacccac agcacggtgc tgggactgta caacactctg aaccctgaag catctgcctc
1981 gccttgctgc gtgccccagg acctggagcc cctgaccatc ctgtactatg ttgggaggac
2041 ccccaaagtg gagcagctct ccaacatggt ggtgaagtct tgtaaatgta gctgagaccc
2101 cacgtgcgac agagagaggg gagagagaac caccactgcc tgactgcccg ctcctcggga
2161 aacacacaag caacaaacct cactgagagg cctggagccc acaaccttcg gtccgggca
2221 aatggctgag atggaggttt ccttttggaa catttcttc ttgctggctc tgagaatcac
2281 ggtggtaaag aaagtgtggg tttggttaga ggaaggctga actcttcaga acacacagac
2341 tttctgtgac gcagacagag gggatgggga tagaggaaag ggatggtaag ttgagatgtt
2401 gtgtggcaat gggatttggg ctaccctaaa gggagaagga agggcagaga atggctgggt
2461 cagggccaga ctggaagaca cttcagatct gaggttggat ttgctcattg ctgtaccaca
2521 tctgctctag ggaatctgga ttatgttata caaggcaagc atttttttt tttttttaaa
2581 gacaggttac gaagacaaag tccagaatt gtatctcata ctgtctggga ttaagggcaa
2641 atctattact tttgcaaact gtcctctaca tcaattaaca tcgtgggtca ctacaggag
2701 aaaatccagg tcatgcagtt cctggcccat caactgtatt gggccttttg gatatgctga
2761 acgcagaaga aagggtggaa atcaaccctc tcctgtctgc cctctgggtc cctcctctca
2821 cctctccctc gatcatattt cccttgac acttggttag acgccttcca ggtcaggatg
2881 cacatttctg gattgtggtt ccatgcagcc ttggggcatt atgggttctt ccccccttc
2941 ccctccaaga ccctgtgttc atttggtgtt cctggaagca ggtgctacaa catgtgaggc
3001 attcggggaa gctgcacatg tgccacacag tgacttggcc ccagacgcat agactgaggt
3061 ataagacaa gtatgaatat tactctcaaa atctttgtat aaataaatat ttttgggca
3121 tcctggatga tttcatcttc tggaatattg tttctagaac agtaaaagcc ttattctaag
3181 gtg
```

Fig. 26a: Effect on protein level by use of ASPH47
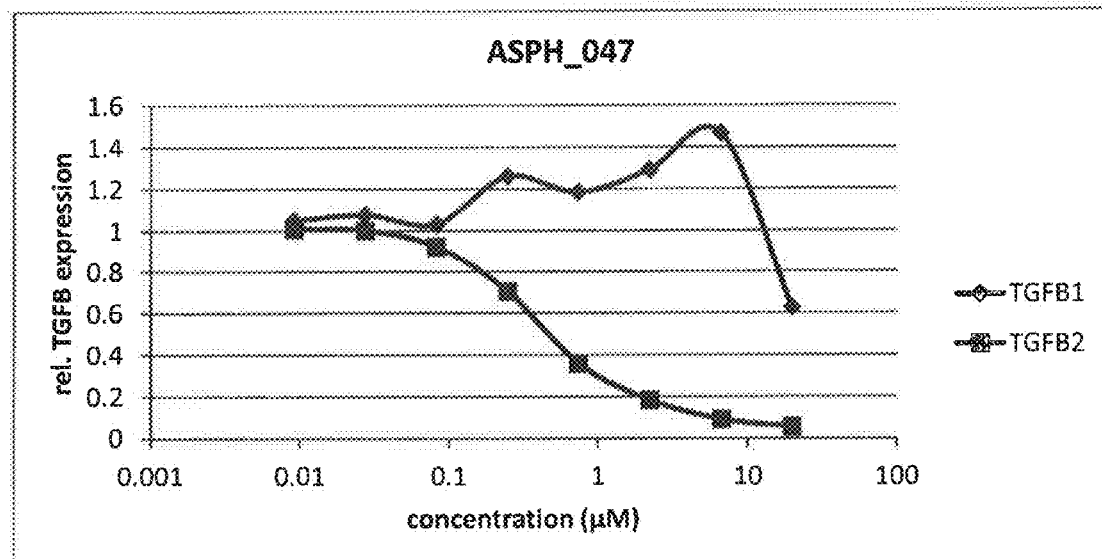
Fig. 26b: Effect on protein level by use of ASPH1047
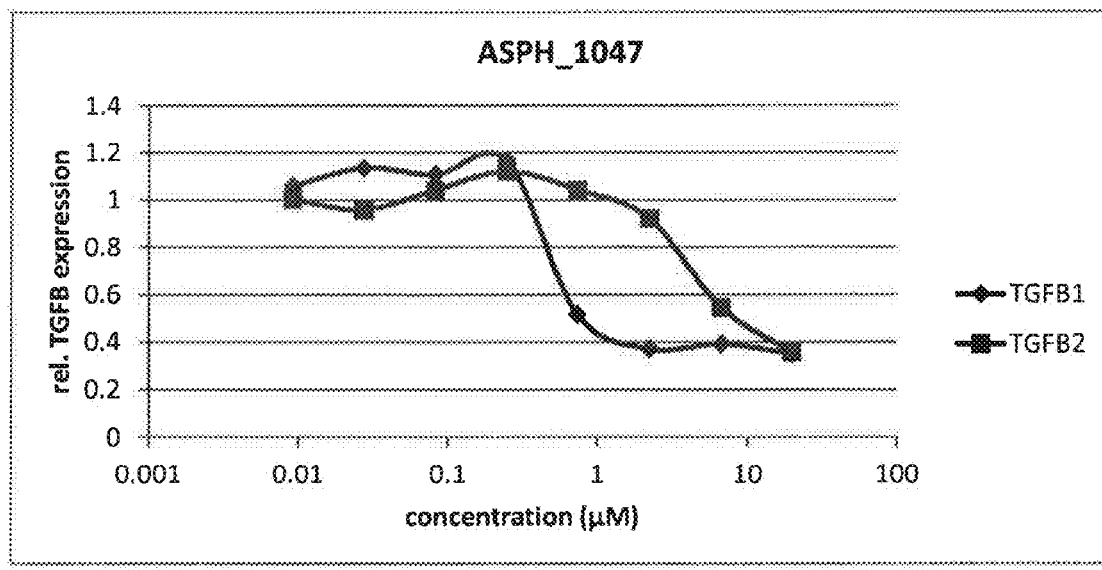

Fig. 26c: Effect on protein level by use of ASPH1106
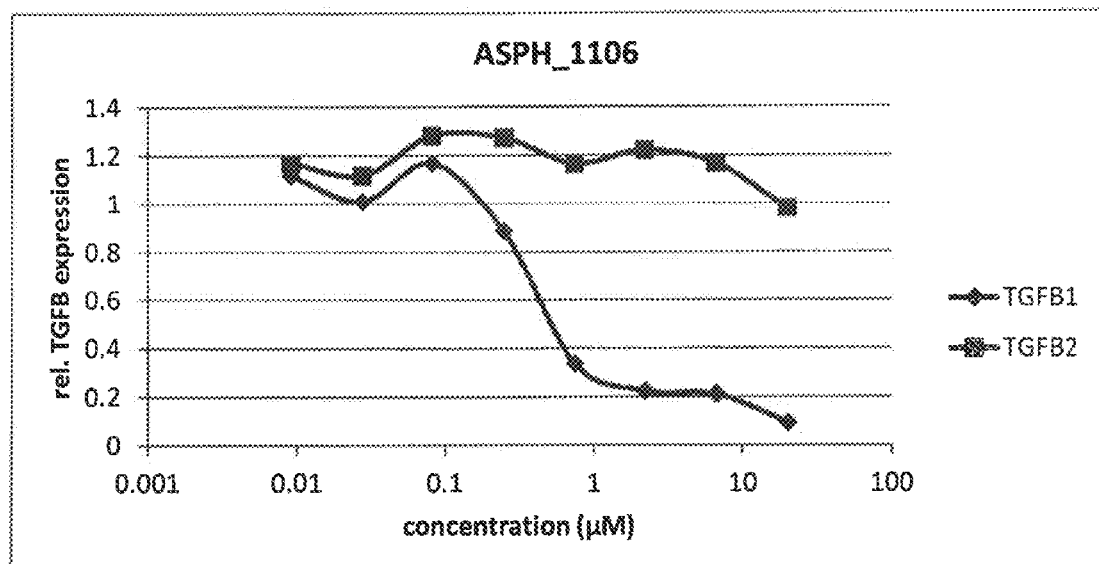
Fig. 26d: Effect on protein level by use of multispecific ASPH1132
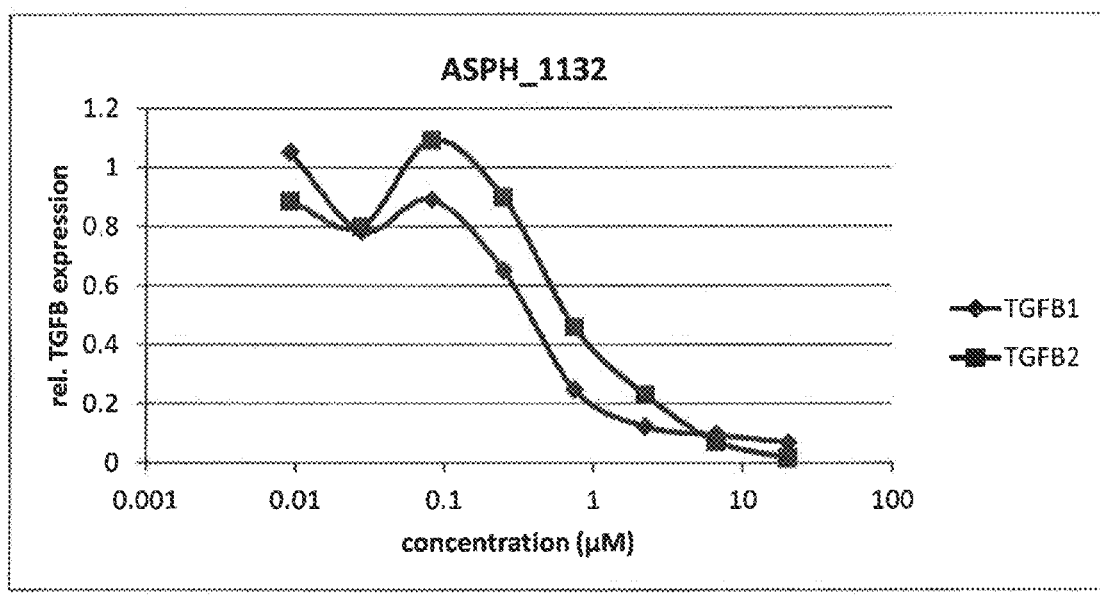

Fig. 26e: Effect on protein level by use of a combination of ASPH47 and ASPH1047
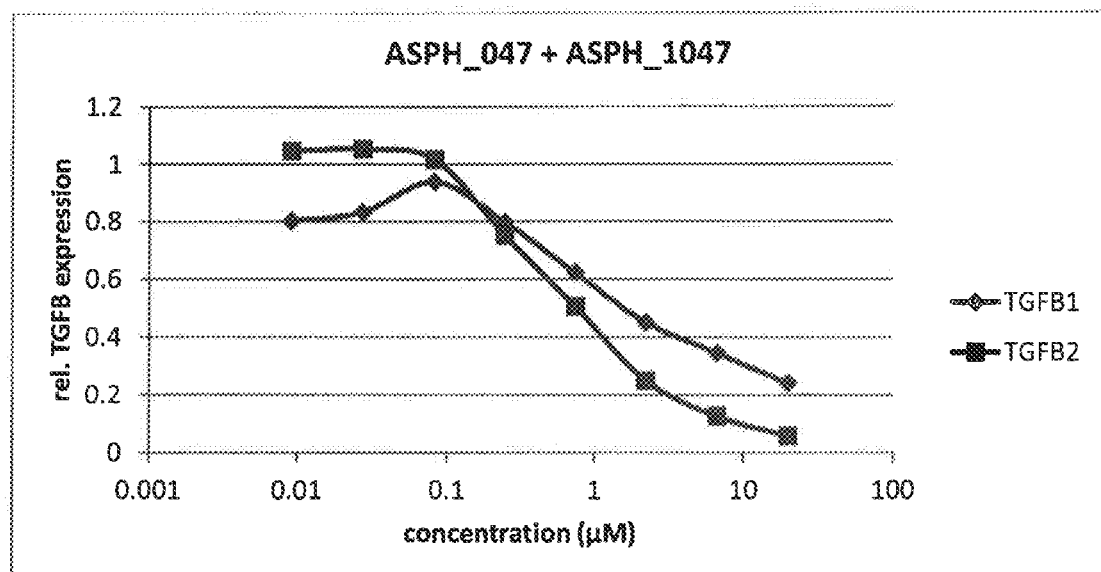
Fig. 26f: negative control - scrLNA
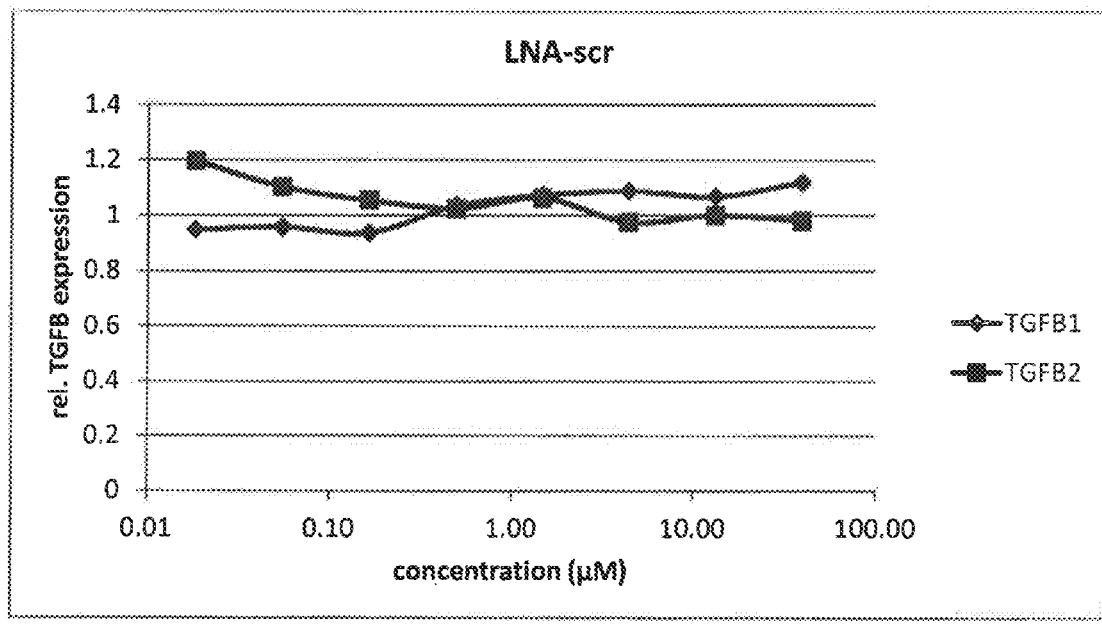

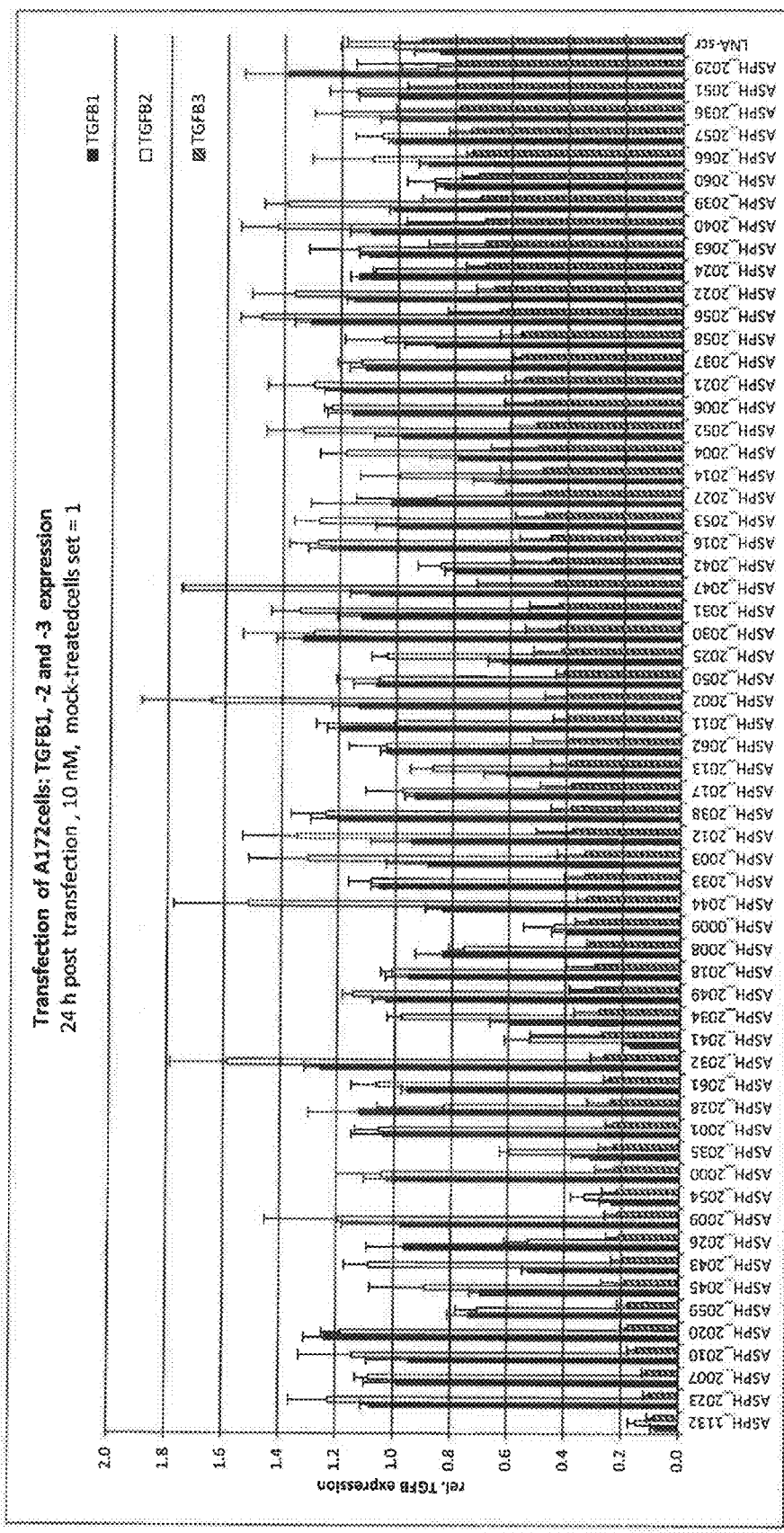
Fig. 28)

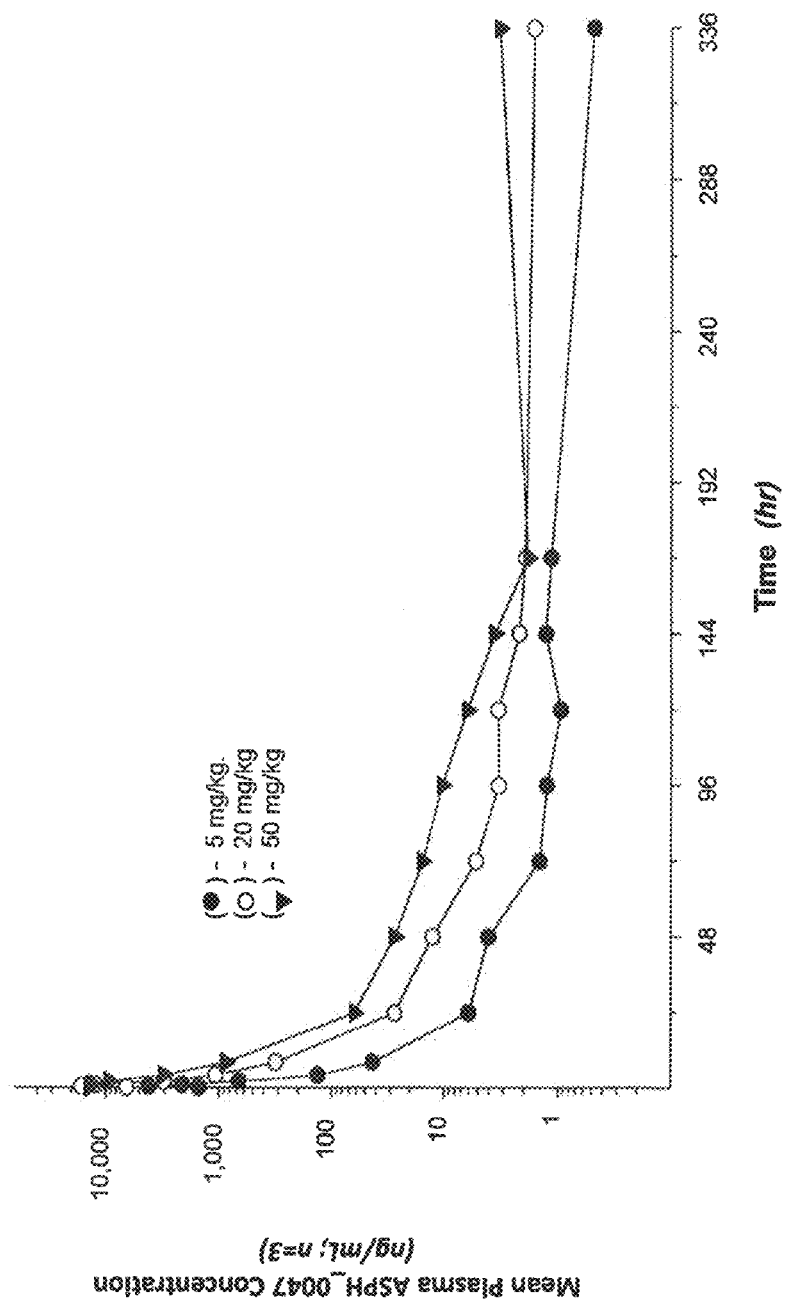
Fig. 29a) Tissue distribution of ASPH0047

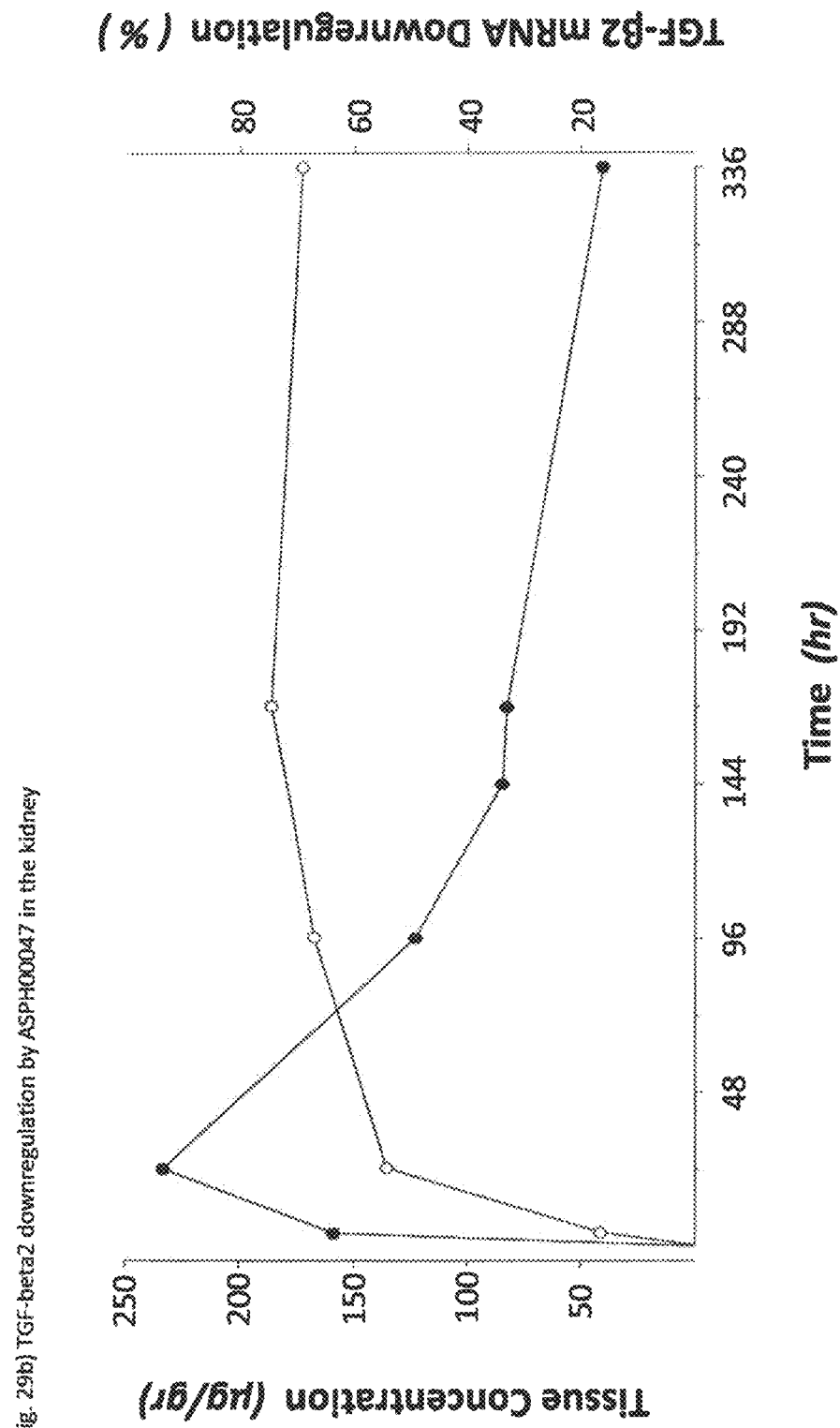
Fig. 29b) TGF-beta2 downregulation by ASPH000047 in the kidney

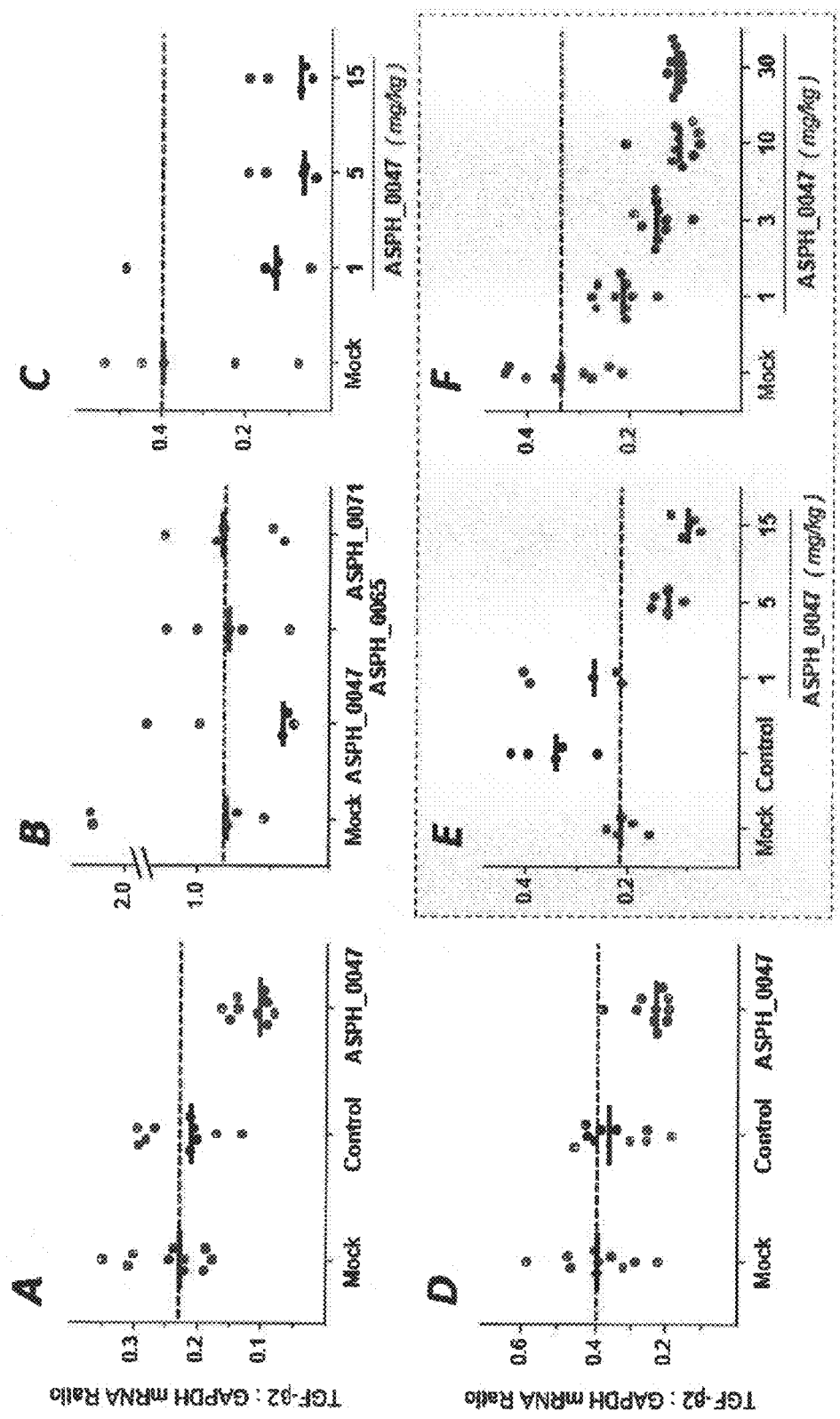
Fig. 30) TGF-β2 mRNA downregulation in established subcutaneous tumors (A-D) or kidney (E-F)

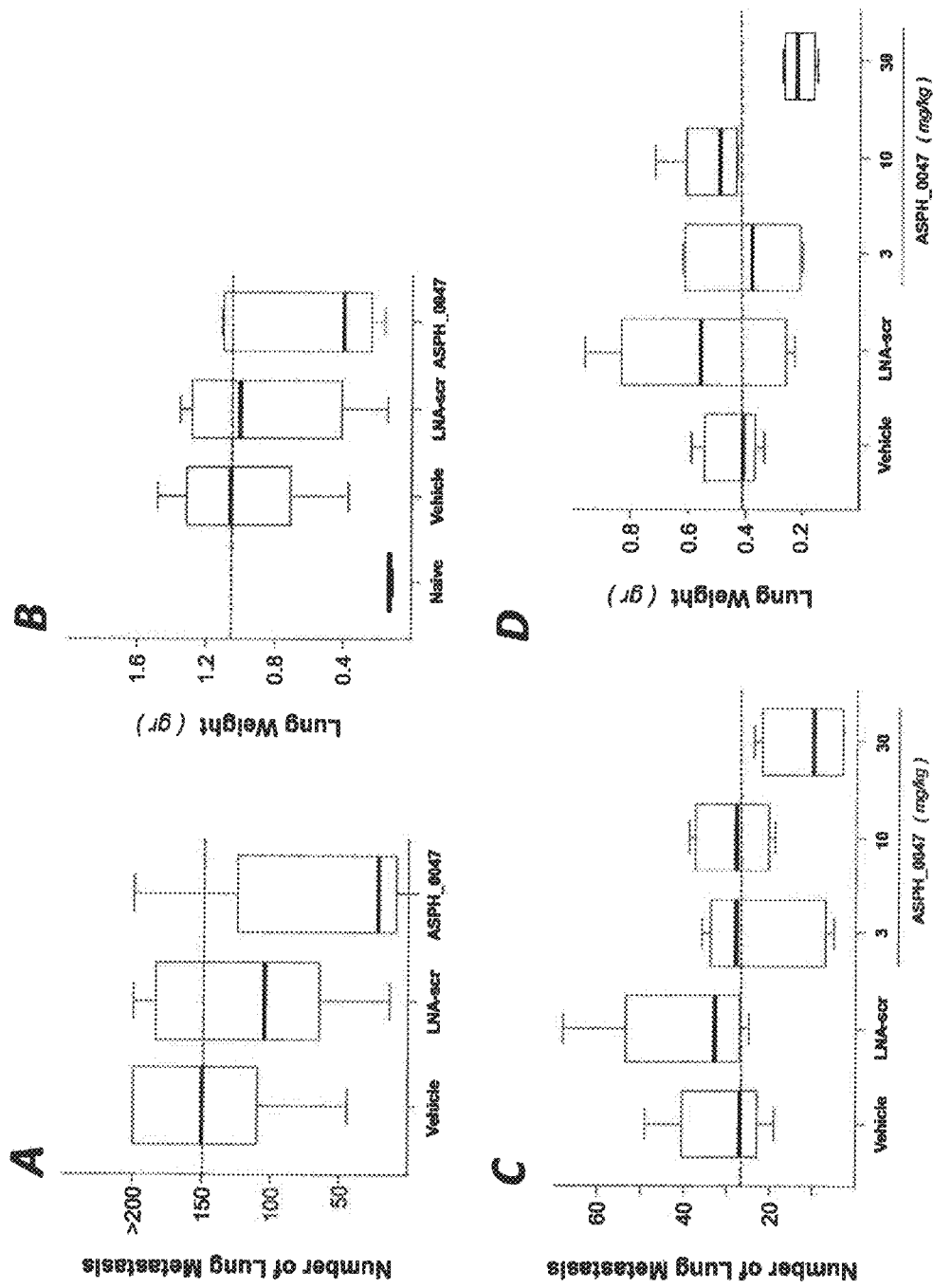
Fig. 31) Effect of systemic treatment of Balb/c mice with ASPH_0047 on lung metastasis in orthotopic and intravenous Renca models

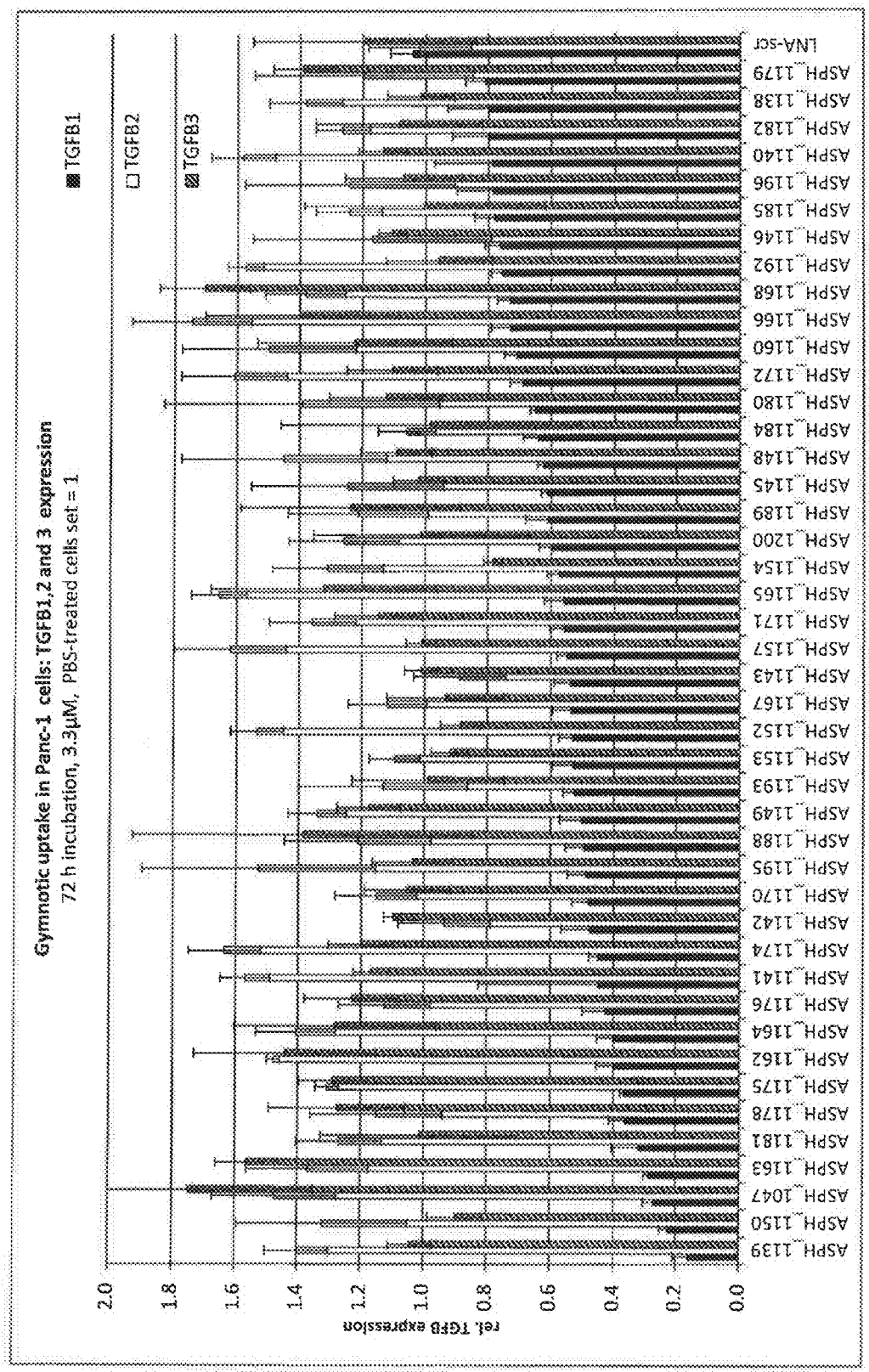
Fig. 32)

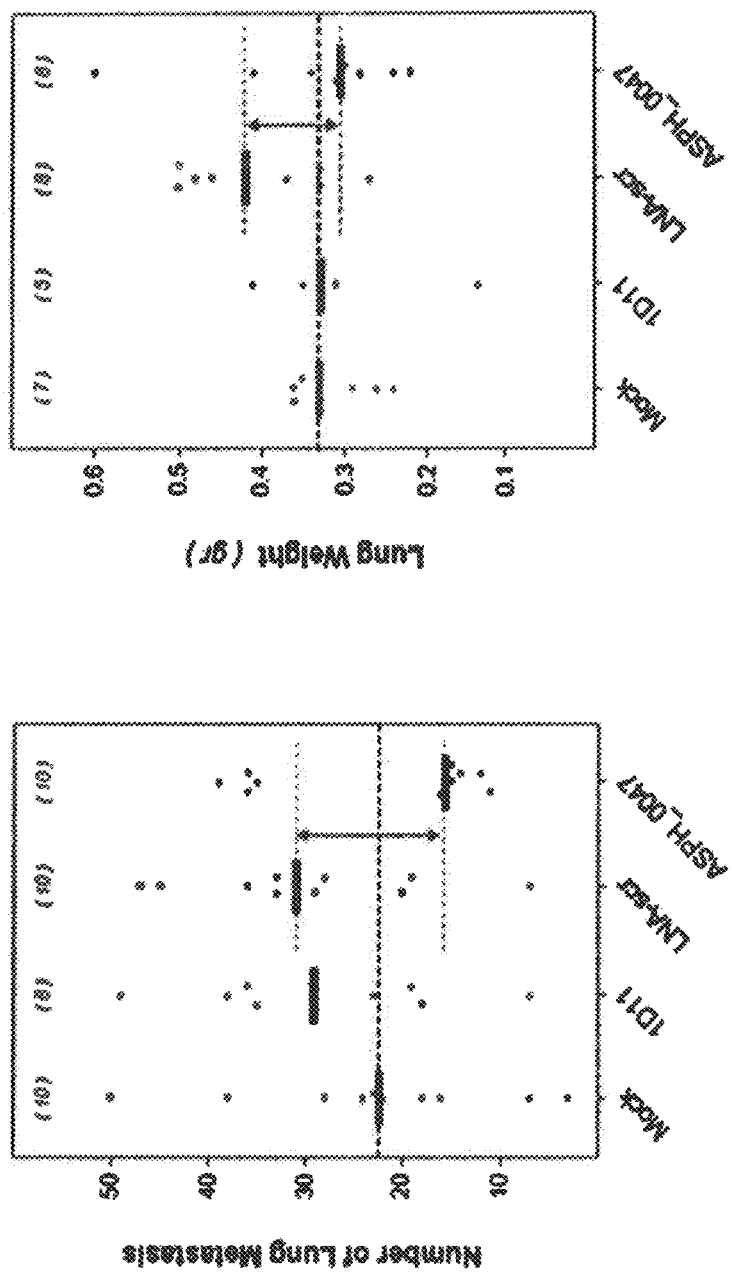
Fig. 33) Effect of systemic treatment of Balb/c mice with ASPH_0047 on lung metastasis in orthotopic mouse mammary carcinoma 4T1 model

MODIFIED TGF-BETA OLIGONUCLEOTIDES

CROSS REFERENCE TO RELATED APPLICATIONS

This application claims the priority of PCT/EP2014/056221, filed on Mar. 27, 2014, which claims the benefit of priority to European Patent Application No. 13199826.2, filed Dec. 30, 2013, European Patent Application No. 13173078.0, filed Jun. 20, 2013, and European Patent Application No. 13161474.5, filed Mar. 27, 2013, the entire contents of each of which are hereby incorporated in total by reference.

SEQUENCE LISTING

This application incorporates by reference the Sequence Listing contained in an ASCII text file named "362346_0029_SeqList.txt" submitted via EFS-Web. The text file was created on Sep. 25, 2015, and is 89.4 kb in size.

BACKGROUND OF THE INVENTION

The invention is directed to oligonucleotides consisting of 10 to 20 nucleotides of elected regions of the TGF-beta2 nucleic acid sequence, alternatively elected of the TGF-beta1 or TGF-beta3 nucleic acid sequence, which comprise modified nucleotides such as LNA, ENA, polyalkylene oxide-, 2'-fluoro, 2'-O-methoxy and/or 2'-O-methyl modified nucleotides.

Transforming growth factor beta (TGF-beta) is a protein that controls proliferation, cellular differentiation, and other functions in most cells. It is a type of cytokine which plays amongst others a role in immunity, cancer, heart disease, diabetes, Marfan syndrome, Loeys-Dietz syndrome, Parkinson's disease, and AIDS.

TGF-beta is a secreted protein that exists in at least three isoforms (TGF-beta1, TGF-beta2 and TGF-beta3) encoded by different genes but sharing strong sequence and structure homologies. TGF-beta acts as an antiproliferative factor in normal epithelial cells and at early stages of oncogenesis. However, later in tumor development TGF-beta can become tumor promoting through mechanisms including the induction of epithelial-to-mesenchymal transition (EMT), a process that is thought to contribute to tumor progression, invasion and metastasis (see "Glycoproteomic analysis of two mouse mammary cell lines during transforming growth factor (TGF)-beta induced epithelial to mesenchymal transition" 7$^{th}$ space.com.2009-01-08. Retrieved: 2009 Jan. 29).

In normal (epithelial) cells, TGF-beta stops the cell cycle at the G1 stage (and stops cell proliferation), induce differentiation, or promote apoptosis. When a cell is transformed into a cancer cell, TGF-beta no longer suppresses cell proliferation, which is often the result of mutations in the signaling pathway, and cancer cells proliferate. Proliferation of stromal fibroblasts is also induced by TGF-beta. Both cells increase their production of TGF-beta. This TGF-beta acts on the surrounding stromal cells, immune cells, endothelial, smooth-muscle cells, and tumor microenvironment (see Pickupet al., "The roles of TGFβ in the tumour microenvironment", Nature Reviews Cancer (2013), 13: 788-799). Thereby, it promotes angiogenesis, and by suppressing proliferation and activation of immune cells it causes immunosuppression.

TGF-beta1-deficient mice die from cardiac, pulmonary, and gastric inflammation, suggesting that TGF-beta has a vital role in suppressing the activation and proliferation of inflammatory cells. Smad3 is one of the key elements in TGF-beta dependent downstream signaling pathways. Smad3-deficient mice develop chronic mucosal infections due to impairment of T-cell activation and mucosal immunity, suggesting a key role for TGF-beta in these processes. With respect to cancer, the production and secretion of TGF-beta by certain cancer cells suppress the activities of infiltrating immune cells, thereby helping the tumor to escape host immunosurveillance. This immunosuppressive effect may be another important mechanism by which TGF-beta stimulates the growth of late-stage tumors (see Blobe G C et al., May 2000, "Role of transforming growth factor beta in human disease", N. Engl. J. Med. 342 (18), 1350-1358). TGF-beta also converts effector T-cells, which normally attack cancer with an inflammatory (immune) reaction, into regulatory (suppressor) T-cells, which turn off the inflammatory reaction.

Further, TGF-beta is one of the most potent regulators of the production and deposition of extracellular matrix. It stimulates the production and affects the adhesive properties of the extracellular matrix by two major mechanisms. First, TGF-beta stimulates fibroblasts and other cells to produce extracellular-matrix proteins and cell-adhesion proteins, including collagen, fibronectin, and integrins. Second, TGF-beta decreases the production of enzymes that degrade the extracellular matrix, including collagenase, heparinase, and stromelysin, and increases the production of proteins that inhibit enzymes that degrade the extracellular matrix, including plasminogen-activator inhibitor type 1 and tissue inhibitor of metalloprotease. The net effect of these changes is to increase the production of extracellular-matrix proteins and either to increase or to decrease the adhesive properties of cells in a cell-specific manner. In many cancer cells the production of TGF-beta is increased, which increases the invasiveness of the cells by increasing their proteolytic activity and promoting their binding to cell-adhesion molecules (see Blobe G C et al., May 2000, "Role of transforming growth factor beta in human disease", N. Engl. J. Med. 342 (18), 1350-1358).

Thus, therapeutic agents which are able to influence TGF-beta expression and activity, respectively, are essential in particular for use in preventing and/or treating TGF-beta linked diseases. EP 1008649 and EP 0695354, for example, disclose oligonucleotides hybridizing with the mRNA of TGF-beta1 and/or TGF-beta2, and which are suitable to be used for manufacturing pharmaceutical compositions for example for preventing and/or treating cancer. None of these oligonucleotides comprises modifications such as LNA, ENA etc.

WO 2003/85110, WO 2005/061710, and WO 2008/138904 for example refer to oligonucleotides comprising modifications of the nucleotides, which are directed to the inhibition of HIF-1A, Bcl-2 and HER3, respectively, usable in the treatment of cancer.

Criteria for the selection of oligonucleotides are mainly the length of the oligonucleotide, the GC-percentage, the tendency for hairpin formation, dimerization and the melting temperature (Tm). In general, high Tm (melting temperature) is preferred. Furthermore, the oligonucleotides must be specific for the target mRNA and shall not hybridize to non-target mRNAs in order to decrease potential off-target effects.

Hence, there is a high scientific and medical need for therapeutic agents, which reduce or inhibit TGF-beta expression and/or activity. Particularly, there is a long-standing need for oligonucleotides such as antisense oligonucleotides, which specifically interact and thus, reduce or inhibit the expression of TGF-beta1, TGF-beta2, and/or TGF-beta3, as well as oligonucleotides, which specifically inhibit TGF-beta1 and TGF-beta2, or TGF-beta1 and TGF-beta3, or TGF-beta2 and TGF-beta3, without causing any (severe) side effects.

SUMMARY OF THE INVENTION

The present invention refers to oligonucleotides consisting of 10 to 20, preferably 12 to 18 nucleotides of the TGF-beta2 nucleic acid sequence of SEQ ID NO. 1 (see FIG. 2), or of the TGF-beta1 nucleic acid sequence of SEQ ID NO. 335 (see FIG. 12), or of the TGF-beta3 nucleic acid sequence of SEQ ID NO. 336 (see FIG. 25), wherein one or more nucleotide(s) of the oligonucleotide is/are modified. Some of the oligonucleotides of the present invention correspond to TGF-beta1, TGF-beta2, and TGF-beta3, or to TGF-beta1 and TGF-beta2, or TGF-beta1 and TGF-beta3, or TGF-beta2 and TGF-beta3. Preferred oligonucleotides comprise or consist of one of SEQ ID NO. 2 to 149 (TGF-beta2), of one of SEQ ID No. 150-334 (TGF-beta1), or of one of SEQ ID No. 337-402 (TGF-beta3), which are presented in Table 1.

In particular, oligonucleotides of the present invention comprise or consist of 10 to 20, more preferred of 12 to 18 nucleotides of the region of nucleic acid no. 1380 to 1510 of SEQ ID NO. 1, wherein one or more nucleotide(s) of the oligonucleotide is/are modified. These oligonucleotides are highly effective in the reduction and inhibition of TGF-beta2 expression and activity, respectively. A preferred oligonucleotide comprises or consists of SEQ ID NO. 2 (e.g., ASPH36: GACCAGATGCAGGA), SEQ ID NO. 3 (e.g., ASPH80: GCGACCGTGACCAGAT), SEQ ID NO. 4 (e.g., ASPH98: GCGCGACCGTGACC), SEQ ID NO. 5 (e.g., ASPH111: AGCGCGACCGTGA), or SEQ ID NO. 6 (e.g., ASPH121 or ASPH153: GACCGTGACCAGAT), SEQ ID NO. 7 (e.g., ASPH15: CTGCCCGCGGAT), SEQ ID NO. 8 (e.g., ASPH17: TCTGCCCGCGGAT), SEQ ID NO. 9 (e.g., ASPH26 or ASPH27: GGATCTGCCCGCGGA), SEQ ID NO. 10 (e.g., ASPH37: CTTGCTCAGGATCTGCC), SEQ ID NO. 11 (e.g., ASPH52 or 53: GCTCAGGATCTGCCCGCGGA), SEQ ID NO. 12 (e.g., ASPH112: GGATCGCCTCGAT), SEQ ID NO. 13 (e.g., ASPH119: CCGCGGATCGCC), or SEQ ID NO. 31 (e.g., ASPH30: CGATCCTCTTGCGCAT).

In another embodiment the invention refers to an oligonucleotide, comprising or consisting of 10 to 20, more preferred of 12 to 18 nucleotides of the region of nucleic acid no. 2740 to 2810 of the TGF-beta2 nucleic acid sequence of SEQ ID NO. 1, wherein one or more nucleotide(s) of the oligonucleotide is/are modified. These oligonucleotides are highly effective in the reduction and inhibition of TGF-beta2 expression and activity, respectively. A preferred oligonucleotide comprises or consists of SEQ ID NO. 57 (e.g., ASPH65: TCTGAACTAGTACCGCC), SEQ ID NO. 73 (e.g., ASPH82: AACTAGTACCGCCTTT), or SEQ ID NO. 103 (e.g., ASPH115: CTAGTACCGCCTT).

In a further embodiment the invention refers to an oligonucleotide, comprising or consisting of 10 to 20, more preferred of 12 to 18 nucleotides of the region of nucleic acid no. 1660 to 1680 of the TGF-beta2 nucleic acid sequence of SEQ ID NO. 1 wherein one or more nucleotide(s) of the oligonucleotide is/are modified. These oligonucleotides are highly effective in the reduction and inhibition of TGF-beta1 and/or TGF-beta2 expression and activity, respectively. A preferred oligonucleotide comprises or consists of SEQ ID NO. 14 (e.g., ASHP01 or ASPH02: ACCTCCTTGGCGTAGTA), SEQ ID NO. 15 (e.g., ASPH03 or ASPH04: CCTCCTTGGCGTAGTA), SEQ ID NO. 16 (e.g., ASPH05, ASPH06, or ASPH07: CTCCTTGGCGTAGTA), or SEQ ID NO.17 (e.g., ASPH08: TCCTTGGCGTAGTA).

In another embodiment the invention relates to an oligonucleotide, comprising or consisting of 10 to 20, more preferred of 12 to 18 nucleotides, most preferably 13 nucleotides of the region of nucleic acid no. 2390 to 2410 of the TGF-beta2 nucleic acid sequence of SEQ ID NO. 1 wherein one or more nucleotide(s) of the oligonucleotide is/are modified. These oligonucleotides are highly effective in the reduction and inhibition of TGF-beta1, TGF-beta2, and/or TGF-beta3 expression and activity, respectively. A preferred oligonucleotide comprises or consists of SEQ ID NO. 18 (e.g., ASPH9 or ASPH10: CAGAAGTTGGCAT).

In another embodiment the invention relates to an oligonucleotide, comprising or consisting of 10 to 20, more preferred of 12 to 18 nucleotides of the TGF-beta2 nucleic acid sequence of SEQ ID NO. 1 wherein one or more nucleotide(s) of the oligonucleotide is/are modified. These oligonucleotides are highly effective in the reduction and inhibition of TGF-beta1, TGF-beta2, and/or TGF-beta3, most preferably of TGF-beta2 expression and activity, respectively. A preferred oligonucleotide comprises or consists of one of SEQ ID NO. 19 to 56, 58 to 72, 74 to 102, 104 to 138 (e.g., ASHP11-ASPH14, ASPH16, ASPH18-ASPH25, ASPH28-ASPH35, ASPH38-ASPH51, ASPH60-64, ASPH66-ASPH79, ASPH81, ASPH83-ASPH97, ASPH99-ASPH110, ASPH113, ASPH114, ASPH116-118, ASPH120, ASPH122-ASPH152, ASPH154-ASPH183, or T-LNA (SEQ ID NO: 144)).

Preferred oligonucleotides of the present invention are ASPH01, ASPH03, ASPH05, ASPH17, ASPH22, ASPH26, ASPH27, ASPH35, ASPH36, ASPH37, ASPH45, ASPH47, ASPH48, ASPH65, ASPH69, ASPH71, ASPH80, ASPH82, ASPH98, ASPH105, ASPH115, ASPH190, ASPH191, ASPH192, and ASPH193, respectively.

Further preferred oligonucleotides of the present invention are ASPH1000 to ASPH1132 as shown in Table 1, which preferably inhibit the expression and/or activity of TGFbeta1 mRNA. Preferred oligonucleotides this group are for example ASPH1047, ASPH1051, ASPH1059, ASPH1106, ASPH1139, ASPH1150, ASPH1162, ASPH1163, ASPH1175, ASPH1178, and ASPH1181, respectively.

In an alternative embodiment oligonucleotides are preferably inhibiting the expression and/or activity of TGF-beta3 mRNA. Such oligonucleotides are for example ASPH2000, ASPH2001, ASPH2002, ASPH2003, ASPH2004, ASPH2005, ASPH2006, ASPH2007, ASPH2008, ASPH2009, ASPH2010, ASPH2011, ASPH2012, ASPH2013, ASPH2014, ASPH2015, ASPH2016, ASPH2017, ASPH2018, ASPH2019, ASPH2020, ASPH2021, ASPH2022, ASPH2023, ASPH2024, ASPH2025, ASPH2026, ASPH2027, ASPH2028, ASPH2029, ASPH2030, ASPH2031, ASPH2032, ASPH2033, ASPH2034, ASPH2035, ASPH2036, ASPH2037, ASPH2038, ASPH2039, ASPH2040, ASPH2041, ASPH2042, ASPH2043, ASPH2044, ASPH2045, ASPH2046, ASPH2047, ASPH2048, ASPH2049, ASPH2050, ASPH2051, ASPH2052, ASPH2053, ASPH2054, ASPH2055, ASPH2056, ASPH2057, ASPH2058, ASPH2059, ASPH2060, ASPH2061, ASPH2062, ASPH2063, ASPH2064, ASPH2065, and ASPH2066, respectively.

Oligonucleotides of the present invention show an unexpected strong and specific inhibition of TGF-beta1, TGF-beta2, or TGF-beta3, or TGF-beta1 and TGF-beta2. Alternatively, oligonucleotides of the present invention show strong and specific inhibition of TGF-beta1 and TGF-beta3, or TGF-beta1 and TGF-beta2, or TGF-beta2 and TGF-beta3, and in a further alternative TGF-beta1, TGF-beta2 and TGF-beta3.

Modifications of one or more nucleotides of the oligonucleotides of the present invention are selected from the group consisting of LNA, ENA, polyalkylene oxide such as triethylene glycol (TEG), 2'-fluoro, 2'-O-methoxy and 2'-O-methyl. The modifications are preferably located at the 5'- and/or 3'-end of the oligonucleotide. An oligonucleotide comprising such modified nucleotide is a modified oligonucleotide.

Modified nucleotides are for example arranged in a row, one directly next to the other, or in different patterns, where one or more unmodified nucleotides follow a modified nucleotide. For example an oligonucleotide starts with one or more modified nucleotides followed by one or more, e.g., one, two, three or four, unmodified or unlocked nucleotides followed again by one or more modified nucleotides. In one embodiment both ends of the oligonucleotide comprise an identical pattern of modified and unmodified or unlocked nucleotides. In another embodiment, the pattern of modifications at the 3'- and 5'-end differ including that one end does not comprise a modified nucleotide. Preferably the modified oligonucleotides comprise a series of 8 or 9 unlocked nucleotides.

Alternatively, a nucleotide at any other position in the oligonucleotide is modified, or at least one nucleotide at the 5'- and/or 3'-end of the oligonucleotide and at any other position in the oligonucleotide. For example ASPH1071, ASPH1100, ASPH1109, ASPH 1110, ASPH1111, ASPH1115, ASPH1126, ASPH1127 and ASPH1128 belong to a group of TGF-beta oligonucleotides, for example TGF-beta1 oligonucleotides, which comprises modified nucleosides such as LNA, ENA etc. in different patterns, e.g., separated from each other by an unlocked nucleotide. The oligonucleotides comprise either one type of modification, or one or more different modifications. Optionally, at least one phosphate linkage between two consecutive nucleotides (modified or unmodified) of the oligonucleotide is a phosphorothioate or a methylphosphonate. In a preferred embodiment, the oligonucleotides of the present invention are phosphorothioates.

Moreover, the present invention refers to TGF-beta antisense oligonucleotides, which interact and inhibit the expression of more than one TGF-beta isoform, even if the oligonucleotide is not 100% complementary to the TGF-beta1, TGF-beta2 and/or TGF-beta3 sequence. Such antisense oligonucleotides are for example ASPH1024, ASPH1096, ASPH1131 and ASPH1132, respectively. These oligonucleotides preferably interact with TGF-beta sequences of different species such as human and mouse as for example ASPH1131 and ASPH1132, respectively.

All the oligonucleotides of the different embodiments are for use in a method of the prevention and/or treatment of a malignant or a benign tumor, an immunologic disease, fibrosis (e.g., idiopathic pulmonary fibrosis, renal fibrosis, kidney fibrosis), cirrhosis (e.g., liver cirrhosis), scleroderma or related dermatologic diseases, an eye disease such as glaucoma or posterior capsular opacification (PCO), a CNS disease, hair loss etc.

BRIEF DESCRIPTION OF THE DRAWINGS

FIG. 1 presents examples of nucleotide modifications.
FIG. 2 shows the nucleic acid sequence of human TGF-beta2 mRNA (NM_003238.3).
FIG. 3a) refers to the results for the modified oligonucleotides ASPH01, ASPH02, ASPH03, ASPH04, ASPH05, ASPH06, ASPH07, ASPH08, ASPH09, ASPH10, ASPH11, ASPH12, ASPH13, ASPH14, ASPH15, ASPH16, ASPH17, ASPH18, ASPH19, ASPH20, ASPH21, ASPH22, ASPH24, ASPH25, ASPH26, ASPH27, ASPH29, ASPH30, ASPH31, ASPH32, ASPH33, ASPH34, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, ASPH52, ASPH53, and ASPH54;
FIG. 3c) to the results for the modified oligonucleotides ASPH36, ASPH71, ASPH73, ASPH120, ASPH121, ASPH122, ASPH123, ASPH124, ASPH125, ASPH126, ASPH127, ASPH128, ASPH129, ASPH130, ASPH131, ASPH132, ASPH133, ASPH134, ASPH135, ASPH136, ASPH137, ASPH138, ASPH139, ASPH140, ASPH141, ASPH142, ASPH143, ASPH145, ASPH146, ASPH147, ASPH148, ASPH149, ASPH150, ASPH151, ASPH152, ASPH153, ASPH154, ASPH155, ASPH157, ASPH158, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183. Experiments are described in Example 1.

FIG. 4a) refers to the results for the modified oligonucleotides ASPH01, ASPH02, ASPH03, ASPH04, ASPH05, ASPH06, ASPH07, ASPH08, ASPH12, ASPH14, ASPH17, ASPH18, ASPH20, ASPH21, ASPH22, ASPH24, ASPH25, ASPH26, ASPH27, ASPH29, ASPH30, ASPH31, ASPH32, ASPH33, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, and ASPH52.

FIG. 5 shows the inhibition of the expression of TGF-beta1 and TGF-beta2 mRNA in Panc-1 cells. Panc-1 cells were treated with different modified oligonucleotides in a dose of 3.3 µM in the absence of any transfection reagent (gymnotic transfection or unassisted transfection or gymnotic delivery), and the inhibition of the TGF-beta1 (white columns) and TGF-beta2 (black columns) mRNA expression was measured after 72 h. FIG. 5 presents the results for the modified oligonucleotides ASPH17, ASPH18, ASPH22, ASPH25, ASPH33, ASPH35, ASPH36, ASPH41, ASPH42, ASPH45, ASPH46, ASPH47, ASPH48, ASPH49, ASPH65, ASPH66, ASPH67, ASPH69, ASPH71, ASPH79, ASPH80, ASPH82, ASPH88, ASPH89, ASPH90, ASPH91, ASPH98, ASPH99, ASPH102, ASPH105, ASPH111, ASPH115, ASPH119, ASPH121, ASPH139, ASPH140, ASPH146, ASPH151, ASPH153, ASPH165, ASPH171, ASPH172, ASPH176, ASPH178, ASPH180, and ASPH183. Experiments are described in Example 4.

FIG. 6 and FIG. 7 present the inhibition of the expression of TGF-beta1 (FIG. 6a) and TGF-beta2 (FIG. 6b) mRNA as well as the inhibition of TGF-beta1 (FIG. 7a) and TGF-beta2 (FIG. 7b) protein in Panc-1 cells. Panc-1 cells were treated with different modified oligonucleotides in a dose of 10 µM via gymnotic delivery, i.e., in the absence of any transfecting reagent, and the inhibition of the TGF-beta1 and TGF-beta2 mRNA expression and protein was measured 4 days after transfection.

FIG. 12 presents the nucleic acid sequence of human TGF-beta1 mRNA (NM_000660.4).

FIG. 13 refers to the results for the modified oligonucleotides ASPH05, ASPH09, ASPH1000, ASPH1001, ASPH1002, ASPH1003, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1054, ASPH1055, ASPH1056, ASPH1057, ASPH1058, ASPH1059, ASPH1060, and ASPH1061. Experiments are described in Example 12.

FIG. 14 refers to the results for the modified oligonucleotides ASPH09, ASPH1000, ASPH1001, ASPH1002, ASPH1003, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, and ASPH1062. Experiments are described in Example 13.

FIG. 15 refers to the results for the modified oligonucleotides ASPH05, ASPH09, ASPH1000, ASPH1001, ASPH1002, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1056, ASPH1057, ASPH1058, ASPH1059, ASPH1060, ASPH1061, and ASPH1062. Experiments are described in Example 14.

FIG. 16 refers to the results for the modified oligonucleotides ASPH05, ASPH09, ASPH1000, ASPH1001, ASPH1002, ASPH1004, ASPH1006, ASPH1007, ASPH1008, ASPH1009, ASPH1010, ASPH1011, ASPH1012, ASPH1013, ASPH1014, ASPH1015, ASPH1017, ASPH1018, ASPH1019, ASPH1020, ASPH1021, ASPH1022, ASPH1024, ASPH1026, ASPH1027, ASPH1028, ASPH1029, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, and ASPH1062. Experiments are described in Example 15.

FIG. 17 refers to the results for the modified oligonucleotides ASPH09, ASPH1047, ASPH1051, ASPH1059, ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132. Experiments are described in Example 16.

FIG. 18a(i), FIG. 18a(ii), and FIG. 18a(iii) refer to the results for the modified oligonucleotides ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132. FIG. 18b presents the inhibiting effect of these oligonucleotides in RenCa cells.

FIG. 19 presents a sequence alignment of ASPH1024 and ASPH1096 with the human sequence of TGF-beta1, TGF-beta2 and TGF-beta3 mRNAs. Both oligonucleotides are 100% homologous to the human sequence of TGF-beta1. ASPH1024 has three mismatches with the human sequence of TGF-beta2 (FIG. 19a) and two mismatches with human sequence of TGF-beta3 (FIG. 19b). ASPH1096 has one mismatch with the human sequence of TGF-beta2 (FIG. 19a), and one mismatch with the human sequence of TGF-beta3 (FIG. 19b). Both oligonucleotides show inhibition of different human TGF-beta isoforms (TGF-beta1, TGF-beta2, and TGF-beta3). For example ASPH1024 inhibits the expression and activity of TGF-beta1 and TGF-beta2 (see FIG. 16) and ASPH1096 inhibits the expression and activity of TGF-beta1, TGF-beta2 and TGF-beta3 as depicted in FIG. 17 for example. ASPH009, which is 100% homologous to the human sequence of TGF-beta1, TGF-beta2, and TGF-beta3 was used as a control.

FIG. 20 shows an alignment of ASPH1131 and ASPH1132 with the human sequences of TGF-beta1, TGF-beta2 and TGF-beta3 mRNAs. Both oligonucleotides are 100% homologous to the human sequences of TGF-beta1 and TGF-beta3. Each of ASPH1131 and ASPH1132 has one mismatch with the human sequence of TGF-beta2. Both oligonucleotides strongly inhibit the expression of all three human isoforms as depicted in FIG. 17 for example.

FIG. 21 depicts an alignment of ASPH1131 and ASPH1132 with the murine sequences of TGF-beta1, TGF-beta2 and TGF-beta3 mRNAs. Both oligonucleotides are 100% homologous to the murine sequences of TGF-beta1 and TGF-beta3. Each of ASPH1131 and ASPH1132 has two mismatches with the murine sequence of TGF-beta2. While ASPH1131 potently inhibits murine TGF-beta2 and TGF-beta3, ASPH1132 very potently suppresses all murine TGF-beta isoforms as depicted in FIG. 18b for example.

FIG. 22 shows TGF-beta2 mRNA expression in the kidney of mice bearing subcutaneous human pancreatic carcinoma Panc-1. Mice were treated with 1, 3, 10, and 30 mg/kg of ASPH47 after indicated treatment schedules for 5 days: Q1Dx1-d6 (single SC injection, termination 5 days later), Q1Dx5-d6 (daily SC injection for 5 days, termination 24 hours later), and Q1Dx5-d10 (daily SC injection for 5 days, termination 5 days later). TGF-beta 2 expression was detected by bDNA assay and normalized to GAPDH. Data—representing TGF-beta2 to GAPDH mRNA ratio—are shown as a box plot in which median values and min. and max. values are presented (data expressed as n=10, except n=9 for vehicle and 3 mg/kg Q1Dx1 d6 groups).

FIG. 23 depicts TGF-beta2 mRNA expression in the kidneys of mice bearing human pancreatic carcinoma Panc-1 tumors. Mice were treated with subcutaneous injections of various oligonucleotides for 5 consecutive days using indicated treatment doses: daily injection of 1, 5, 15 or 50 mg/kg oligonucleotides for five consecutive days. TGF-beta2 mRNA expression was detected by bDNA assay and normalized to GAPDH. Data—representing TGF-beta2 to GAPDH mRNA ratio—are shown as a box plot in which median values and min. and max. values are presented (data expressed as n=5).

FIG. 25 shows the nucleic acid sequence of human TGF-beta3 mRNA (NM_003239.2).

FIG. 26 depicts the inhibiting effect of oligonucleotides of the present invention on the expression of TGF-beta1 and TGF-beta2 protein. Panc-1 cells were transfected with 20, 6.67, 2.22, 0.74, 0.25, 0.08 or 0.009 µM of the modified oligonucleotides ASPH47 (FIG. 26a), ASPH1047 (FIG. 26b), ASPH1106 (FIG. 26c), ASPH1132 (FIG. 26d), or ASPH47 in combination with ASPH1047 (FIG. 26e). Negative control is the scrambled oligonucleotide (scrLNA) of SEQ ID No. 145 (FIG. 26f) in concentrations of 40, 13.33, 4.44, 1.48, 0.49, 0.16, 0.05, or 0.02 µM. TGF-beta1 (diamonds) and TGF-beta2 protein (squares) levels in cell supernatants were determined by ELISA.

FIG. 28 depicts the inhibiting effect of oligonucleotides of the present invention on the expression of TGF-beta1, TGF-beta2, and TGF-beta3. A172 glioma cells were transfected with 10 nM of different TGF-beta specific oligonucleotides in the presence of transfecting agent. The expression of TGF-beta1 (black column), TGF-beta2 (white column) and TGF-beta3 (striped column) mRNA was determined 24 h after transfection.

FIGS. 29a and 29b present a compared analysis of time-dependent plasma (29a) and kidney (29b) concentration (PK profiles; with values expressed in µg/mL or µg/gr) and downregulation of TGF-$\beta$2 mRNA (PD profile) in kidney following single subcutaneous bolus administration of 50 mg/kg of ASPH_0047 to Balb/c mice.

FIG. 30 depicts TGF-$\beta$2 mRNA downregulation in established subcutaneous tumors (FIG. 30A-D) or kidney (FIG. 30E-F) in immunodeficient mouse following subcutaneous repeated administration of ASPH_0047 or control oligonucleotide. TGF-beta2 and GAPDH mRNA expression was detected by bDNA. Results are expressed as TGF-beta2/GAPDH mRNA ratio, and each individual tested sample is represented with line indicating median values.

FIG. 31 shows the effect of systemic treatment of Balb/c mice with ASPH_0047 (selective TGF-b2 antisense oligonucleotide) on lung metastasis in orthotopic and in i.v. mouse Renca renal carcinoma model. Level of lung metastasis was determined by either number of metastasis or based on lung weight. Results are shown as a box plot in which median values, upper and lower quartiles, and 90th and 10th percentiles are presented.

FIG. 32 presents human Panc-1 pancreatic cancer cells were treated with 3.3 µM of the indicated oligonucleotides in the absence of transfecting agent (gymnotic transfection or gymnotic delivery). The expression of TGF-beta1 (black column), TGF-beta2 (white column) and TGF-beta3 (striped column) mRNA was determined 72 h after transfection.

FIG. 33 depicts the effect of systemic treatment of Balb/c mice with ASPH_0047 on lung metastasis in orthotopic mouse 4T1 mammary carcinoma model. Data for each individual animal is represented with median values indicated as bold black line.

DETAILED DESCRIPTION OF THE INVENTION

Figure 3A:
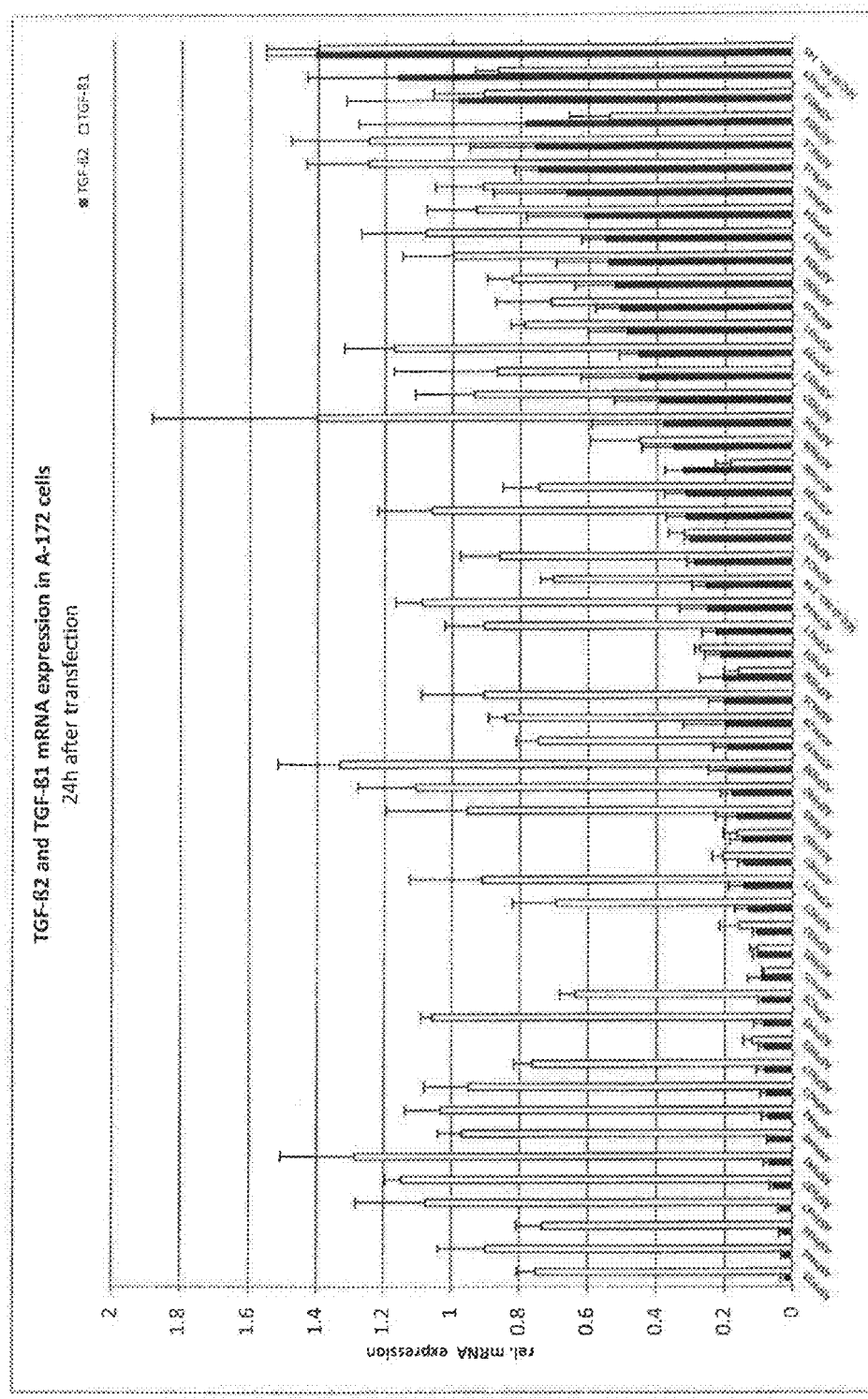
FIGS. 3a) to 3c) depict the inhibition of the expression of TGF-beta1 and TGF-beta2 mRNA in human A172 glioma cells. A172 cells were transfected with different modified oligonucleotides in a dose of 10 nM (in the presence of a transfecting agent), and the inhibition of the TGF-beta1 (white columns) and TGF-beta2 (black columns) mRNA expression was measured 24 h after transfection.

The present invention is directed to oligonucleotides, in particular antisense oligonucleotides, which comprise at least one modified nucleotide and are suitable to interact with TGF-beta mRNA. The oligonucleotides comprise or consist of 10 to 20, more preferred 12 to 18 nucleotides of the TGF-beta2 nucleic acid according to SEQ ID NO. 1 or of the TGF-beta1 nucleic acid according to SEQ ID NO. 335, or of the nucleic acid sequence of TGF-beta3 nucleic acid according to SEQ ID NO. 336. Most preferred the oligonucleotide comprises or consists of 12, 13, 14, 15, 16, 17, or 18 nucleotides. The oligonucleotides are preferably selected from the region of nucleic acid no. 1380 to 1510 (preferably no. 1380 to 1450 and/or no. 1480 to 1510), 1660 to 1680, or 2390 to 2410 of SEQ ID NO. 1. The oligonucleotide is a single or double stranded RNA or DNA, including siRNA, microRNA, apatmer or spiegelmer. Preferably, the oligonucleotide is an antisense oligonucleotide.

A nucleotide forms the building block of an oligonucleotide, and is for example composed of a nucleobase (nitrogenous base, e.g., purine or pyrimidine), a five-carbon sugar (e.g., ribose, 2-deoxyribose, arabinose, xylose, lyxose, allose, altorse, glucose, mannose, gulose, idose, galactose, talose or stabilized modifications of those sugars), and one or more phosphate groups. Examples of modified phosphate groups are phosphorothioate or methylphosphonate. Each compound of the nucleotide is modifiable, and is naturally or non-naturally occurring. The latter are for example locked nucleic acid (LNA), a 2'-O,4'-C-ethylene-bridged nucleic acid (ENA), polyalkylene oxide- (such as triethylene glycol (TEG)), 2'-fluoro, 2'-O-methoxy and 2'-O-methyl modified nucleotides as described for example by Freier & Altmann (Nucl. Acid Res., 1997, 25, 4429-4443) and Uhlmann (Curr. Opinion in Drug & Development (2000, 3 (2): 293-213), which are shown in FIG. 1.

A LNA is a modified RNA nucleotide, wherein the ribose moiety is modified with an extra bridge connecting the 2' oxygen and 4' carbon (2'-4'ribonucleoside). The bridge "locks" the ribose in the 3'-endo (North) conformation, which is often found in the A-form duplexes. LNA nucleosides and nucleotides, respectively, comprise for example the forms of thio-LNA, oxy-LNA, or amino-LNA, in alpha-D- or beta-L-configuration, and are mixable and combineable, respectively, with DNA or RNA residues in the oligonucleotide.

The oligonucleotides of the present invention, i.e., modified oligonucleotides, comprise at least one modified nucleotide, preferably LNA and/or ENA, at the 5'- and/or 3'-end of the oligonucleotide. In a preferred embodiment, the oligonucleotide comprises 1, 2, 3, or 4 LNAs or ENAs at the 5'-end, and 1, 2, 3, or 4 LNAs or ENAs at the 3'-end. In another preferred embodiment, the oligonucleotide comprises 1, 2, 3, or 4 LNAs or ENAs at the 5'-end or 3'-end, and a polyalkylene oxide such as TEG at the 3'- or 5'-end. The modified oligonucleotides show a significantly increased inhibition on TGF-beta expression and activity, respectively, which results in an improved prevention and/or treatment of a malignant or benign tumor, fibrosis (e.g., idiopathic pulmonary fibrosis, renal fibrosis, kidney fibrosis), cirrhosis (e.g., liver cirrhosis), scleroderma or related dermatologic diseases, an eye disease such as glaucoma or posterior capsular opacification (PCO), a CNS disease, hair loss etc. The oligonucleotides of the present invention target TGF-beta linked diseases either by hybridization with TGF-beta mRNA, preferably TGF-beta1, TGF-beta2, or TGF-beta3, alternatively, TGF-beta1, TGF-beta2, and/or TGF-beta3 mRNAs, i.e., TGF-beta1 and TGF-beta2, or TGF-beta1 and TGF-beta3, or TGF-beta2 and TGF-beta3, or TGF-beta1, TGF-beta2 and TGF-beta3 mRNAs, or any other direct or indirect effect on the TGF-beta system.

Preferably two or more oligonucleotides are combined, wherein at least one oligonucleotide specifically inhibits TGF-beta1 and at least one oligonucleotide specifically inhibits TGF-beta2, or wherein at least one oligonucleotide specifically inhibits TGF-beta1 and at least one oligonucleotide specifically inhibits TGF-beta3, or wherein at least one oligonucleotide specifically inhibits TGF-beta2 and at least one oligonucleotide specifically inhibits TGF-beta3, or wherein at least one oligonucleotide specifically inhibits TGF-beta1, at least one oligonucleotide specifically inhibits TGF-beta2, and at least one oligonucleotide specifically inhibits TGF-beta3.

In another embodiment, one oligonucleotide inhibits two TGF-beta isoforms such as TGF-beta1 and TGF-beta2, TGF-beta2 and TGF-beta3, or TGF-beta1 and TGF-beta3.

An oligonucleotide inhibiting the expression of all three isoforms—TGF-beta1, TGF-beta2, and TGF-beta3—is defined as pan-specific oligonucleotide.

In a further embodiment three or more oligonucleotides are combined, wherein at least one oligonucleotide specifically inhibits TGF-beta1, another oligonucleotide specifically inhibits TGF-beta2, and a further oligonucleotide specifically inhibits TGF-beta3, and optionally one or more additional oligonucleotides inhibiting TGF-beta1, TGF-beta2 or TGF-beta3.

The oligonucleotides of the present invention have for example an $IC_{50}$ in the range of 0.1 to 20 µM, preferably in the range of 0.2 to 15 µM, more preferably in the range of 0.4 to 10 µM, and even more preferred in the range of 0.5 to 5 µM.

The present invention further refers to a pharmaceutical composition comprising an oligonucleotide according to the invention as active ingredient. The pharmaceutical composition comprises at least one oligonucleotide of the present invention and optionally further an antisense compound, an antibody, a chemotherapeutic compound, an anti-inflammatory compound, an antiviral compound and/or an immunomodulating compound. Pharmaceutically acceptable binding agents and adjuvants or carrier optionally comprise part of the pharmaceutical composition.

In one embodiment, the oligonucleotide and the pharmaceutical composition, respectively, is formulated as dosage unit in form of capsules, tablets and pills etc., respectively, which contain for example the following compounds: microcrystalline cellulose, gum or gelatin as binders; starch or lactose as excipients; stearates as lubricants, various sweetening or flavouring agents. For capsules the dosage unit may contain a liquid carrier like fatty oils. Likewise coatings of sugar or enteric agents may be part of the dosage unit.

The oligonucleotide and/or the pharmaceutical composition is administrable via different routes. These routes of administration include, but are not limited to, electroporation, epidermal, impression into skin, intra-arterial, intra-articular, intracranial, intradermal, intra-lesional, intra-muscular, intranasal, intra-ocular, intrathecal, intracameral, intraperitoneal, intraprostatic, intrapulmonary, intraspinal, intratracheal, intratumoral, intravenous, intravesical, placement within cavities of the body, nasal inhalation, oral, pulmonary inhalation (e.g., by inhalation or insufflation of powders or aerosols, including by nebulizer), subcutaneous, subdermal, topical (including ophthalmic and to mucous membranes including vaginal and rectal delivery), or transdermal administration.

For parenteral, subcutaneous, intradermal or topical administration the oligonucleotide and/or the pharmaceutical composition include for example a sterile diluent, buffers, regulators of toxicity and antibacterials. In a preferred embodiment, the oligonucleotide or pharmaceutical composition is prepared with carriers that protect against degradation or immediate elimination from the body, including implants or microcapsules with controlled release properties. For intravenous administration the preferred carriers are for example physiological saline or phosphate buffered saline. An oligonucleotide and/or a pharmaceutical composition comprising such oligonucleotide for oral administration includes for example powder or granule, microparticulate, nanoparticulate, suspension or solution in water or non-aqueous media, capsule, gel capsule, sachet, tablet or minitablet. An oligonucleotide and/or a pharmaceutical composition comprising for parenteral, intrathecal, intracameral or intraventricular administration includes for example sterile aqueous solutions which optionally contain buffer, diluent and/or other suitable additive such as penetration enhancer, carrier compound and/or other pharmaceutically acceptable carrier or excipient.

A pharmaceutically acceptable carrier is for example liquid or solid, and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, a binding agent (e.g. pregelatinized maize starch, polyvinylpyrrolidone or hydroxypropyl methylcellulose, etc.); filler (e.g. lactose and other sugars, microcrystalline cellulose, pectin, gelatin, calcium sulfate, ethyl cellulose, polyacrylates or calcium hydrogen phosphate, etc.); lubricant (e.g., magnesium stearate, talcum, silica, colloidal silicon dioxide, stearic acid, metallic stearates, hydrogenated vegetable oils, corn starch, polyethylene glycols, sodium benzoate, sodium acetate, etc.); disintegrate (e.g., starch, sodium starch glycolate, etc.); or wetting agent (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404. An adjuvant is included under these phrases.

Beside being used in a method of human disease prevention and/or treatment, the oligonucleotide and/or the pharmaceutical composition according to the present invention is also used in a method for prevention and/or treatment of other subjects including veterinary animals, reptiles, birds, exotic animals and farm animals, including mammals, rodents, and the like. Mammals include for example horses, dogs, pigs, cats, or primates (for example, a monkey, a chimpanzee, or a lemur). Rodents include for example rats, rabbits, mice, squirrels, or guinea pigs.

The oligonucleotide or the pharmaceutical composition according to the invention is used in a method for the prevention and/or treatment of many different diseases, preferably benign or malignant tumors, immunologic diseases, bronchial asthma, heart disease, fibrosis (e.g., liver fibrosis, idiopathic pulmonary fibrosis, liver cirrhosis, kidney cirrhosis, scleroderma), diabetes, wound healing, disorders of the connective tissue (e.g., in heart, blood vessel, bone, joint, eye such as the Marfan or Loeys-Dietz syndrome), psoriasis, eye diseases (e.g., glaucoma, posterior capsular opacification (PCO) also known as secondary cataract), CNS disease (e.g., Alzheimer's disease, Parkinson's disease), coronary atherosclerosis (coronary intervention or coronary artery bypass graft (CABG) surgery or hair loss. A tumor is for example selected from the group of solid tumors, blood born tumors, leukemias, tumor metastasis, hemangiomas, acoustic neuromas, neurofibromas, trachomas, pyogenic granulomas, astrocytoma such as anaplastic astrocytoma, acoustic neuroma, blastoma, Ewing's tumor, craniopharyngloma, ependymoma, medulloblastoma, glioma, glioblastoma, hemangloblastoma, Hodgkins-lymphoma, medullablastoma, leukaemia, melanoma such as primary and/or metastatic melanoma, mesothelioma, myeloma, neuroblastoma, neurofibroma, non-Hodgkins lymphoma, pinealoma, retinoblastoma, sarcoma, seminoma, trachomas, Wilm's tumor, bile duct carcinoma, bladder carcinoma, brain tumor, breast cancer, bronchogenic carcinoma, carcinoma of the kidney, cervical cancer, choriocarcinoma, choroidcarcinoma, cystadenocarcinome, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma (RCC, e.g., clear cell RCC, papillary RCC, chromophobe RCC), oncocytoma kidney cancer, transitional cell kidney cancer, retinoblastoma, skin cancer, small-cell bronchogenic/lung carcinoma, squamous cell carcinoma, sebaceous gland carcinoma, testicular carcinoma, and uterine cancer. The oligonucleotide or the pharmaceutical composition of the present invention is not only used in a method for the prevention and/or treatment of a tumor, but likewise on a metastasis.

The antisense oligonucleotides of the present invention are characterized in that they show an unexpected low toxicity (see for example Table 5) and thus, are well tolerated by different organisms. They oligonucleotides show a reasonable distribution in the organism, wherein highest concentrations are measured in the kidney, liver, skin and spleen.

The present invention provides numerous oligonucleotides, which are highly efficient in the reduction and inhibition, respectively, of TGF-beta, in particular TGF-beta1, TGF-beta2 and/or TGF-beta3 expression due to the specific selection of the sequence of the oligonucleotide and the modification of the nucleotide. The following Table 1 shows numerous preferred modified oligonucleotides according to the present invention (bold letters indicate the modified nucleoside). Each oligonucleotides is defined as ASPH and a number, which is defined by a specific sequence and modification of the nucleosides:

| SEQ ID NO. | Sequence (5'->3') | Modification | ASPH |
|---|---|---|---|
| 2 | GACCAGATGCAGGA | LNA 3 + 3 | 36 |
| 3 | GCGACCGTGACCAGAT | LNA 3 + 3 | 80 |
| 4 | GCGCGACCGTGACC | LNA 3 + 3 | 98 |
| 5 | AGCGCGACCGTGA | LNA 2 + 3 | 111 |
| 6 | GACCGTGACCAGAT | LNA 2 + 2 | 121 |
| 6 | GACCGTGACCAGAT | LNA 3 + TEG | 153 |
| 7 | CTGCCCGCGGAT | LNA 2 + 2 | 15 |
| 8 | TCTGCCCGCGGAT | LNA 3 + 2 | 17 |
| 9 | GGATCTGCCCGCGGA | LNA 4 + 3 | 26 |
| 9 | GGATCTGCCCGCGGA | LNA 3 + 4 | 27 |
| 10 | CTTGCTCAGGATCTGCC | LNA 4 + 4 | 37 |
| 11 | GCTCAGGATCTGCCCGCGGA | 2' O-meth 4 + 4 | 52 |
| 11 | GCTCAGGATCTGCCCGCGGA | 2' fluoro 4 + 4 | 53 |
| 12 | GGATCGCCTCGAT | LNA 3 + 2 | 112 |
| 13 | CCGCGGATCGCC | LNA 2 + 2 | 119 |
| 14 | ACCTCCTTGGCGTAGTA | LNA 3 + 3 | 01 |
| 14 | ACCTCCTTGGCGTAGTA | LNA 4 + 4 | 02 |
| 15 | CCTCCTTGGCGTAGTA | LNA 3 + 3 | 03 |
| 15 | CCTCCTTGGCGTAGTA | LNA 4 + 4 | 04 |
| 16 | CTCCTTGGCGTAGTA | LNA 3 + 3 | 05 |
| 16 | CTCCTTGGCGTAGTA | LNA 4 + 3 | 06 |
| 16 | CTCCTTGGCGTAGTA | LNA 3 + 4 | 07 |

-continued

| SEQ ID NO. | Sequence (5'->3') | Modification | ASPH |
|---|---|---|---|
| 17 | TCCTTGGCGTAGTA | LNA 3 + 3 | 08 |
| 18 | CAGAAGTTGGCAT | LNA 3 + 2 | 09 |
| 18 | CAGAAGTTGGCAT | LNA 2 + 3 | 10 |
| 19 | AAGTGGGCGGGAT | | 11 |
| 19 | AAGTGGGCGGGAT | LNA 4 + 4 | 12 |
| 19 | AAGTGGGCGGGAT | 2' O-meth 4 + 4 | 13 |
| 19 | AAGTGGGCGGGAT | 2' fluoro 4 + 4 | 14 |
| 20 | GCGGGATGGCAT | LNA 2 + 2 | 16 |
| 21 | GAAATCACCTCCG | LNA 2 + 3 | 18 |
| 22 | AAGTGGGCGGGAT | LNA 2 + 3 | 19 |
| 23 | TGTAGCGCTGGGT | LNA 2 + 3 | 20 |
| 24 | CGAAGGAGAGCCA | LNA 3 + 2 | 21 |
| 25 | TCGCGCTCGCAGGC | LNA 3 + 3 | 22 |
| 26 | AAGTGGGCGGGATG | LNA 3 + 3 | 23 |
| 27 | ATGTAGCGCTGGGT | LNA 3 + 3 | 24 |
| 28 | CGAAGGAGAGCCAT | LNA 3 + 3 | 25 |
| 29 | GAAAGTGGGCGGGAT | LNA 4 + 3 | 28 |
| 30 | CGAAGGAGAGCCATT | LNA 4 + 3 | 29 |
| 31 | CGATCCTCTTGCGCAT | LNA 4 + 4 | 30 |
| 32 | AAGTGGGCGGGATGGC | LNA 4 + 4 | 31 |
| 33 | GATGGAAATCACCTCCG | LNA 4 + 4 | 32 |
| 34 | AAACCTCCTTGGCGTAG | LNA 4 + 4 | 33 |
| 35 | TAGAAAGTGGGCGGGAT | LNA 4 + 4 | 34 |
| 36 | GGCGGGATGGCAT | LNA 2 + 3 | 35 |
| 37 | GGGTCTGTAGAAAGTG | LNA 4 + 4 | 38 |
| 38 | GAAGGAGAGCCATTC | LNA 3 + 4 | 39 |
| 39 | CCAGGTTCCTGTCTT | LNA 3 + 4 | 40 |
| 40 | TCTGATCACCACTGG | LNA 3 + 4 | 41 |
| 41 | TTTCTGATCACCACTGG | LNA 4 + 4 | 42 |
| 42 | GTCTGTAGGAGGGCA | LNA 4 + 3 | 43 |
| 43 | AGTCTGTAGGAGGGCA | LNA 4 + 4 | 44 |
| 44 | TCTGTAGGAGGGC | LNA 2 + 3 | 45 |
| 45 | CAGATGCCAGTTTTAAC | LNA 4 + 4 | 46 |
| 46 | CAAAGTATTTGGTCTCC | LNA 4 + 4 | 47 |
| 47 | CCTTAAGCCATCCATGA | LNA 4 + 4 | 48 |
| 48 | GTACTGGCCAGCTAA | LNA 4 + 3 | 49 |
| 49 | GCCTCGATCCTCTTGCGCAT | 2' O-meth 4 + 4 | 50 |
| 49 | GCCTCGATCCTCTTGCGCAT | 2' fluoro 4 + 4 | 51 |
| 50 | AAACCTCCTTGGCGTAGTAC | 2' O-meth 4 + 4 | 54 |
| 50 | AAACCTCCTTGGCGTAGTAC | 2' fluoro 4 + 4 | 55 |
| 51 | GAAAGTGGGCGGGATGGCAT | 2' O-meth 4 + 4 | 56 |
| 51 | GAAAGTGGGCGGGATGGCAT | 2' fluoro 4 + 4 | 57 |
| 52 | GAATTGCTCGCTTAGGG | LNA 3 + 3 | 60 |
| 53 | CGTCGCGGTTGCGTTCA | LNA 3 + 3 | 61 |
| 54 | CGTGGCCTACACCCTGG | LNA 3 + 3 | 62 |
| 55 | TTCTAAAGCAATAGGCC | LNA 3 + 3 | 63 |
| 56 | AGAATGGTTAGAGGTTC | LNA 3 + 3 | 64 |
| 57 | TCTGAACTAGTACCGCC | LNA 3 + 3 | 65 |
| 58 | CCCATTAATATGACCTC | LNA 3 + 3 | 66 |
| 59 | TTTAGTTAGAACCCTAA | LNA 3 + 3 | 67 |
| 60 | CCTCAGATATAGATAAC | LNA 3 + 3 | 68 |
| 61 | TACTATTATGGCATCCC | LNA 3 + 3 | 69 |
| 62 | TGCCCACTTGCATACTA | LNA 3 + 3 | 70 |
| 63 | AGCGTAATTGGTCATCA | LNA 3 + 3 | 71 |
| 64 | CGTTGGCAGAACATAGA | LNA 3 + 3 | 72 |
| 65 | GGGATACTGTCTAGACC | LNA 3 + 3 | 73 |
| 66 | ATTGGCAACTCGTTTGA | LNA 3 + 3 | 74 |
| 67 | CGTCAGGCTAATATTC | LNA 3 + 3 | 75 |
| 68 | GGATGACTCCCTAGAC | LNA 3 + 3 | 76 |
| 69 | GTCGCGGTTGCGTTCA | LNA 3 + 3 | 77 |
| 70 | CTCGGTACTCGGTCGG | LNA 3 + 3 | 78 |
| 71 | GGTTCGGTCCTGCCTT | LNA 3 + 3 | 79 |
| 72 | AATAGGCCGCATCCAA | LNA 3 + 3 | 81 |
| 73 | AACTAGTACCGCCTTT | LNA 3 + 3 | 82 |
| 74 | TCGGTCATATAATAAC | LNA 3 + 3 | 83 |
| 75 | AGACCGTCAGGCTAA | LNA 3 + 3 | 84 |
| 76 | GTCGCGGTTGCGTTC | LNA 3 + 3 | 85 |
| 77 | TTCCACTGCGGCGCT | LNA 3 + 3 | 86 |
| 78 | AAGGAGCGGTTCGGT | LNA 3 + 3 | 87 |
| 79 | CTCGGGTGCGGAGTG | LNA 3 + 3 | 88 |
| 80 | CTGACTTTGGCGAGT | LNA 3 + 3 | 89 |
| 81 | GATAGGAACGGTACG | LNA 3 + 3 | 90 |
| 82 | CACTTTGGATTCCCG | LNA 3 + 3 | 91 |
| 83 | GTCGCGGTTGCGTT | LNA 3 + 3 | 92 |
| 84 | TACACCCTGGCGGG | LNA 3 + 3 | 93 |

-continued

| SEQ ID NO. | Sequence (5'->3') | Modification | ASPH |
|---|---|---|---|
| 85 | CTCGGTACTCGGTC | LNA 3 + 3 | 94 |
| 86 | AGGAGCGGTTCGGT | LNA 3 + 3 | 95 |
| 87 | GTCTCGGGTGCGGA | LNA 3 + 3 | 96 |
| 88 | TACGGGACGGGCAG | LNA 3 + 3 | 97 |
| 89 | CGTCGCTCCTCTCG | LNA 3 + 3 | 99 |
| 90 | TAGCGCTGGGTTGG | LNA 3 + 3 | 100 |
| 91 | AAGCAATAGGCCGC | LNA 3 + 3 | 101 |
| 92 | TACGGGCATGCTCC | LNA 3 + 3 | 102 |
| 93 | AGGCGCGGGATAGG | LNA 3 + 3 | 103 |
| 94 | TTTGGATTCCCGCC | LNA 3 + 3 | 104 |
| 95 | ACCACTAGAGCACC | LNA 3 + 3 | 105 |
| 96 | GCGTTGGCAGAACA | LNA 3 + 3 | 106 |
| 97 | TTGCTCGCTTAGG | LNA 2 + 3 | 107 |
| 98 | GTCGCGGTTGCGT | LNA 3 + 2 | 108 |
| 99 | GGCGCTCGGTACT | LNA 2 + 3 | 109 |
| 100 | ATCTGAACTCGGC | LNA 3 + 2 | 110 |
| 101 | CGGTTGGTCTGTT | LNA 2 + 3 | 113 |
| 102 | TCCACCCTAGATC | LNA 2 + 3 | 114 |
| 103 | CTAGTACCGCCTT | LNA 2 + 3 | 115 |
| 104 | GGTCGGCAGTCAA | LNA 3 + 2 | 116 |
| 105 | CTTGCGACACCC | LNA 2 + 2 | 117 |
| 106 | GAGCGGTTCGGT | LNA 2 + 2 | 118 |
| 107 | ACACAGTAGTGCAT | LNA 2 + 2 | 120 |
| 108 | GGGTCTGTAGAAAG | LNA 2 + 2 | 122 |
| 108 | GGGTCTGTAGAAAG | LNA 3 + TEG | 154 |
| 109 | GGTTGGAGATGTTA | LNA 2 + 2 | 123 |
| 109 | GGTTGGAGATGTTA | LNA 3 + TEG | 155 |
| 110 | TGGGTTGGAGATGT | LNA 2 + 2 | 124 |
| 110 | TGGGTTGGAGATGT | LNA 3 + TEG | 156 |
| 111 | GCTGGGTTGGAGAT | LNA 2 + 2 | 125 |
| 111 | GCTGGGTTGGAGAT | LNA 3 + TEG | 157 |
| 112 | GCGCTGGGTTGGAG | LNA 2 + 2 | 126 |
| 112 | GCGCTGGGTTGGAG | LNA 3 + TEG | 158 |
| 113 | AGCGCTGGGTTGGA | LNA 2 + 2 | 127 |
| 113 | AGCGCTGGGTTGGA | LNA 3 + TEG | 159 |
| 114 | TAGCGCTGGGTTGG | LNA 2 + 2 | 128 |
| 114 | TAGCGCTGGGTTGG | LNA 3 + TEG | 160 |
| 115 | GTAGCGCTGGGTTG | LNA 2 + 2 | 129 |
| 115 | GTAGCGCTGGGTTG | LNA 3 + TEG | 161 |
| 116 | GATGTAGCGCTGGG | LNA 2 + 2 | 130 |
| 116 | GATGTAGCGCTGGG | LNA 3 + TEG | 162 |
| 117 | CCATTCGCCTTCTG | LNA 2 + 2 | 131 |
| 117 | CCATTCGCCTTCTG | LNA 3 + TEG | 163 |
| 118 | GAGAGCCATTCGCC | LNA 2 + 2 | 132 |
| 118 | GAGAGCCATTCGCC | LNA 3 + TEG | 164 |
| 119 | AGCAGGGACAGTGT | LNA 2 + 2 | 133 |
| 119 | AGCAGGGACAGTGT | LNA 3 + TEG | 165 |
| 120 | GCAGGAGATGTGGG | LNA 2 + 2 | 134 |
| 120 | GCAGGAGATGTGGG | LNA 3 + TEG | 166 |
| 121 | CGGTTGGTCTGTTG | LNA 2 + 2 | 135 |
| 121 | CGGTTGGTCTGTTG | LNA 3 + TEG | 167 |
| 122 | CCGGTTGGTCTGTT | LNA 2 + 2 | 136 |
| 122 | CCGGTTGGTCTGTT | LNA 3 + TEG | 168 |
| 123 | GCCGGTTGGTCTGT | LNA 2 + 2 | 137 |
| 123 | GCCGGTTGGTCTGT | LNA 3 + TEG | 169 |
| 124 | AGTTGGCATTGTAC | LNA 2 + 2 | 138 |
| 124 | AGTTGGCATTGTAC | LNA 3 + TEG | 170 |
| 125 | GGTTAGAGGTTCTA | LNA 2 + 2 | 139 |
| 125 | GGTTAGAGGTTCTA | LNA 3 + TEG | 171 |
| 126 | ATGGTTAGAGGTTC | LNA 2 + 2 | 140 |
| 126 | ATGGTTAGAGGTTC | LNA 3 + TEG | 172 |
| 127 | AGAATGGTTAGAGG | LNA 2 + 2 | 141 |
| 127 | AGAATGGTTAGAGG | LNA 3 + TEG | 173 |
| 128 | AGAGAATGGTTAGA | LNA 2 + 2 | 142 |
| 128 | AGAGAATGGTTAGA | LNA 3 + TEG | 174 |
| 129 | CGTTGTCGTCGTCA | LNA 2 + 2 | 143 |
| 129 | CGTTGTCGTCGTCA | LNA 3 + TEG | 175 |
| 130 | ACCAAGGCTCTCTT | LNA 2 + 2 | 144 |
| 130 | ACCAAGGCTCTCTT | LNA 3 + TEG | 176 |
| 131 | GCTTCTTGTCTCTC | LNA 2 + 2 | 145 |
| 131 | GCTTCTTGTCTCTC | LNA 3 + TEG | 177 |
| 132 | GGAACGGTACGTAC | LNA 2 + 2 | 146 |
| 132 | GGAACGGTACGTAC | LNA 3 + TEG | 178 |
| 133 | TAGGAACGGTACGT | LNA 2 + 2 | 147 |
| 133 | TAGGAACGGTACGT | LNA 3 + TEG | 179 |

| SEQ ID NO. | Sequence (5'->3') | Modification | ASPH |
|---|---|---|---|
| 134 | GGGATAGGAACGGT | LNA 2 + 2 | 148 |
| 134 | GGGATAGGAACGGT | LNA 3 + TEG | 180 |
| 135 | CGCGGGATAGGAAC | LNA 2 + 2 | 149 |
| 135 | CGCGGGATAGGAAC | LNA 3 + TEG | 181 |
| 136 | AGGCGCGGGATAGG | LNA 2 + 2 | 150 |
| 136 | AGGCGCGGGATAGG | LNA 3 + TEG | 182 |
| 137 | GTCAAGCTGGATGG | LNA 2 + 2 | 151 |
| 137 | GTCAAGCTGGATGG | LNA 3 + TEG | 183 |
| 138 | TCTGTAGGAGGGC | ENA 2 + 3 | 184 |
| 139 | GACCAGATGCAGGA | ENA 3 + 3 | 185 |
| 140 | CTCCTTGGCGTAGTA | ENA 3 + 3 | 186 |
| 141 | CCTCCTTGGCGTAGTA | ENA 3 + 3 | 187 |
| 142 | CAGATGCCAGTTTTAAC | ENA 4 + 4 | 188 |
| 143 | AGCGTAATTGGTCATCA | ENA 3 + 3 | 189 |
| 146 | AGTATTTGGTCTCC | LNA 3 + 3 | 190 |
| 147 | AAGTATTTGGTCTC | LNA 3 + 3 | 191 |
| 148 | AAGTATTTGGTCTCC | LNA 3 + 3 | 192 |
| 149 | CAAAGTATTTGGTCTCC | LNA 3 + 3 | 193 |
| 150 | AGCTCGTCCCTCCTCCC | LNA 3 + 3 | 1000 |
| 151 | GAGGGCTGGTCCGGAAT | LNA 3 + 3 | 1001 |
| 152 | CGAGGGCTGGTCCGAA | LNA 3 + 3 | 1002 |
| 153 | GAGGGCGGCATGGGGA | LNA 3 + 3 | 1003 |
| 154 | GCGGGTGCTGTTGTACA | LNA 3 + 3 | 1004 |
| 155 | CGCGGGTGCTGTTGTAC | LNA 3 + 3 | 1005 |
| 156 | GTCGCGGGTGCTGTTGT | LNA 3 + 3 | 1006 |
| 157 | GGTCGCGGGTGCTGTTG | LNA 3 + 3 | 1007 |
| 158 | CCGGTCGCGGGTGCTGT | LNA 3 + 3 | 1008 |
| 159 | CCCGGTCGCGGGTGCTG | LNA 3 + 3 | 1009 |
| 160 | AGCACGCGGGTGACCTC | LNA 3 + 3 | 1010 |
| 161 | TTAGCACGCGGGTGACC | LNA 3 + 3 | 1011 |
| 162 | GGGCTCGTGGATCCACT | LNA 3 + 3 | 1012 |
| 163 | CCTTGGGCTCGTGGATC | LNA 3 + 3 | 1013 |
| 164 | TGGCATGGTAGCCCTTG | LNA 3 + 3 | 1014 |
| 165 | CGAGGGCTGGTCCGGA | LNA 3 + 3 | 1015 |
| 166 | GCGGGTGCTGTTGTAC | LNA 3 + 3 | 1016 |
| 167 | GCACGCGGGTGACCTC | LNA 3 + 3 | 1017 |
| 168 | CCTTGGGCTCGTGGAT | LNA 3 + 3 | 1018 |
| 169 | GGCATGGTAGCCCTTG | LNA 3 + 3 | 1019 |
| 170 | GGGTGCTGTTGTAC | LNA 3 + 3 | 1020 |
| 171 | TCGCGGGTGCTGTT | LNA 3 + 3 | 1021 |
| 172 | GTCGCGGGTGCTGT | LNA 3 + 3 | 1022 |
| 173 | CTCGTGGATCCACT | LNA 3 + 3 | 1023 |
| 174 | ATGGTAGCCCTTGG | LNA 3 + 3 | 1024 |
| 175 | TGGCATGGTAGCCC | LNA 3 + 3 | 1025 |
| 176 | GAAGTTGGCATGGT | LNA 3 + 3 | 1026 |
| 177 | TCGCGGGTGCTGT | LNA 2 + 3 | 1027 |
| 178 | CACCCGGTCGCGG | LNA 2 + 3 | 1028 |
| 179 | CCACCCGGTCGCGC | LNA 2 + 3 | 1029 |
| 180 | CGCCAGGAATTGT | LNA 3 + 2 | 1030 |
| 181 | GGCTCGTGGATCC | LNA 2 + 3 | 1031 |
| 182 | TGGGCTCGTGGAT | LNA 2 + 3 | 1032 |
| 183 | GCATGGTAGCCCT | LNA 2 + 3 | 1033 |
| 184 | AGTTGGCATGGTA | LNA 2 + 3 | 1034 |
| 185 | TTGCAGGAGCGCA | LNA 2 + 3 | 1035 |
| 186 | ATTAGCACGCGGGTGAC | LNA 3 + 3 | 1036 |
| 187 | ACCATTAGCACGCGGT | LNA 3 + 3 | 1037 |
| 188 | CACCATTAGCACGCGG | LNA 3 + 3 | 1038 |
| 189 | CCACCATTAGCACGCGG | LNA 3 + 3 | 1039 |
| 190 | TCCACCATTAGCACGCG | LNA 3 + 3 | 1040 |
| 191 | TCCACCTTGGGCTTGCG | LNA 3 + 3 | 1041 |
| 192 | TTAGCACGCGGGTGAC | LNA 3 + 3 | 1042 |
| 193 | ACCATTAGCACGCGGG | LNA 3 + 3 | 1043 |
| 194 | CACCATTAGCACGCGG | LNA 3 + 3 | 1044 |
| 195 | CACCATTAGCACGCGC | LNA 3 + 3 | 1045 |
| 196 | GCGGCACGCAGCACG | LNA 3 + 3 | 1046 |
| 197 | TCGATGCGCTTCCG | LNA 3 + 3 | 1047 |
| 198 | TAGCACGCGGGTGA | LNA 3 + 3 | 1048 |
| 199 | ATTAGCACGCGGGT | LNA 3 + 3 | 1049 |
| 200 | CATTAGCACGCGGG | LNA 3 + 3 | 1050 |
| 201 | ACCATTAGCACGCG | LNA 3 + 3 | 1051 |
| 202 | CACCATTAGCACGC | LNA 3 + 3 | 1052 |
| 203 | CCACCATTAGCACG | LNA 3 + 3 | 1053 |
| 204 | TCCACCATTAGCAC | LNA 3 + 3 | 1054 |
| 205 | GACCTTGCTGTACT | LNA 3 + 3 | 1055 |
| 206 | GGACCTTGCTGTTAC | LNA 3 + 3 | 1056 |

| SEQ ID NO. | Sequence (5'->3') | Modification | ASPH |
|---|---|---|---|
| 207 | AGGACCTTGCTGTA | LNA 3 + 3 | 1057 |
| 208 | CGGCACGCAGCACG | LNA 3 + 3 | 1058 |
| 209 | ACCTTGGGCTTGCG | LNA 3 + 3 | 1059 |
| 210 | TTAGCACGCGGGT | LNA 3 + 2 | 1060 |
| 211 | ACCATTAGCACGC | LNA 3 + 2 | 1061 |
| 212 | CGGCACGCAGCAC | LNA 3 + 2 | 1062 |
| 213 | CACCAGCTCCATGTCGA | LNA 3 + 3 | 1063 |
| 214 | TCGCGGGTGCTGTTGTA | LNA 3 + 3 | 1064 |
| 215 | GTGTCCAGGCTCCAAAT | LNA 3 + 3 | 1065 |
| 215 | GTGTCCAGGCTCCAAAT | LNA 4 + 2 | 1066 |
| 216 | GCTCGTCCCTCCTCCC | LNA 3 + 3 | 1067 |
| 217 | ACCAGCTCGTCCCTCC | LNA 3 + 3 | 1068 |
| 218 | GGAGGCCCCGCCCCTG | LNA 3 + 3 | 1069 |
| 219 | CATGGGGAGGCGGCG | LNA 3 + 3 | 1070 |
| 219 | CATGGGGAGGCGGCG | 3LNA + 9N + 1LNA + 1N + 2LNA | 1071 |
| 220 | ACCAGCTCCATGTCGA | LNA 3 + 3 | 1072 |
| 221 | GGTCGCGGGTGCTGTT | LNA 3 + 3 | 1073 |
| 222 | GGACCTTGCTGTACTG | LNA 3 + 3 | 1074 |
| 222 | GGACCTTGCTGTACTG | LNA 4 + 2 | 1075 |
| 223 | TCCACCTTGGGCTTGC | LNA 3 + 3 | 1076 |
| 224 | AGCTCGTCCCTCCTC | LNA 3 + 3 | 1077 |
| 225 | CCAGCTCGTCCCTCC | LNA 3 + 3 | 1078 |
| 226 | GAGGGCTGGTCCGGA | LNA 3 + 3 | 1079 |
| 227 | TCCCGAGGGCTGGTC | LNA 3 + 3 | 1080 |
| 228 | CGGCATGGGGAGGC | LNA 2 + 4 | 1081 |
| 229 | CAGCTCCATGTCGAT | LNA 3 + 3 | 1082 |
| 230 | ACCAGCTCCATGTCG | LNA 3 + 3 | 1083 |
| 231 | TCGCGGGTGCTGTTG | LNA 3 + 3 | 1084 |
| 232 | GTCGCGGGTGCTGTT | LNA 3 + 3 | 1085 |
| 233 | GGTCGCGGGTGCTGT | LNA 3 + 3 | 1086 |
| 234 | AGCACGCGGGTGACC | LNA 3 + 3 | 1087 |
| 235 | TAGCACGCGGGTGAC | LNA 3 + 3 | 1088 |
| 236 | CATTAGCACGCGGGT | LNA 3 + 3 | 1089 |
| 237 | TCCACCATTAGCACG | LNA 3 + 3 | 1090 |
| 238 | CCAGGAATTGTTGCT | LNA 4 + 2 | 1091 |
| 239 | TTGGGCTCGTGGATC | LNA 3 + 3 | 1092 |
| 240 | CTTGGGCTCGTGGAT | LNA 3 + 3 | 1093 |
| 241 | TTGGCATGGTAGCCC | LNA 3 + 3 | 1094 |
| 242 | GAAGTTGGCATGGTA | LNA 3 + 3 | 1095 |
| 243 | AGAAGTTGGCATGGT | LNA 3 + 3 | 1096 |
| 244 | TGTCCAGGCTCCAAA | LNA 4 + 2 | 1097 |
| 245 | AGGACCTTGCTGTAC | LNA 3 + 3 | 1098 |
| 246 | CACCTTGGGCTTGCG | LNA 4 + 2 | 1099 |
| 246 | CACCTTGGGCTTGCG | 1LNA + 1N + 2LNA + 8N + 1LNA + 1N + 1LNA | 1100 |
| 247 | AGCTCGTCCCTCCT | LNA 3 + 3 | 1101 |
| 248 | CAGCTCGTCCCTCC | LNA 3 + 3 | 1102 |
| 249 | ACCAGCTCGTCCCT | LNA 3 + 3 | 1103 |
| 250 | CCCGAGGGCTGGTC | LNA 3 + 3 | 1104 |
| 251 | GCGGCATGGGGAG | LNA 2 + 4 | 1105 |
| 252 | GTCTTGCAGGTGGA | LNA 3 + 3 | 1106 |
| 253 | TCGATGCGCTTCCG | LNA 2 + 4 | 1107 |
| 253 | TCGATGCGCTTCCG | LNA 2 + 3 | 1108 |
| 253 | TCGATGCGCTTCCG | 2LNA + 8N + 2LNA + 1N + 1LNA | 1109 |
| 253 | TCGATGCGCTTCCG | 2LNA + 9N + 1LNA + 1N + 1LNA | 1110 |
| 253 | TCGATGCGCTTCCG | 2LNA + 8N + 1LNA + 2N + 1LNA | 1111 |
| 254 | GGACAGGATCTGGC | LNA 4 + 2 | 1112 |
| 255 | ACCTCCCCCTGGCT | LNA 3 + 3 | 1113 |
| 256 | ACCATTAGCACGCG | LNA 4 + 2 | 1114 |
| 256 | ACCATTAGCACGCG | 3LNA + 8N + 1LNA + 1N + 1LNA | 1115 |
| 257 | CAGCAGTTCTTCTC | LNA 2 + 4 | 1116 |
| 258 | TACAGCTGCCGCAC | LNA 3 + 3 | 1117 |
| 259 | AGTTGGCATGGTAG | LNA 3 + 3 | 1118 |
| 259 | AGTTGGCATGGTAG | LNA 4 + 2 | 1119 |
| 260 | AAGTTGGCATGGTA | LNA 3 + 3 | 1120 |
| 261 | GAAGTTGGCATGGT | LNA 4 + 2 | 1121 |
| 262 | TCCAGGCTCCAAAT | LNA 3 + 3 | 1122 |
| 263 | ACCTTGCTGTACTG | LNA 3 + 3 | 1123 |
| 263 | ACCTTGGGCTTGCG | LNA 4 + 2 | 1124 |
| 263 | ACCTTGGGCTTGCG | LNA 3 + 2 | 1125 |
| 263 | ACCTTGGGCTTGCG | 3LNA + 8N + 1LNA + 1N + 1LNA | 1126 |

| SEQ ID NO. | Sequence (5'->3') | Modification | ASPH |
|---|---|---|---|
| 263 | ACCTTGGGCTTGCG | 2LNA + 9N + 1LNA + 1N + 1LNA | 1127 |
| 263 | ACCTTGGGCTTGCG | 2LNA + 8N + 2LNA + 1N + 1LNA | 1128 |
| 264 | TTGCAGGAGCGCAC | LNA 3 + 3 | 1129 |
| 265 | GCAGAAGTTGGCAT | LNA 4 + 2 | 1130 |
| 266 | CGGGTGCTGTTGTA | LNA 3 + 3 | 1131 |
| 266 | CGGGTGCTGTTGTA | LNA 2 + 4 | 1132 |
| 267 | CCCAGCGGCAACGGAAA | LNA 3 + 3 | 1133 |
| 268 | CAAGAGGTCCCCGCGCC | LNA 3 + 3 | 1134 |
| 269 | GCGTCCCCGGCGGCAAA | LNA 3 + 3 | 1135 |
| 270 | GGTCGGCGACTCCCGAG | LNA 3 + 3 | 1136 |
| 271 | TCGGAGAGAGATCCGTC | LNA 3 + 3 | 1137 |
| 272 | ATCCCACGGAAATAACC | LNA 3 + 3 | 1138 |
| 273 | CTCAGTATCCCACGGAA | LNA 3 + 3 | 1139 |
| 274 | ACTGCCGAGAGCGCGAA | LNA 3 + 3 | 1140 |
| 275 | CTGATGTGTTGAAGAAC | LNA 3 + 3 | 1141 |
| 276 | TGAGGTATCGCCAGGAA | LNA 3 + 3 | 1142 |
| 277 | ACTGCCGCACAACTCCG | LNA 3 + 3 | 1143 |
| 278 | CGGCCCACGTAGTACAC | LNA 3 + 3 | 1144 |
| 279 | CCCAGCGGCAACGGAA | LNA 3 + 3 | 1145 |
| 280 | TCGCGCCAAGAGGTCC | LNA 3 + 3 | 1146 |
| 281 | GGTCGGCGACTCCCGA | LNA 3 + 3 | 1147 |
| 282 | GTCGGAGAGAGATCCG | LNA 3 + 3 | 1148 |
| 283 | TCAGTATCCCACGGAA | LNA 3 + 3 | 1149 |
| 284 | CGAGAGCGCGAACAGG | LNA 3 + 3 | 1150 |
| 285 | ACTGCCGAGAGCGCGA | LNA 3 + 3 | 1151 |
| 286 | GGCGTCAGCACCAGTA | LNA 3 + 3 | 1152 |
| 287 | GGTTTCCACCATTAGC | LNA 3 + 3 | 1153 |
| 288 | GAGGTATCGCCAGGAA | LNA 3 + 3 | 1154 |
| 289 | AACCACTGCCGCACAA | LNA 3 + 3 | 1155 |
| 290 | CGGCCCACGTAGTACA | LNA 3 + 3 | 1156 |
| 291 | CGGCGGCTCGTCTCA | LNA 3 + 3 | 1157 |
| 292 | CCCAGCGGCAACGGA | LNA 3 + 3 | 1158 |
| 293 | TCGCGCCAAGAGGTC | LNA 3 + 3 | 1159 |
| 294 | CGTCGCGCCAAGAGG | LNA 3 + 3 | 1160 |
| 295 | GGAGCAAGCGTCCCC | LNA 3 + 3 | 1161 |
| 296 | GTGCGCCCGAGGTCT | LNA 3 + 3 | 1162 |
| 297 | GTCTAGGATGCGCGG | LNA 3 + 3 | 1163 |
| 298 | CAGTATCCCACGGAA | LNA 3 + 3 | 1164 |
| 299 | CCGAGAGCGCGAACA | LNA 3 + 3 | 1165 |
| 300 | GGCGTCAGCACCAGT | LNA 3 + 3 | 1166 |
| 301 | GTTGCTGAGGTATCG | LNA 3 + 3 | 1167 |
| 302 | ACCACTGCCGCACAA | LNA 3 + 3 | 1168 |
| 303 | CGGCCCACGTAGTAC | LNA 3 + 3 | 1169 |
| 304 | CTCGGCGACTCCTT | LNA 3 + 3 | 1170 |
| 305 | AGCGGCAACGGAAA | LNA 3 + 3 | 1171 |
| 306 | TCGCGCCAAGAGGT | LNA 3 + 3 | 1172 |
| 307 | TCCCCGGCGGCAAA | LNA 3 + 3 | 1173 |
| 308 | TGCGCCCGAGGTCT | LNA 3 + 3 | 1174 |
| 309 | GTCTAGGATGCGCG | LNA 3 + 3 | 1175 |
| 310 | GGTCGGAGAGAGAT | LNA 3 + 3 | 1176 |
| 311 | CACGGAAATAACCT | LNA 3 + 3 | 1177 |
| 312 | AGAGCGCGAACAGG | LNA 3 + 3 | 1178 |
| 313 | ATAGTCCCGCGGCC | LNA 3 + 3 | 1179 |
| 314 | TAGTAGTCGGCCTC | LNA 3 + 3 | 1180 |
| 315 | ATAGATTTCGTTGT | LNA 3 + 3 | 1181 |
| 316 | GAGGTATCGCCAGG | LNA 3 + 3 | 1182 |
| 317 | GCCGCACAACTCCG | LNA 3 + 3 | 1183 |
| 318 | TCGCGCCAAGAGG | LNA 2 + 3 | 1184 |
| 319 | AAGCGTCCCCGGC | LNA 3 + 2 | 1185 |
| 320 | GACGCCGTGTAGG | LNA 3 + 2 | 1186 |
| 321 | GTCGGCGACTCCC | LNA 2 + 3 | 1187 |
| 322 | TGCGCCCGAGGTC | LNA 3 + 2 | 1188 |
| 323 | GTCGGAGAGAGAT | LNA 3 + 2 | 1189 |
| 324 | TCCCACGGAAATA | LNA 3 + 2 | 1190 |
| 325 | TGCCGAGAGCGCG | LNA 2 + 3 | 1191 |
| 326 | TAGTCCCGCGGCC | LNA 3 + 2 | 1192 |
| 327 | TAGTAGTCGGCCT | LNA 3 + 2 | 1193 |
| 328 | CATAGATTTCGTT | LNA 2 + 3 | 1194 |
| 329 | TTTAACTTGAGCC | LNA 3 + 3 | 1195 |
| 330 | GAGGTATCGCCAG | LNA 3 + 2 | 1196 |
| 331 | ACTCCGGTGACAT | LNA 2 + 3 | 1197 |
| 332 | GCCCACGTAGTAC | LNA 3 + 3 | 1198 |
| 333 | TCGGCGACTCCC | LNA 2 + 2 | 1199 |
| 334 | GTCGGCGACTCC | LNA 2 + 2 | 1200 |

-continued

| SEQ ID NO. | Sequence (5'->3') | Modification | ASPH |
|---|---|---|---|
| 337 | CAGGAAGCGCTGGCAAC | LNA 3 + 3 | 2000 |
| 338 | GGTGCATGAACTCACTG | LNA 3 + 3 | 2001 |
| 339 | GTCCCCTAATGGCTTCC | LNA 3 + 3 | 2002 |
| 340 | ATCTGTCCCCTAATGGC | LNA 3 + 3 | 2003 |
| 341 | CCGGGTGCTGTTGTAAA | LNA 3 + 3 | 2004 |
| 342 | CCTGGATCATGTCGAAT | LNA 3 + 3 | 2005 |
| 343 | CCCTGGATCATGTCGAA | LNA 3 + 3 | 2006 |
| 344 | GTAGCACCTGCTTCCAG | LNA 3 + 3 | 2007 |
| 345 | GGGCTTTCTAAATGAC | LNA 3 + 3 | 2008 |
| 346 | TGACTCCCAGCAGGCC | LNA 3 + 3 | 2009 |
| 347 | GTGCATGAACTCACTG | LNA 3 + 3 | 2010 |
| 348 | GGTGCATGAACTCACT | LNA 3 + 3 | 2011 |
| 349 | ATCTGTCCCCTAATGG | LNA 3 + 3 | 2012 |
| 350 | CGGGTGCTGTTGTAAA | LNA 3 + 3 | 2013 |
| 351 | CCGGGTGCTGTTGTAA | LNA 3 + 3 | 2014 |
| 352 | CCTGGATCATGTCGAA | LNA 3 + 3 | 2015 |
| 353 | CCCTGGATCATGTCGA | LNA 3 + 3 | 2016 |
| 354 | TTTGAATTTGATTTCC | LNA 3 + 3 | 2017 |
| 355 | GGGCCTGAGCAGAAGT | LNA 3 + 3 | 2018 |
| 356 | GGGGGCTTTCTAAAT | LNA 3 + 3 | 2019 |
| 357 | TTTGTTTACACTTCC | LNA 3 + 3 | 2020 |
| 358 | CCAGCTAAAGGTGGG | LNA 3 + 3 | 2021 |
| 359 | ATGGCTGGGTCCCAA | LNA 3 + 3 | 2022 |
| 360 | GAGTTTTCCTTAGG | LNA 3 + 3 | 2023 |
| 361 | AGGGGTGGCAAGGCA | LNA 3 + 3 | 2024 |
| 362 | TGACTCCCAGCAGGC | LNA 3 + 3 | 2025 |
| 363 | GAAGCGCTGGCAACC | LNA 3 + 3 | 2026 |
| 364 | GTGCATGAACTCACT | LNA 3 + 3 | 2027 |
| 365 | GTGGTGCAAGTGGAC | LNA 3 + 3 | 2028 |
| 366 | CTAATGGCTTCCACC | LNA 3 + 3 | 2029 |
| 367 | CCCCTAATGGCTTCC | LNA 3 + 3 | 2030 |
| 368 | ATCTGTCCCCTAATG | LNA 3 + 3 | 2031 |
| 369 | GATCTGTCCCCTAAT | LNA 3 + 3 | 2032 |
| 370 | AGATCTGTCCCCTAA | LNA 3 + 3 | 2033 |
| 371 | GGTGCTGTTGTAAAG | LNA 3 + 3 | 2034 |
| 372 | CCGGGTGCTGTTGTA | LNA 3 + 3 | 2035 |
| 373 | GATCATGTCGAATTT | LNA 3 + 3 | 2036 |
| 374 | CCTGGATCATGTCGA | LNA 3 + 3 | 2037 |
| 375 | CCCTGGATCATGTCG | LNA 3 + 3 | 2038 |
| 376 | GATTTCCATCACCTC | LNA 3 + 3 | 2039 |
| 377 | TTGAATTTGATTTCC | LNA 3 + 3 | 2040 |
| 378 | AGCAGTTCTCCTCCA | LNA 3 + 3 | 2041 |
| 379 | GCCTGAGCAGAAGTT | LNA 3 + 3 | 2042 |
| 380 | GGGCAAGGGCCTGAG | LNA 3 + 3 | 2043 |
| 381 | CCCACACTTTCTTTA | LNA 3 + 3 | 2044 |
| 382 | TAGCACCTGCTTCCA | LNA 3 + 3 | 2045 |
| 383 | CGGGGCTTTCTAA | LNA 3 + 3 | 2046 |
| 384 | CCATTCATGCTTTC | LNA 3 + 3 | 2047 |
| 385 | AAGCGCTGGCAACC | LNA 3 + 3 | 2048 |
| 386 | ACCAGAGCCCTTTG | LNA 3 + 3 | 2049 |
| 387 | CCCCTAATGGCTTC | LNA 3 + 3 | 2050 |
| 388 | GTCCCCTAATGGCT | LNA 3 + 3 | 2051 |
| 389 | ATCTGCCCCTAAT | LNA 3 + 3 | 2052 |
| 390 | AGATCTGTCCCCTA | LNA 3 + 3 | 2053 |
| 391 | CGGGTGCTGTTGTA | LNA 3 + 3 | 2054 |
| 392 | ATCATGTCGAATTT | LNA 3 + 3 | 2055 |
| 393 | CCCTGGATCATGTC | LNA 3 + 3 | 2056 |
| 394 | CCTTTGAATTTGAT | LNA 3 + 3 | 2057 |
| 395 | TTGCGGAAGCAGTA | LNA 3 + 3 | 2058 |
| 396 | GCCTGAGCAGAAGT | LNA 3 + 3 | 2059 |
| 397 | GGGGGCTTTCTAA | LNA 2 + 3 | 2060 |
| 398 | AGCGCTGGCAACC | LNA 2 + 3 | 2061 |
| 399 | CCCCTAATGGCTT | LNA 2 + 3 | 2062 |
| 399 | CCCCTAATGGCTT | LNA 3 + 2 | 2063 |
| 400 | TCCCCTAATGGCT | LNA 3 + 2 | 2064 |
| 401 | TCATGTCGAATTT | LNA 2 + 3 | 2065 |
| 402 | ATCATGTCGAATT | LNA 3 + 2 | 2066 |

Table 1 shows the nucleic acid sequences of selected oligonucleotides of the present invention as well as the modifications of the nucleotides, wherein LNA 4+4 means 4×LNAs at the 5'- and 3'-end of the oligonucleotide are modified, wherein LNA 4+3 means 4×LNAs at the 5'-end and 3×LNAs at the 3'-end of the oligonucleotide are modified, wherein LNA 3+4 means 3×LNAs at the 5'-end and 4×LNAs at the 3'-end of the oligonucleotide are modified, wherein LNA 3+3 means 3×LNAs at the 5'- and 3'-end of the oligonucleotide are modified, wherein LNA 3+2 means 3×LNAs at the 5'-end and 2×LNAs at the 3'-end of the oligonucleotide are modified, wherein LNA 2+3 means 2×LNAs at the 5'-end and 3×LNAs at the 3'-end of the oligonucleotide are modified, wherein LNA 2+2 means 2×LNAs at the 5'- and 3'-end of the oligonucleotide are modified. Alternatively, some oligonucleotides comprise ENA 4+4, i.e., 4×ENA at the 5'- and 3'-end of the oligonucleotide are modified, or ENA 3+3, i.e., 3×ENA at the 5'- and 3'-end of the oligonucleotide are modified. Further oligonucleotides comprise 2' O-meth 4+4, wherein the oligonucleotide comprises 4×2' O-methyl modified nucleotides at the 5'- and 3'-end of the oligonucleotide, or comprises 2' fluoro 4+4, wherein the oligonucleotide comprises 4×2' fluoro modified nucleotides at the 5'- and 3'-end. Oligonucleotides comprising LNA 3+TEG comprise 3×LNAs at the 5'-end and one triethylene glycol (TEG) at the 3'-end of the oligonucleotide. Some oligonucleotides comprise LNAs which are not arranged in a row but are separated by an unlocked nucleoside having for example the sequences 3LNA+9N+1LNA+1N+2LNA, 1LNA+1N+2LNA+8N+1LNA+1N+1LNA, 2LNA+8N+2LNA+1N+1LNA, 2LNA+9N+1LNA+1N+1LNA, 2LNA+8N+1LNA+2N+1LNA, 3LNA+8N+1LNA+1N+1LNA, 3LNA+8N+1LNA+1N+1LNA, 2LNA+9N+1LNA+1N+1LNA, or 2LNA+8N+2LNA+1N+1LNA, wherein "N" is a nucleoside without locked modification. "ASPH" in combination with a number refers to the different oligonucleotides and their different modifications as described in Table 1. These modified oligonucleotides were tested e.g. in experiments shown in the following examples. The antisense oligonucleotides of the present invention can be described differently, e.g., ASPH47, ASPH0047, ASPH_47 or ASPH_0047 referring to the same oligonucleotide.

For the purpose of clarity and a concise description, features are described herein as part of the same or separate embodiments, however, it will be appreciated that the scope of the invention may include embodiments having combinations of all or some of the features described.

The following examples will serve to further illustrate the present invention without, at the same time, however, constituting any limitation thereof. On the contrary, it is to be clearly understood that the scope of the present invention refers to various other embodiments, modifications, and equivalents thereof which, after reading the description herein, may suggest themselves to those skilled in the art without departing from the spirit of the invention.

EXAMPLES

In the following examples, the effect of the oligonucleotides listed in Table 1 has been tested in view of the reduction and inhibition, respectively, of TGF-beta1 and/or TGF-beta2 expression. SEQ ID NO. 144 (T-LNA: CGGCATGTCTATTTTGTA, wherein 3×nucleotides at the 5'- and 3'-end are LNAs) and SEQ ID NO. 145 (scr-LNA: CGTTTAGGCTATGTACTT, wherein 3×nucleotides at the 5'- and 3'-end are LNAs) are used as control oligonucleotides, wherein SEQ ID NO. 145 (negative control) is the scrambled form of SEQ ID NO. 144 (positive control). The cells were either transfected in the presence of a transfecting agent (e.g., Lipofectamine), or in the absence of any transfecting agent (which is defined as gymnotic transfection or unassisted transfection or gymnotic delivery). In case of gymnotic delivery the entry of the oligonucleotide into the cell solely depends on the interaction of the oligonucleotide with the cell (no compound/agent supports the entry). Therefore, gymnotic transfection or gymnotic delivery is considered to reflect better conditions of the in vivo settings.

Example 1

Figure 3B:
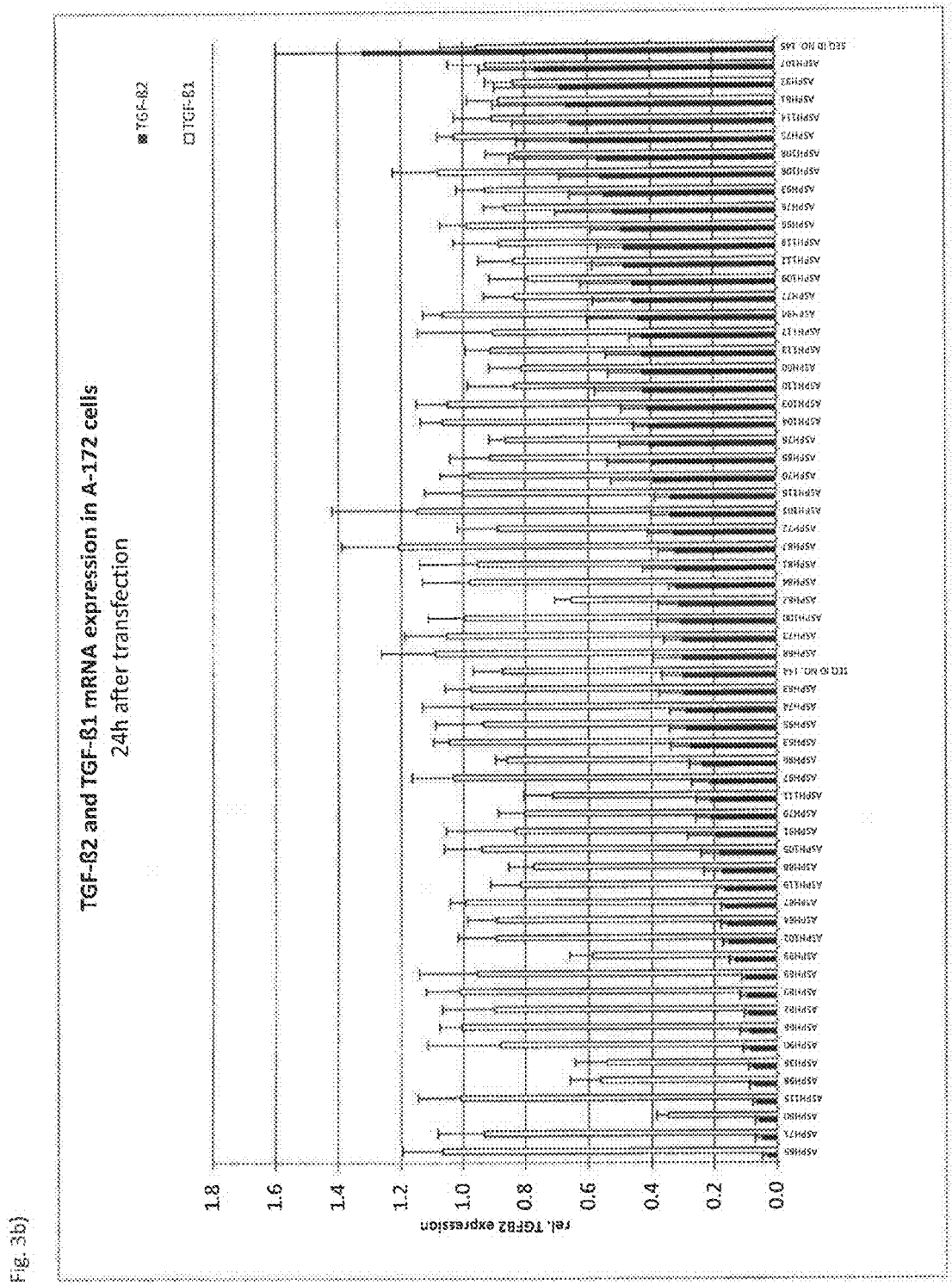
FIG. 3b) to the results for the modified oligonucleotides ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH95, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119.

Human A172 glioma cells were transfected with 10 nM of ASPH01, ASPH02, ASPH03, ASPH04, ASPH05, ASPH06, ASPH07, ASPH08, ASPH09, ASPH10, ASPH11, ASPH12, ASPH13, ASPH14, ASPH15, ASPH16, ASPH17, ASPH18, ASPH19, ASPH20, ASPH21, ASPH22, ASPH24, ASPH25, ASPH26, ASPH27, ASPH29, ASPH30, ASPH31, ASPH32, ASPH33, ASPH34, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, ASPH52, ASPH53, and ASPH54 (see FIG. 3a); ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH95, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119 (see FIG. 3b), or ASPH36, ASPH71, ASPH73, ASPH120, ASPH121, ASPH122, ASPH123, ASPH124, ASPH125, ASPH126, ASPH127, ASPH128, ASPH129, ASPH130, ASPH131, ASPH132, ASPH133, ASPH134, ASPH135, ASPH136, ASPH137, ASPH138, ASPH139, ASPH140, ASPH141, ASPH142, ASPH143, ASPH145, ASPH146, ASPH147, ASPH148, ASPH149, ASPH150, ASPH151, ASPH152, ASPH153, ASPH154, ASPH155, ASPH157, ASPH158, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183 (see FIG. 3c), and the controls of SEQ ID NO. 144 and 145, respectively, in the presence of a transfecting agent. The expression of TGF-beta1 and TGF-beta2 mRNA was determined 24 h after transfection. Significant reduction of the expression of TGF-beta1 and TGF-beta2 mRNA is demonstrated in FIGS. 3a) to 3c). The dual TGF-beta1 and TGF-beta2 reactive oligonucleotides ASPH01, ASPH02, ASPH03, ASPH04, ASPH05, ASPH06, ASPH07, ASPH08 and ASPH09 show a significant reduction of the expression of both TGF-beta1 and TGF-beta2 mRNA, while the selective TGF-beta2 oligonucleotides significantly inhibit TGF-beta2 mRNA expression.

Example 2

Figure 4A:
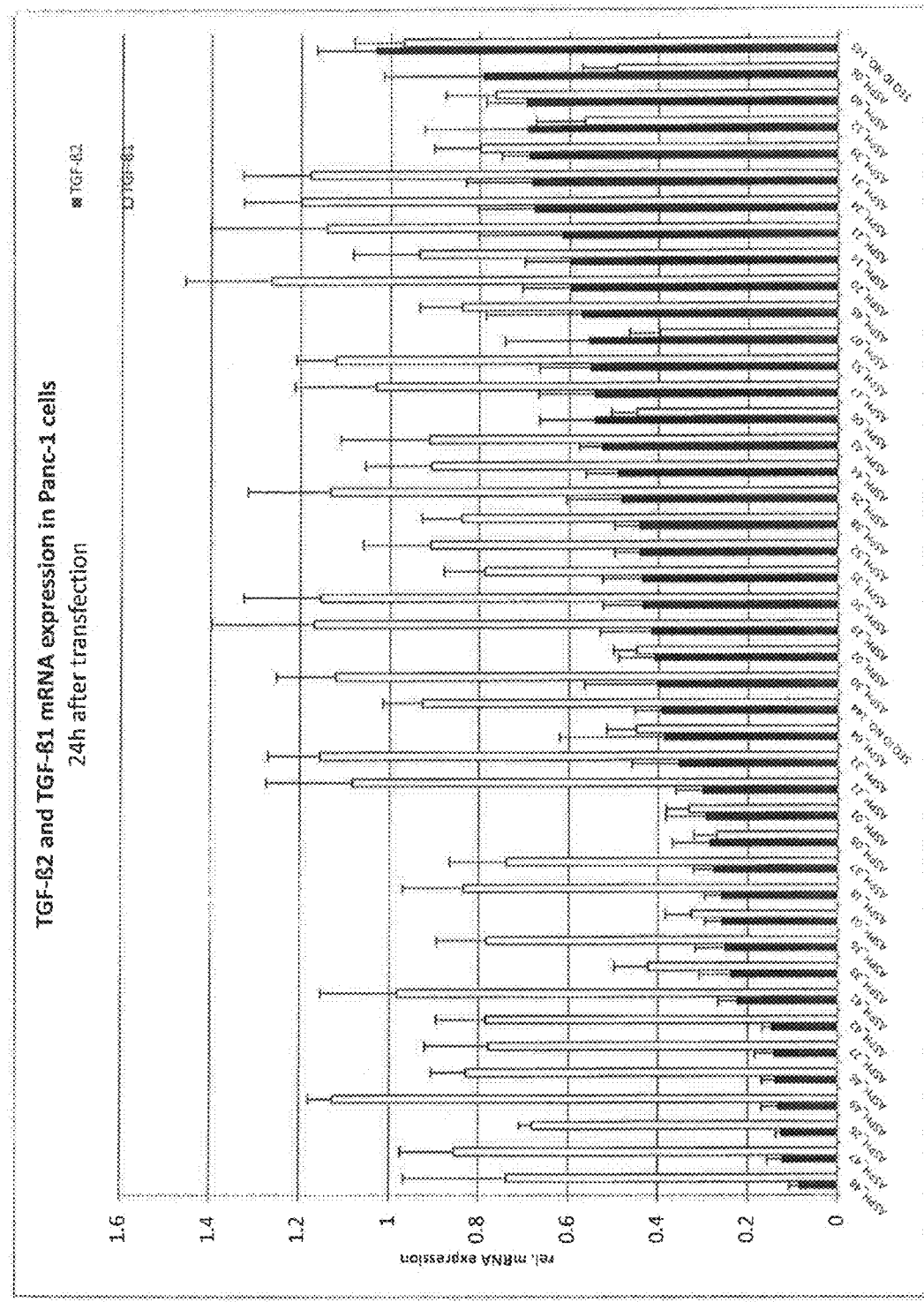
FIGS. 4a) to 4c) depict the inhibition of the expression of TGF-beta1 and TGF-beta2 mRNA in human Panc-1 pancreatic cancer cells. Panc-1 cells were transfected with different modified oligonucleotides in a dose of 10 nM (in the presence of a transfecting agent), and the inhibition of the TGF-beta1 (white columns) and TGF-beta2 (black columns) mRNA expression was measured 24 h after transfection.
Figure 4B:
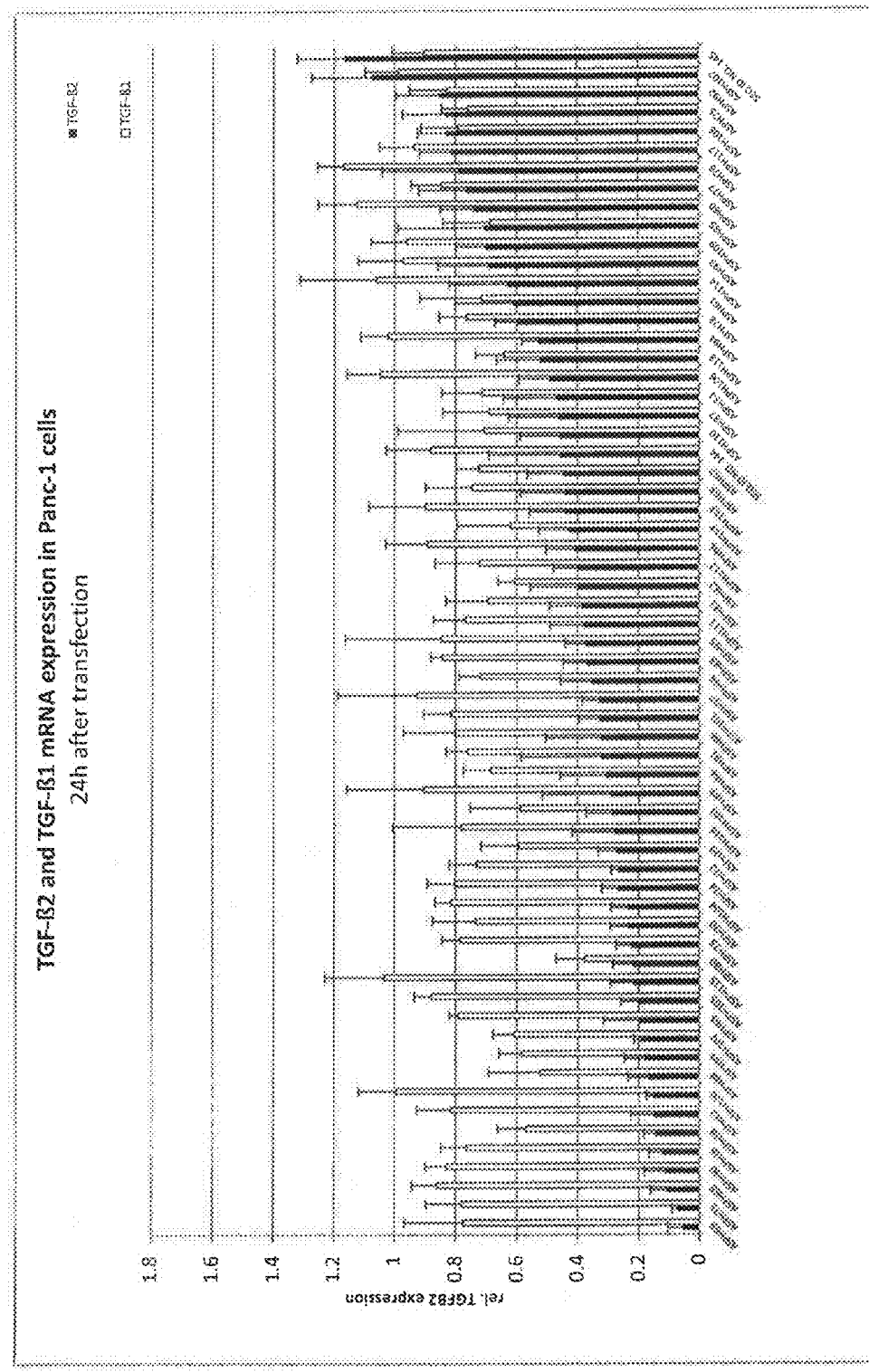
FIG. 4b) to the results for the modified oligonucleotides ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119.
Figure 4C:
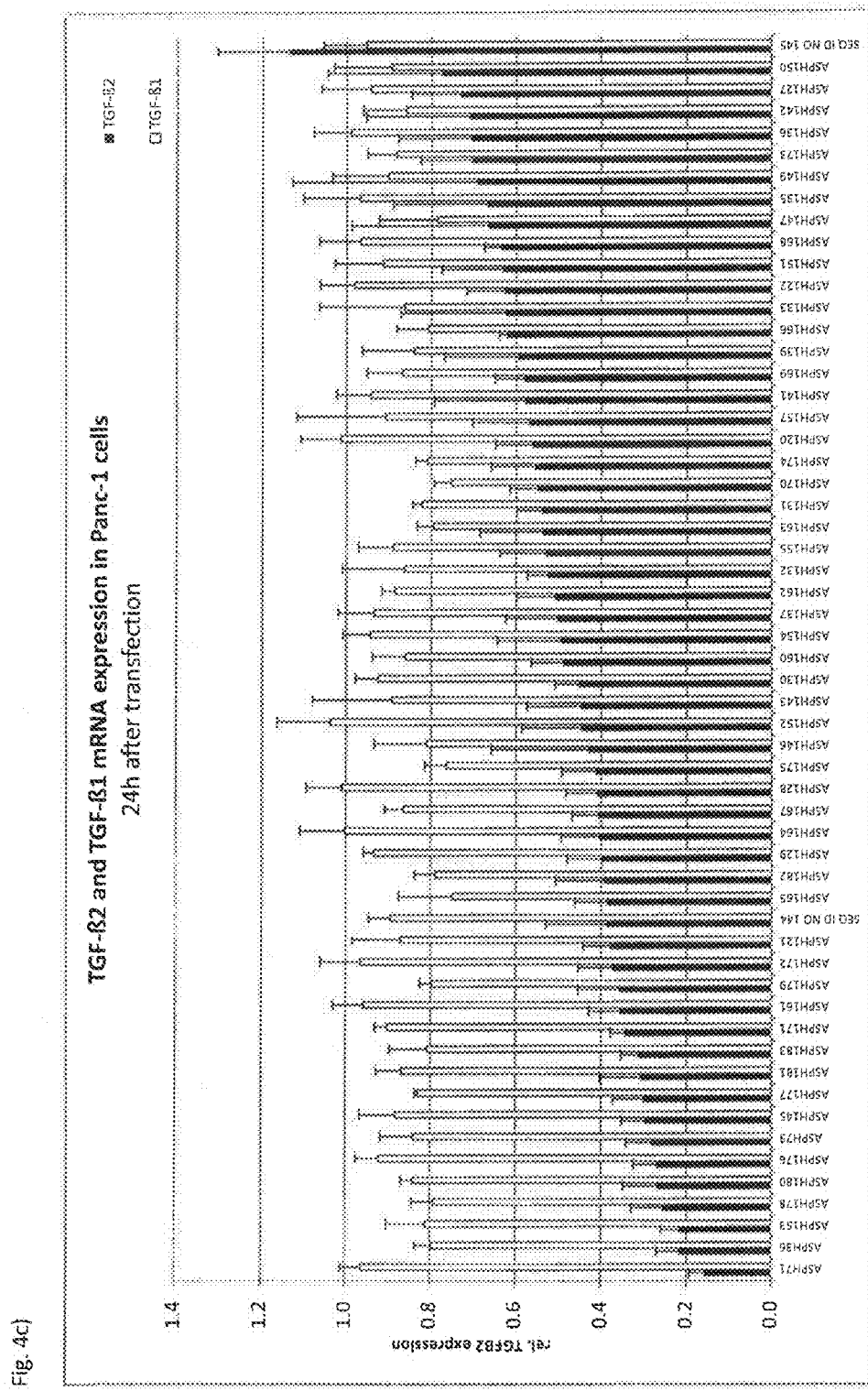
FIG. 4c) to the results for the modified oligonucleotides ASPH36, ASPH71, ASPH73, ASPH120, ASPH121, ASPH122, ASPH127, ASPH128, ASPH129, ASPH130, ASPH131, ASPH132, ASPH133, ASPH135, ASPH136, ASPH137, ASPH139, ASPH141, ASPH142, ASPH143, ASPH145, ASPH146, ASPH147, ASPH149, ASPH150, ASPH151, ASPH152, ASPH153, ASPH154, ASPH155, ASPH157, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183. Experiments are described in Example 2.

Human Panc-1 pancreatic cancer cells were transfected with 10 nM of ASPH01, ASPH02, ASPH03, ASPH04, ASPH05, ASPH06, ASPH07, ASPH08, ASPH12, ASPH14, ASPH17, ASPH18, ASPH20, ASPH21, ASPH22, ASPH24, ASPH25, ASPH26, ASPH27, ASPH29, ASPH30, ASPH31, ASPH32, ASPH33, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, and ASPH52 (see FIG. 4a); ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119 (see FIG. 4b), or ASPH36, ASPH71, ASPH73, ASPH120, ASPH121, ASPH122, ASPH127, ASPH128, ASPH129, ASPH130, ASPH131, ASPH132, ASPH133, ASPH135, ASPH136, ASPH137, ASPH139, ASPH141, ASPH142, ASPH143, ASPH145, ASPH146, ASPH147, ASPH149, ASPH150, ASPH151, ASPH152, ASPH153, ASPH154, ASPH155, ASPH157, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183 (see FIG. 4c) and the controls of SEQ ID NO. 144 and 145, respectively, in the presence of a transfecting agent. The expression of TGF-beta1 and TGF-beta2 mRNA was determined 24 h after transfection. Significant reduction of the expression of TGF-beta1 and TGF-beta2 mRNA is demonstrated in FIGS. 4a) to 4c). The dual TGF-beta1 and TGF-beta2 reactive oligonucleotides ASPH01, ASPH02, ASPH03, ASPH04, ASPH05, ASPH06, ASPH07, and ASPH08, respectively, show again a significant reduction of the expression of both TGF-beta1 and TGF-beta2 mRNA, while the selective TGF-beta2 oligonucleotides significantly inhibit TGF-beta2 mRNA expression.

Example 3

In further experiments the inhibitory effect of each of ASPH01, ASPH03, ASPH05, ASPH17, ASPH18, ASPH22, ASPH26, ASPH27, ASPH33, ASPH36, ASPH37, ASPH41, ASPH42, ASPH45, ASPH46, ASPH47, ASPH48, ASPH49, ASPH64, ASPH65, ASPH66, ASPH69, ASPH71, ASPH80, ASPH82, ASPH88, ASPH89, ASPH90, ASPH98, ASPH99, ASPH102, ASPH105, ASPH115, ASPH121, ASPH140, ASPH153, ASPH165, ASPH171, ASPH178, ASPH181, ASPH184, ASPH185, ASPH186, ASPH187, ASPH188, ASPH189, and of the controls of SEQ ID NO.144 and SEQ ID NO. 145 was tested in human A172 glioma cells. A172 cells were transfected with these modified oligonucleotides in doses of 20 nM, 4 nM, 0.8 nM, 0.16 nM, and 0.04 nM, respectively, in the presence of a transfecting agent. The remaining TGF-beta2 mRNA was measured 24 h after transfection. TGF-beta2 values were normalized to GAPDH and oligonucleotide concentrations resulting in 50% reduction of TGF-beta2 mRNA (=$IC_{50}$ values) were calculated. All $IC_{50}$ values were referenced to the $IC_{50}$ value of ASPH_036 (ASPH36) that was 0.33 nM and the results are shown as fold-difference of the $IC_{50}$ value of ASPH_036 Table 2:

| Oligonucleotide | Fold $IC_{50}$ referenced to ASPH_036 |
| --- | --- |
| ASPH_080 | 0.591 |
| ASPH_069 | 0.673 |
| ASPH_065 | 0.773 |
| ASPH_105 | 0.882 |
| ASPH_036 | 1.000 |
| ASPH_046 | 1.142 |
| ASPH_098 | 1.182 |
| ASPH_071 | 1.237 |
| ASPH_026 | 1.242 |
| ASPH_047 | 1.303 |
| ASPH_088 | 1.455 |
| ASPH_185 | 1.456 |
| ASPH_115 | 1.545 |
| ASPH_153 | 1.665 |
| ASPH_181 | 1.918 |
| ASPH_027 | 2.000 |
| ASPH_089 | 2.091 |
| ASPH_102 | 2.091 |
| ASPH_041 | 2.182 |
| ASPH_018 | 2.212 |
| ASPH_049 | 2.455 |
| ASPH_022 | 2.485 |
| ASPH_188 | 2.639 |
| ASPH_189 | 2.660 |
| ASPH_042 | 2.848 |
| ASPH_178 | 3.147 |
| ASPH_048 | 3.182 |
| ASPH_066 | 3.182 |
| ASPH_033 | 3.182 |
| ASPH_045 | 3.636 |
| ASPH_121 | 3.644 |
| ASPH_171 | 3.871 |
| ASPH_005 | 3.954 |
| ASPH_003 | 4.111 |
| ASPH_082 | 4.818 |
| ASPH_037 | 5.303 |
| ASPH_099 | 5.545 |
| ASPH_090 | 6.727 |
| ASPH_165 | 7.175 |
| ASPH_186 | 7.655 |
| ASPH_017 | 8.455 |
| ASPH_001 | 9.242 |
| ASPH_187 | 9.990 |
| ASPH_064 | 10.091 |
| ASPH_140 | 11.482 |
| ASPH_184 | 12.224 |
| SEQ ID NO 144 | 17.212 |
| SEQ ID NO 145 | n.a |

All the modified oligonucleotides show an $IC_{50}$ in a low nanomolar to picomolar range, which is markedly lower than $IC_{50}$ of the positive control oligonucleotide of SEQ ID NO. 144; the $IC_{50}$ of the negative control of SEQ ID NO. 145 was not calculable.

Example 4

Human Panc-1 pancreatic cancer cells were treated with 3.3 μM of ASPH17, ASPH18, ASPH22, ASPH25, ASPH33, ASPH35, ASPH36, ASPH41, ASPH42, ASPH45, ASPH46, ASPH47, ASPH48, ASPH49, ASPH65, ASPH66, ASPH67, ASPH69, ASPH71, ASPH79, ASPH80, ASPH82, ASPH88, ASPH89, ASPH90, ASPH91, ASPH98, ASPH99, ASPH102, ASPH105, ASPH111, ASPH115, ASPH119, ASPH121, ASPH139, ASPH140, ASPH146, ASPH151, ASPH153, ASPH165, ASPH171, ASPH172, ASPH176, ASPH178, ASPH180, and ASPH183, respectively, or the controls of SEQ ID NO. 144 and 145 in the absence of a transfecting agent (gymnotic transfection or gymnotic delivery). The inhibitory effect of the modified oligonucleotides on expression of TGF-beta1 and TGF-beta2 mRNA, respectively, was determined 72 h after treatment start. Under gymnotic delivery experimental conditions, the oligonucleotides enter the cells and strongly inhibit the expression of TGF-beta2 mRNA. The results of the experiments are shown in FIG. 5.

Example 5

Figure 6A:
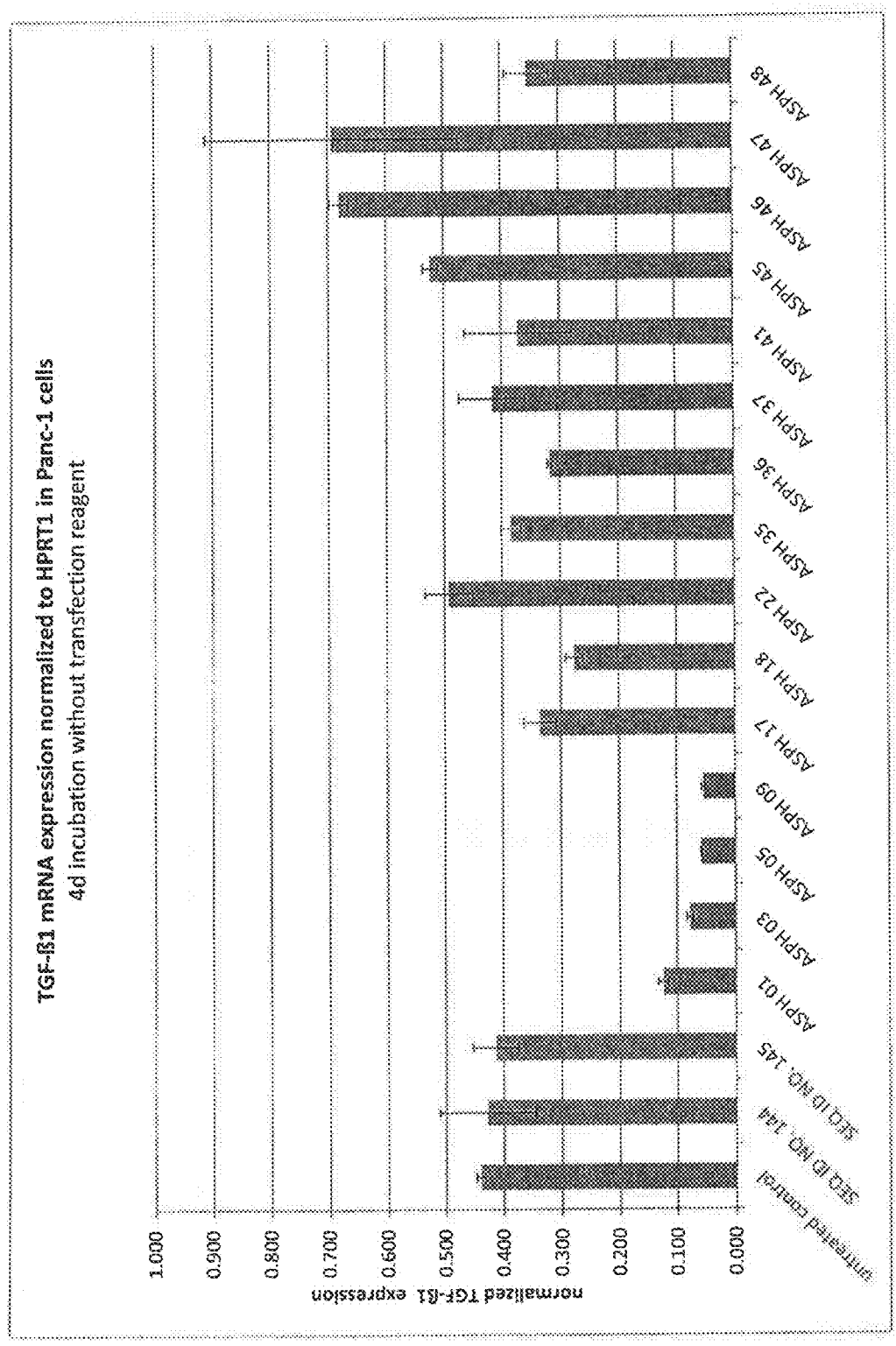
FIG. 6a) and FIG. 6b) show the results for the modified oligonucleotides ASPH01, ASPH03, ASPH05, ASPH09, ASPH17, ASPH18, ASPH22, ASPH35, ASPH36, ASPH37, ASPH41, ASPH45, ASPH46, ASPH47, and ASPH48 on mRNA (FIG. 7a) and protein (FIG. 7b) level. Experiments are described in Example 5.
Figure 7B:
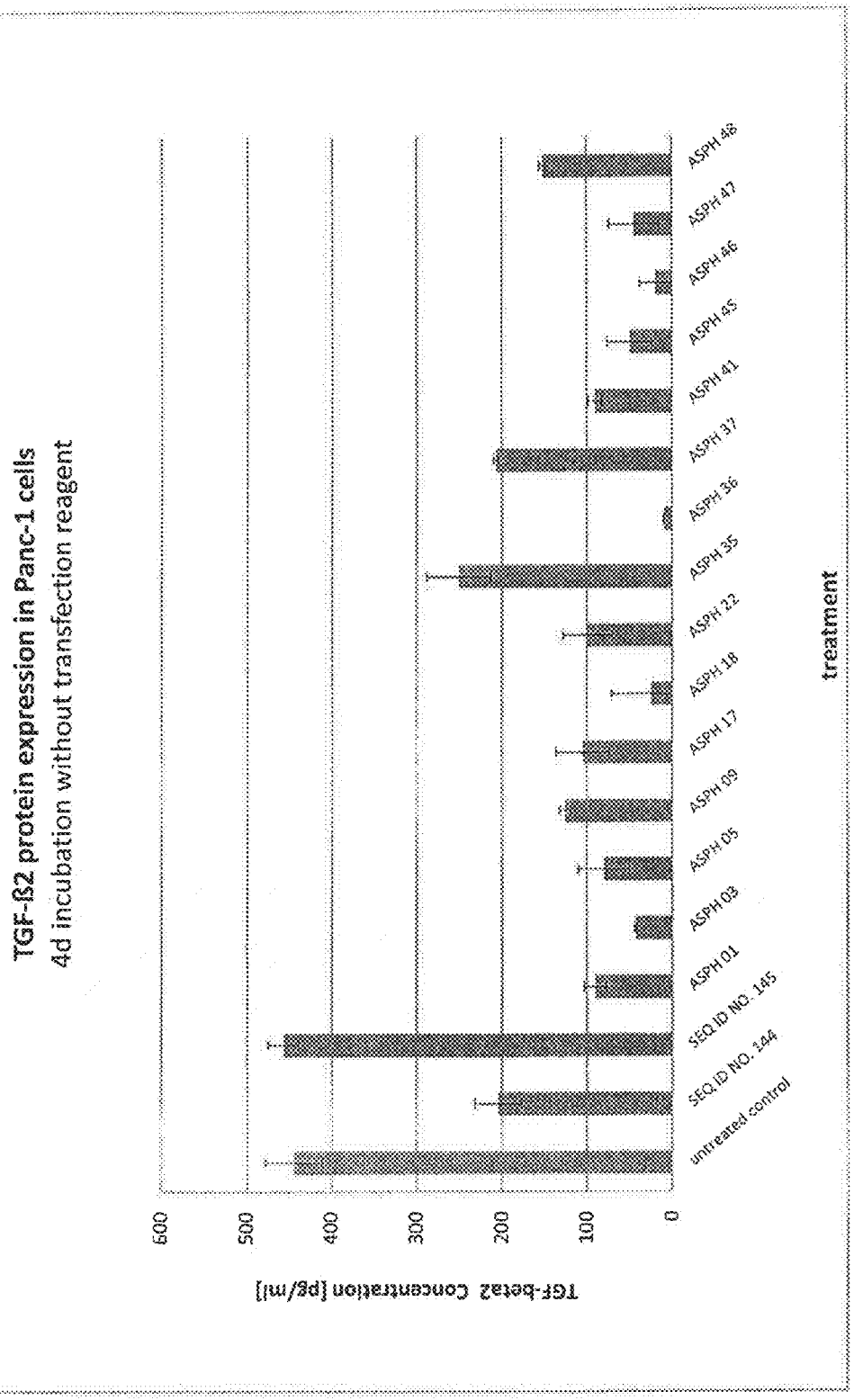

In further experiments human Panc-1 pancreatic cancer cells were transfected with 10 μM of modified oligonucleotides ASPH01, ASPH03, ASPH05, ASPH09, ASPH17, ASPH18, ASPH22, ASPH35, ASPH36, ASPH37, ASPH41, ASPH45, ASPH46, ASPH47, and ASPH48, respectively, or the controls of SEQ ID NO. 144 and 145 in the absence of a transfecting agent (gymnotic transfection or gymnotic delivery). The oligonucleotides were added to the cells for 2 days, after which medium was changed, and further incubation for 2 days was carried out in oligonucleotide-containing medium. Expression of TGF-beta1 mRNA (FIG. 6a) and TGF-beta2 mRNA (FIG. 6b) was then measured and normalized to HPRT1 (Hypoxanthin-Phosphoribosyl-Transferase1). Cell supernatants were analysed for TGF-beta1 (FIG. 7a) and TGF-beta2 (FIG. 7b) protein by ELISA. Under gymnotic delivery experimental conditions, dual TGF-beta1 and TGF-beta2 reactive oligonucleotide ASPH01, ASPH03, ASPH05, and pan-specific ASPH09 significantly inhibit the expression of TGF-beta1 and TGF-beta2 mRNA, and protein. All the other oligonucleotides significantly inhibit the expression of TGF-beta2 mRNA and protein.

Example 6

Figure 8B:
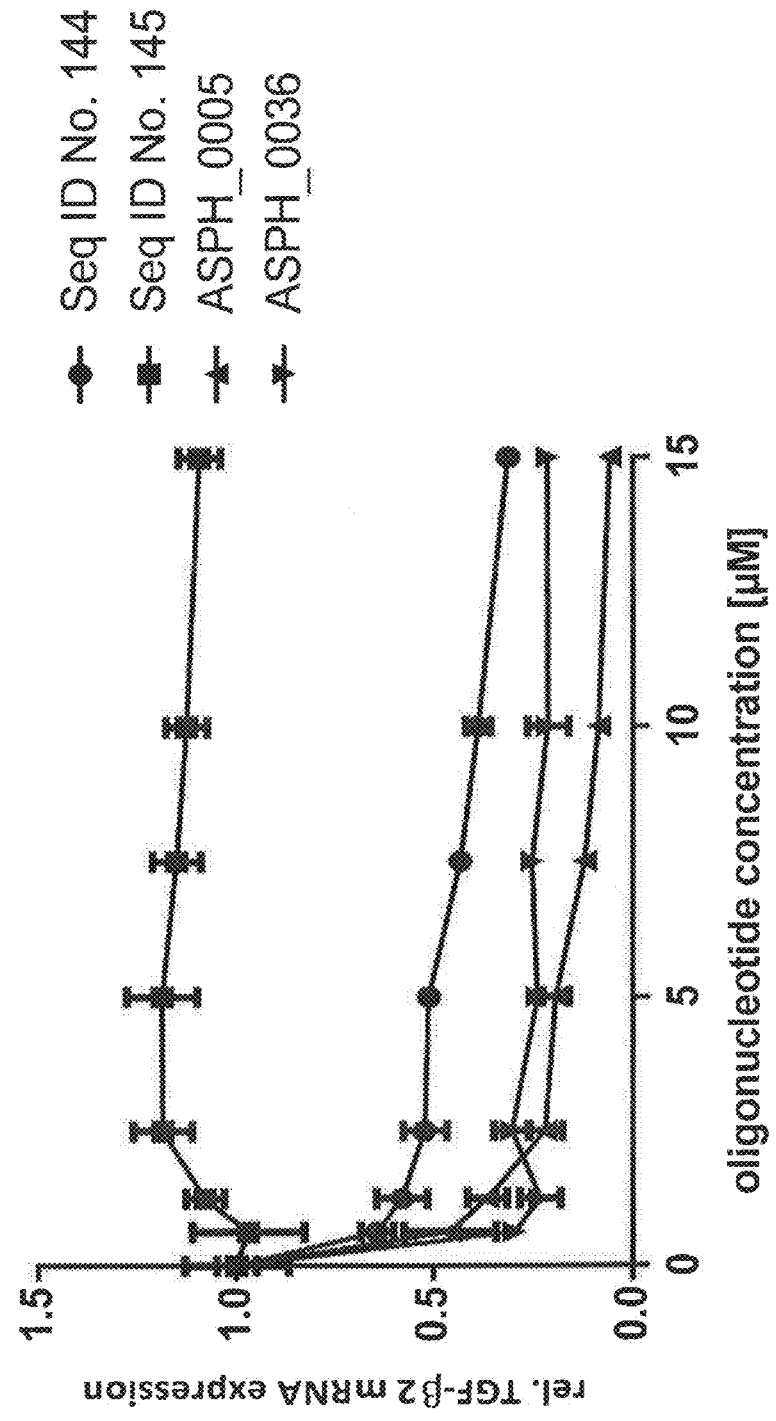
FIG. 8 depicts the dose-dependent effect of modified oligonucleotides ASPH05 and ASPH36 on TGF-beta1 and TGF-beta2 mRNA expression. Panc-1 cells were treated for 4 days with 15 µM, 10 µM, 7.5 µM, 5 µM, 2.5 µM, 1.25 µM, or 0.625 µM of either ASPH05 (dual TGF-beta1 and TGF-beta2 oligonucleotide) or ASPH36 (selective TGF-beta2 oligonucleotide) modified oligonucleotide in the absence of a transfection reagent. Remaining TGF-beta1 (FIG. 8a) or TGF-beta2 mRNA (FIG. 8b) was measured after 4 days. Experiments are described in Example 6.

In another experiment dose dependency of the inhibitory effect of modified oligonucleotides of the present invention was tested. Human Panc-1 pancreatic cancer cells were treated with 15 µM, 10 µM, 7.5 µM, 5 µM, 2.5 µM, 1.25 µM, or 0.625 µM ASPH05 or ASPH36, or the controls of SEQ ID NO. 144 and 145, respectively, without using a transfection reagent. The oligonucleotides were added to the cells for 2 days. Thereafter media were changed and cells were incubated for 2 further days in oligonucleotide-containing medium, after which (total treatment time: 4 days) the expression of TGF-beta1 (FIG. 8a) and TGF-beta2 (FIG. 8b) mRNA was measured. The dual TGF-beta1 and TGF-beta2 reactive oligonucleotide ASPH05 shows a marked dose dependent inhibition of both TGF-beta1 and TGF-beta2 mRNA expression, and ASPH36 inhibits specifically the expression of TGF-beta2 mRNA in a dose-dependent manner.

Example 7

Figure 9:
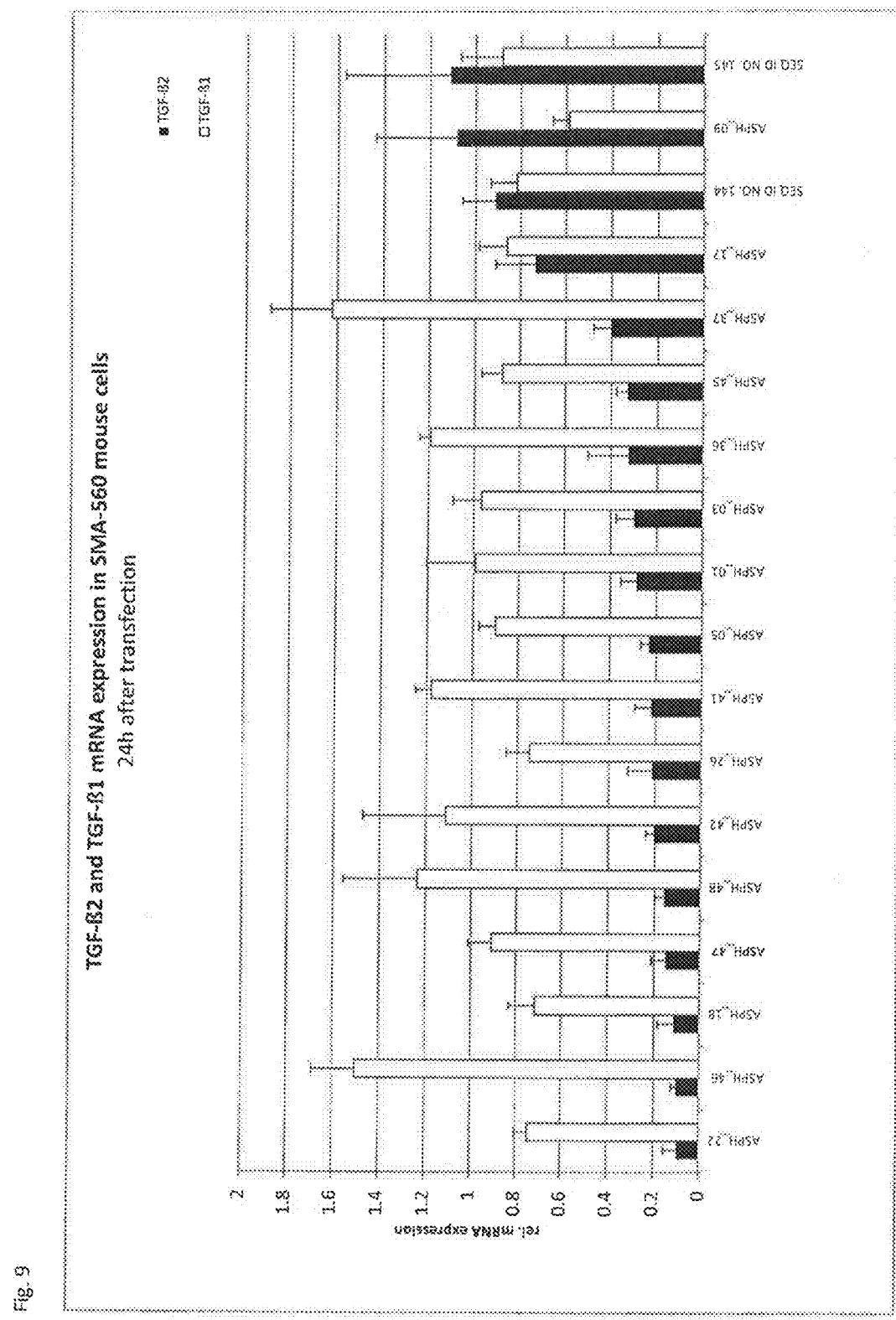
FIG. 9 shows the inhibition of the expression of TGF-beta1 and TGF-beta2 mRNA in mouse SMA-560 glioma cells. SMA-560 cells were transfected with ASPH01, ASPH03, ASPH05, ASPH09, ASPH17, ASPH18, ASPH22, ASPH26, ASPH36, ASPH37, ASPH41, ASPH42, ASPH45, ASPH46, ASPH47, or ASPH48 in a dose of 10 nM (in the presence of a transfecting agent). Inhibition of the mouse TGF-beta1 (white columns) and TGF-beta2 (black columns) mRNA expression was determined 24 h after transfection. Experiments are described in Example 7.

Mouse SMA-560 glioma cells were transfected with 10 nM ASPH01, ASPH03, ASPH05, ASPH09, ASPH17, ASPH18, ASPH22, ASPH26, ASPH36, ASPH37, ASPH41, ASPH42, ASPH45, ASPH46, ASPH47, or ASPH48, or the controls of SEQ ID NO. 144 and 145, respectively, in the presence of a transfecting agent. 24 h after transfection, the inhibition of the expression of TGF-beta1 (white columns) and TGF-beta2 (black columns) mRNA was determined. The pan-specific ASPH09 inhibits the expression of the mouse TGF-beta1 mRNA, and the other oligonucleotides tested strongly inhibit the expression of the mouse TGF-beta2 mRNA. The results are presented in FIG. 9.

Example 8

Figure 10:
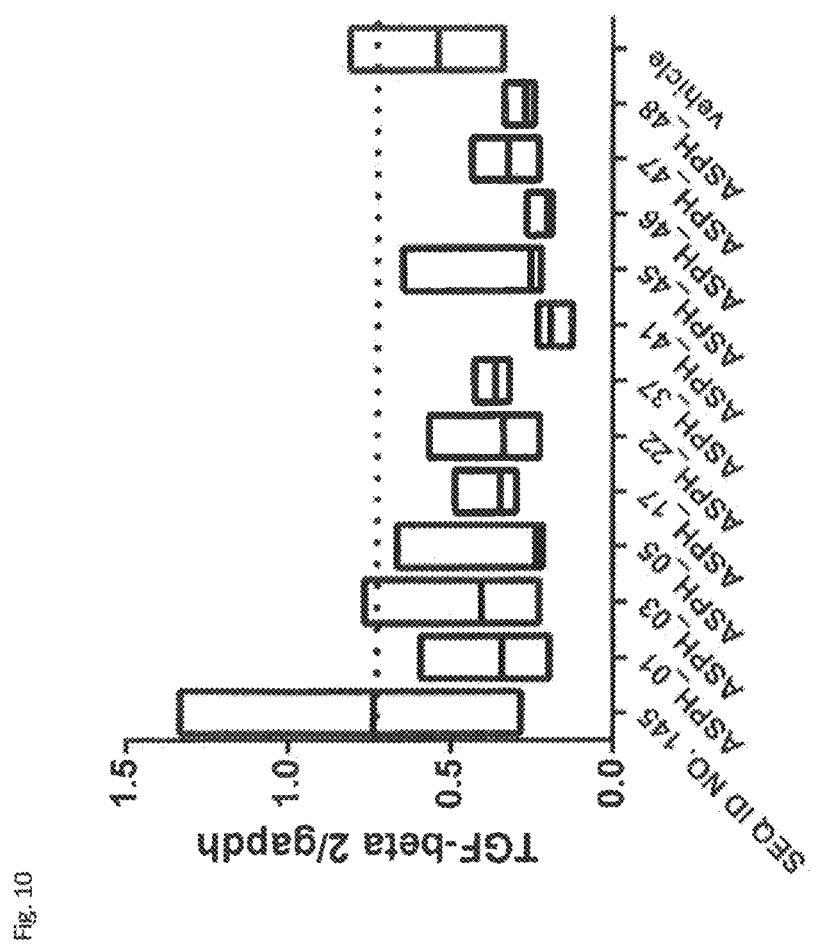
FIG. 10 presents in vivo data referring to the treatment of female athymic nude mice with ASPH01, ASPH03, ASPH05, ASPH17, ASPH22, ASPH37, ASPH41, ASPH45, ASPH46, ASPH47, or ASPH48 at 14 mg/kg body weight by subcutaneous injection for 5 consecutive days. 24 h after the last treatment, mice were sacrificed and mouse TGF-beta 2 mRNA was quantified in kidney tissue lysates. Data—representing TGF-beta2 to GAPDH mRNA ratio—are shown as a box plot in which median values and min. and max. values are presented (data expressed as n=4, except ASPH46 group n=3). Experiments are described in Example 8.

Female athymic nude mice (Hsd:Athymic Nude-Foxn1$^{nu}$) were treated for 5 consecutive days with 14 mg/kg or 50 mg/kg of oligonucleotide ASPH01, ASPH03, ASPH05, ASPH17, ASPH22, ASPH37, ASPH41, ASPH45, ASPH46, ASPH47, or ASPH48, and control of SEQ ID NO. 145, respectively, or saline by subcutaneous injection. The day after the last treatment, the mice were sacrificed. Mouse TGF-beta2 mRNA was quantified in kidney tissue lysates. In FIG. 10, data—representing TGF-beta2 to GAPDH mRNA ratio—are shown as a box plot in which median values and min. and max. values are presented (data expressed as n=4, except ASPH46 group n=3). All the tested oligonucleotides inhibited the expression of TGF-beta2 mRNA in the kidney of these mice.

Example 9

Figure 11:
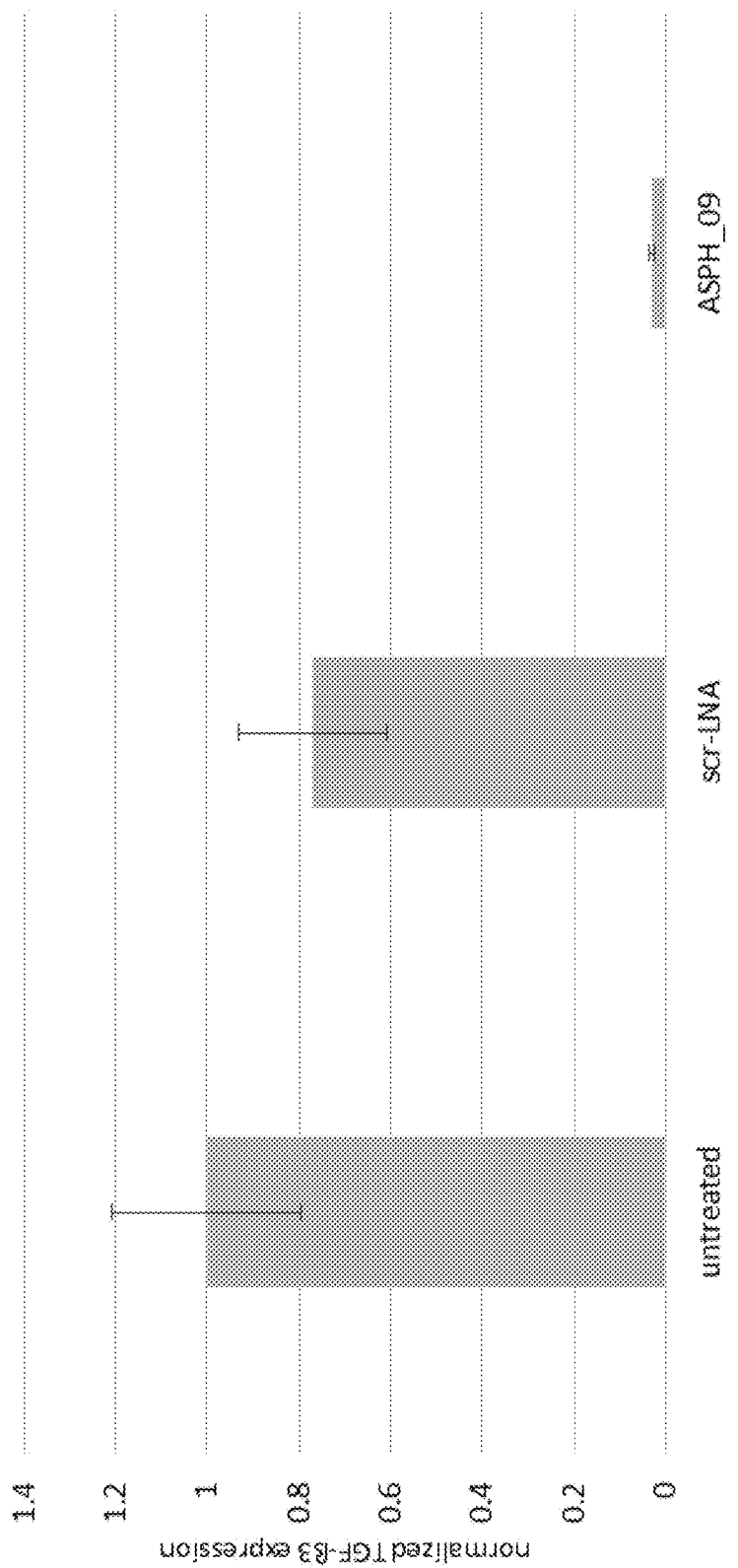
FIG. 11 shows the inhibition of the expression of TGF-beta3 mRNA in Panc-1 cells. Panc-1 cells were treated with ASPH09 in a dose of 10 µM in the absence of any transfection reagent (gymnotic transfection or unassisted transfection), and inhibition of the TGF-beta3 mRNA expression was measured after 4 days. ASPH09 is a pan-specific oligonucleotide inhibiting the expression of TGF-beta3 as well as TGF-beta1 and TGF-beta2 (FIGS. 6a and 6b). Experiment is described in Example 9.

In another experiment human Panc-1 pancreatic cancer cells were transfected with 10 µM of modified oligonucleotide ASPH09 or the control of SEQ ID NO. 145 in the absence of any transfecting agent (gymnotic transfection or gymnotic delivery). The oligonucleotides were added to the cells for 2 days, after medium was changed, and further incubation for 2 days was carried out in oligonucleotide-containing medium. Expression of TGF-beta3 mRNA (see FIG. 11) was then measured and normalized to HPRT1 (Hypoxanthin-Phosphoribosyl-Transferase1). Under gymnotic delivery experimental conditions, the pan-specific oligonucleotide ASPH09 significantly inhibits the expression of TGF-beta3 mRNA.

Example 10

Human Panc-1 pancreatic cancer cells were treated with 10 µM, 3.3 µM, 1.1 µM, 0.37 µM, and 0.12 µM of ASPH03, ASPH36, ASPH45, ASPH47, ASPH65, ASPH69, AASPH71, ASPH80, ASPH115, ASPH 121, ASPH153, ASPH185, and ASPH189, respectively, in the absence of a transfecting agent (gymnotic transfection or gymnotic delivery). The inhibitory effect of the modified oligonucleotides on expression of TGF-beta2 mRNA, was determined 72 h after treatment start. TGF-beta2 values were normalized to GAPDH and oligonucleotide concentrations resulting in 50% reduction of TGF-beta2 mRNA (=$IC_{50}$ values) were calculated. Under gymnotic delivery experimental conditions, the oligonucleotides enter the cells and strongly inhibit the expression of TGF-beta2 mRNA. The results of the experiments are shown in Table 3:

| Name | IC50 (µM) |
|---|---|
| ASPH_065 | 0.37 |
| ASPH_071 | 0.371 |
| ASPH_115 | 0.6 |
| ASPH_069 | 0.655 |
| ASPH_047 | 0.78 |
| ASPH_080 | 0.81 |
| ASPH_153 | 0.9 |
| ASPH_045 | 1.21 |
| ASPH_121 | 1.27 |
| ASPH_036 | 1.5 |
| ASPH_185 | 3.05 |
| ASPH_003 | 3.62 |
| ASPH_189 | 4.26 |

All the modified oligonucleotides show an $IC_{50}$ in the low micromolar or even submicromolar range, showing that they have very high potency even without the requirement of a transfection reagent.

Example 11

Human Panc-1 pancreatic cancer cells were treated with 10 µM, 3.3 µM, 1.1 µM, 0.37 µM, and 0.12 µM of ASPH47, ASPH190, ASPH191, ASPH192, and ASPH193, respectively, in the absence of a transfecting agent (gymnotic transfection or gymntic delivery). The inhibitory effect of the modified oligonucleotides on expression of TGF-beta2 mRNA, was determined 72 h after treatment start. TGFbeta2 values were normalized to GAPDH and oligonucleotide concentrations resulting in 50% reduction of TGF-beta2 mRNA (=$IC_{50}$ values) were calculated. Under gymnotic delivery experimental conditions, the oligonucleotides enter the cells and strongly inhibit the expression of TGF-beta2 mRNA. The results of the experiments are shown in Table 4:

| Name | IC50 (µM) |
| --- | --- |
| ASPH_047 | 0.76 |
| ASPH_190 | 0.18 |
| ASPH_191 | 0.97 |
| ASPH_192 | 0.145 |
| ASPH_193 | 0.144 |

All the modified oligonucleotides show an $IC_{50}$ in the submicromolar to lower submicromolar range, showing that they have extremely high potency even without the requirement of a transfection reagent.

Example 12

Figure 13:
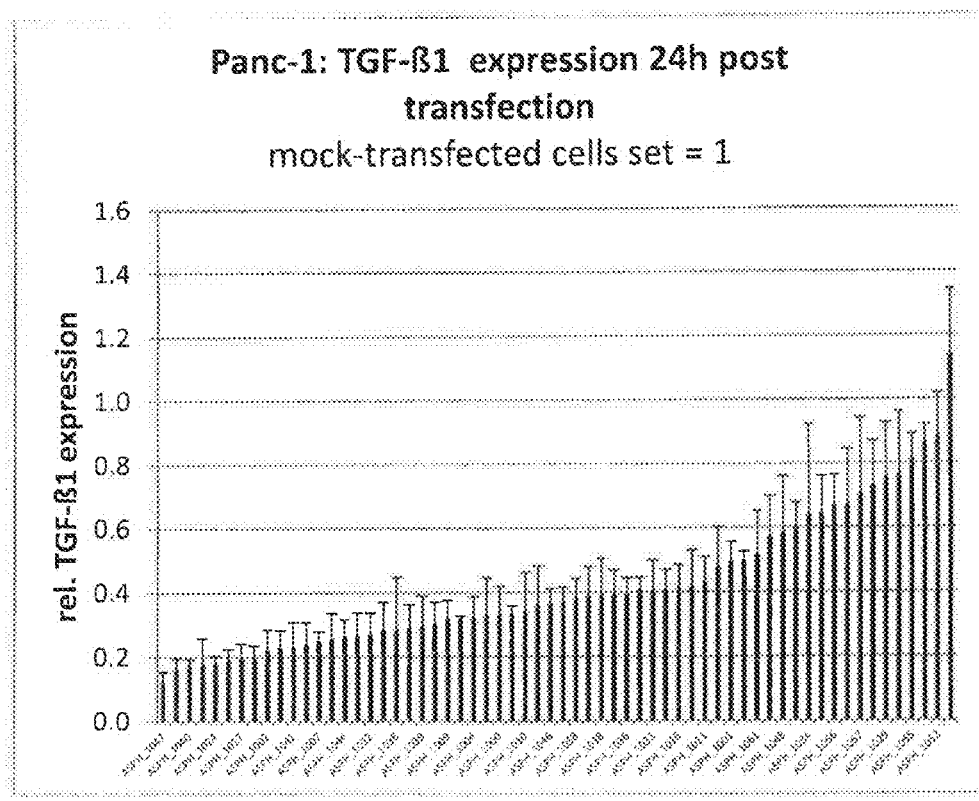
FIG. 13 depicts the inhibition of the expression of TGF-beta1 mRNA in human Panc-1 pancreatic cancer cells. Panc-1 cells were transfected with different modified oligonucleotides in a dose of 10 nM (in the presence of a transfecting agent), and inhibition of the TGF-beta1 mRNA expression was measured 24 h after transfection.

Human Panc-1 pancreatic cancer cells were transfected with 10 nM of ASPH05, ASPH09, ASPH1000, ASPH1001, ASPH1002, ASPH1003, ASPH1004, ASPH1005, ASPH1006, ASPH 1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH 1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1054, ASPH1055, ASPH1056, ASPH1057, ASPH1058, ASPH1059, ASPH1060, or ASPH1061 and the control of SEQ ID NO. 145, respectively, in the presence of a transfecting agent. The expression of TGF-beta1 mRNA was determined 24 h after transfection. Significant reduction of the expression of TGF-beta1 in Panc-1 cells is shown in FIG. 13.

Example 13

Figure 14:
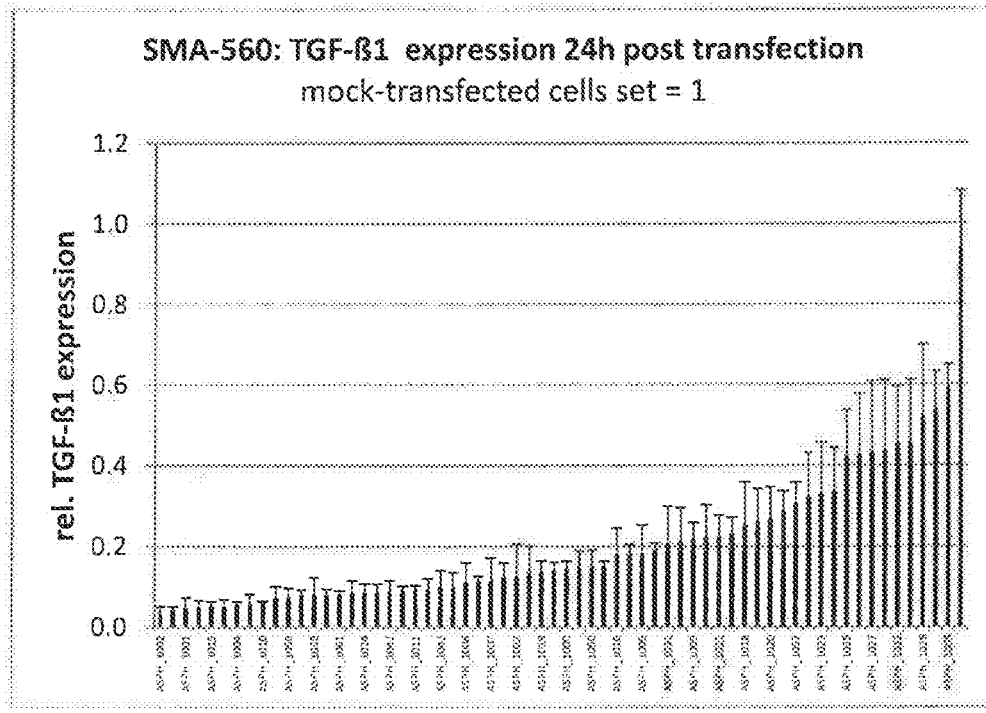
FIG. 14 shows the inhibition of the expression of TGF-beta1 mRNA in mouse SMA-560 glioma cells. Cells were transfected with different modified oligonucleotides in a dose of 10 nM (in the presence of a transfecting agent), and inhibition of the TGF-beta1 mRNA expression was measured 24 h after transfection.

Mouse SMA-560 glioma cells were transfected with 10 nM of ASPH09, ASPH1000, ASPH1001, ASPH1002, ASPH1003, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, or ASPH1062 and the control of SEQ ID NO. 145, respectively, in the presence of a transfecting agent. The expression of TGF-beta1 mRNA was determined 24 h after transfection. Significant reduction of the expression of TGF-beta1 in SMA-560 cells is shown in FIG. 14.

Example 14

Figure 15:
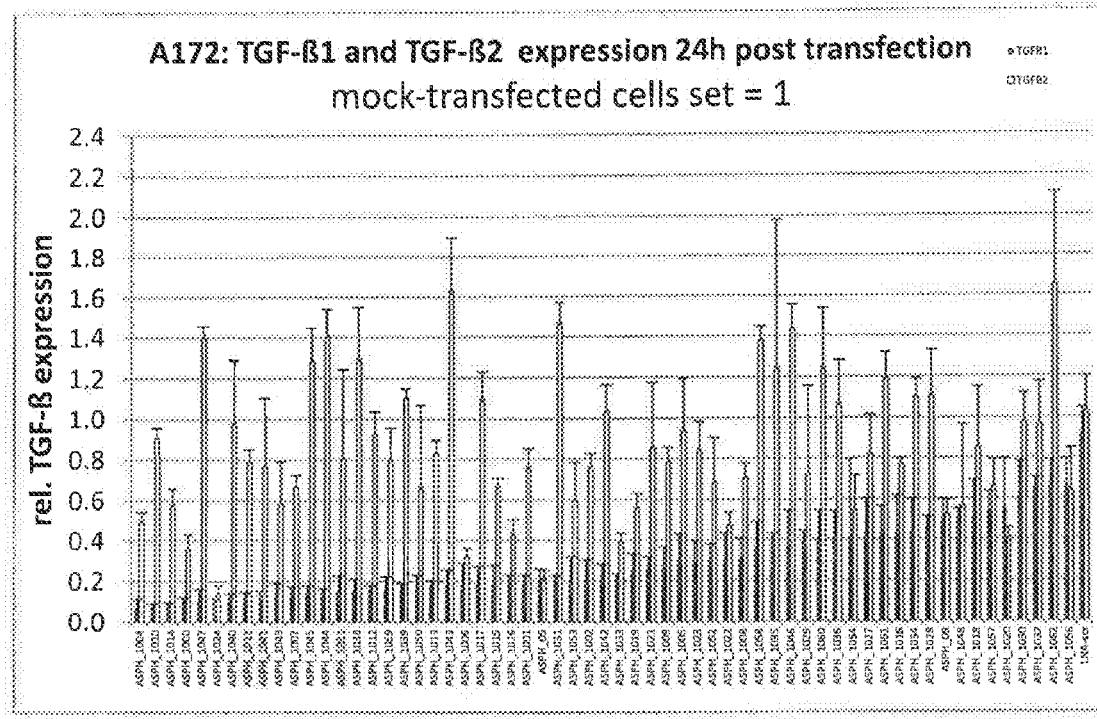
FIG. 15 depicts the inhibition of the expression of TGF-beta1 and TGF-beta2 mRNA in human A172 cells. Cells were transfected with different modified oligonucleotides in a dose of 10 nM (in the presence of a transfecting agent), and inhibition of the TGF-beta1 and TGF-beta2 mRNA expression was measured 24 h after transfection.

In these experiments, human A172 glioma cells were transfected with 10 nM of ASPH05, ASPH09, ASPH1000, ASPH1001, ASPH1002, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1056, ASPH1057, ASPH1058, ASPH1059, ASPH1060, ASPH1061, or ASPH1062, and the control of SEQ ID NO. 145, respectively, in the presence of a transfecting agent. The expression of TGF-beta1 and TGF-beta2 mRNA was determined 24 h after transfection. Significant reduction of the expression of TGF-beta1 mRNA is shown in FIG. 15. The dual TGF-beta1 and TGF-beta2 reactive oligonucleotides ASPH05 shows a significant reduction of the expression of both TGF-beta1 and TGF-beta2 mRNAs, while the selective TGF-beta1 oligonucleotides significantly inhibit TGF-beta1 mRNA expression.

Example 15

Figure 16:
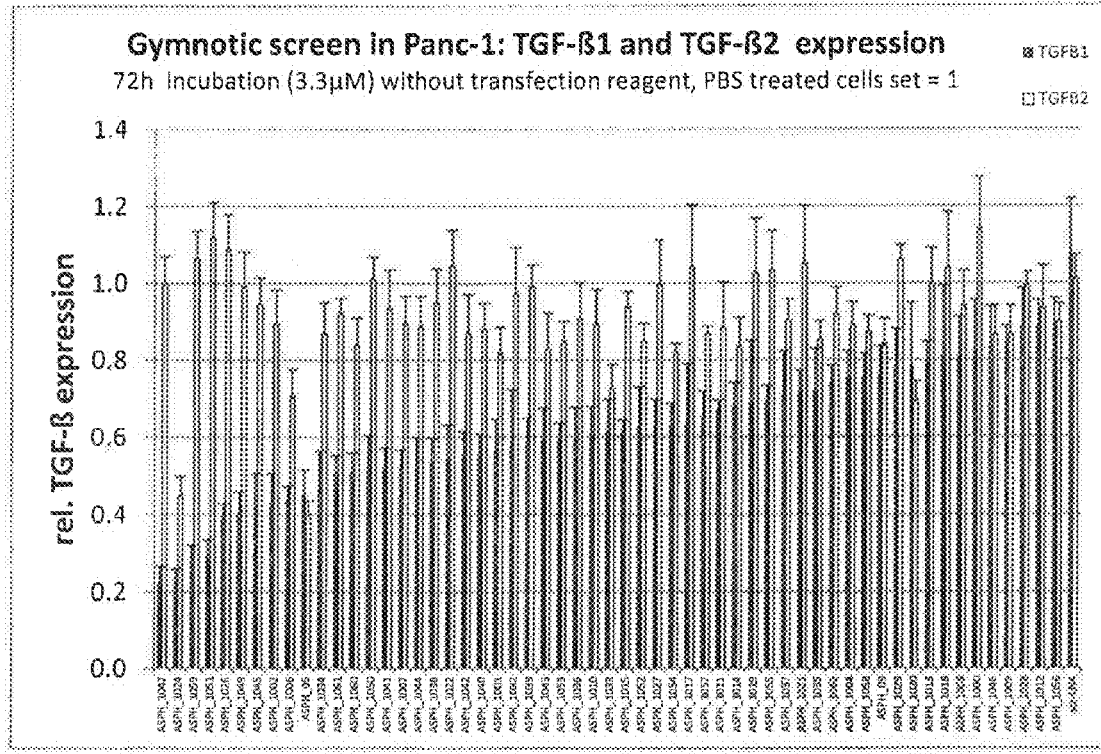
FIG. 16 shows the inhibition of the expression of TGF-beta1 and TGF-beta2 mRNA in Panc-1 cells. Panc-1 cells were treated with different modified oligonucleotides in a dose of 3.3 µM in the absence of any transfection reagent (gymnotic transfection or unassisted transfection or gymnotic delivery), and inhibition of the TGF-beta1 (black columns) and TGF-beta2 (white columns) mRNA expression was measured after 72 h.

Human Panc-1 pancreatic cancer cells were treated with 3.3 µM of ASPH05, ASPH09, ASPH1000, ASPH1001, ASPH1002, ASPH1004, ASPH1006, ASPH1007, ASPH1008, ASPH1009, ASPH1010, ASPH1011, ASPH1012, ASPH1013, ASPH1014, ASPH1015, ASPH1017, ASPH1018, ASPH1019, ASPH1020, ASPH1021, ASPH1022, ASPH1024, ASPH1026, ASPH1027, ASPH1028, ASPH1029, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, or ASPH1062, or the control of SEQ ID NO. 145 in the absence of a transfecting agent (gymnotic transfection or gymnotic delivery). The inhibitory effect of the modified oligonucleotides on expression of TGF-beta1 and TGF-beta2 mRNA, respectively, was determined 72 h after treatment start. Significant reduction of the expression of TGF-beta1 mRNA is shown in FIG. 16. The dual TGF-beta1 and TGF-beta2 reactive oligonucleotides ASPH05 shows a significant reduction of the expression of both TGF-beta1 and TGF-beta2 mRNAs, while the selective TGF-beta1 oligonucleotides significantly inhibit TGF-beta1 mRNA expression.

Example 16

Figure 17:
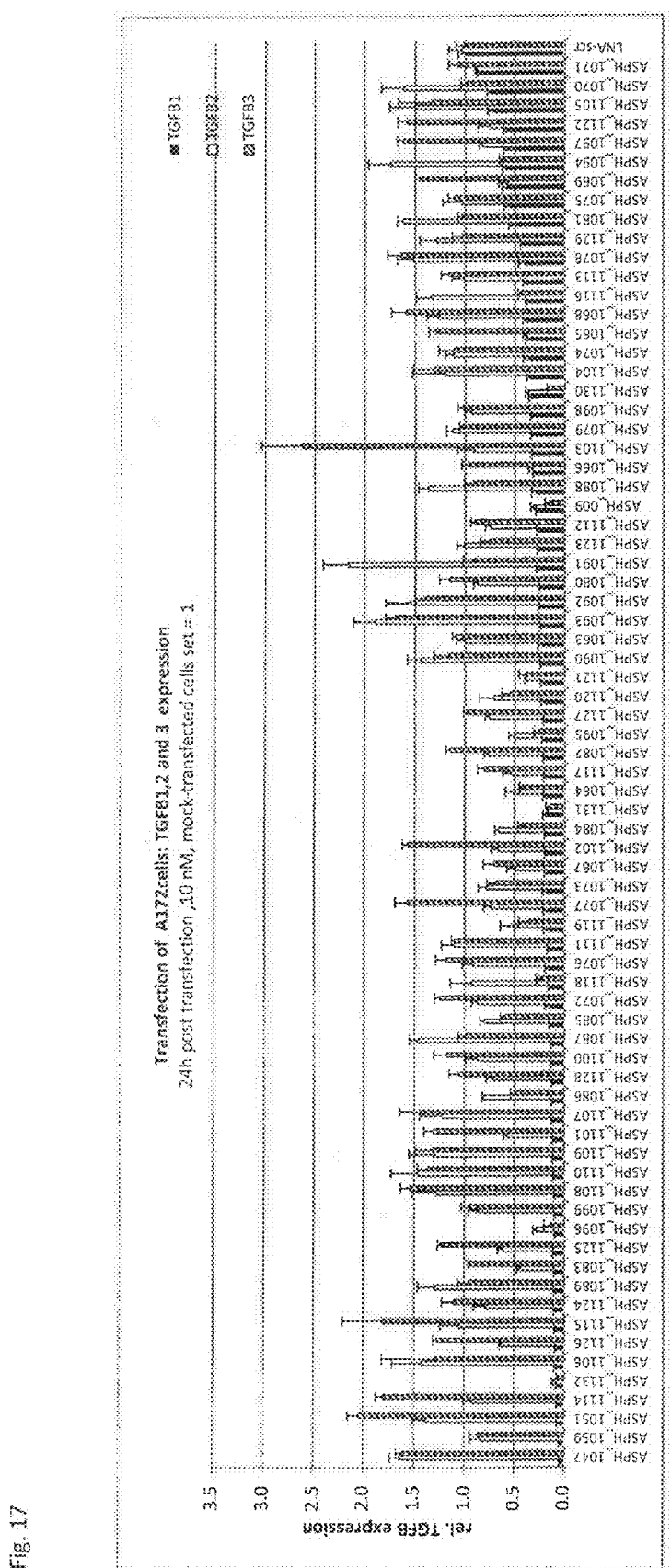
FIG. 17 depicts the inhibition of the expression of TGF-beta1, TGF-beta2 and TGF-beta3 mRNA in human A172 cells. Cells were transfected with different modified oligonucleotides in a dose of 10 nM (in the presence of a transfecting agent), and inhibition of the TGF-beta1 (black column), TGF-beta2 (white column) and TGF-beta3 (striped column) mRNA expression was measured 24 h after transfection.

Human A172 glioma cells were treated with 10 nM (in the presence of a transfecting agent), of ASPH09, ASPH1047, ASPH1051, ASPH1059, ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH1114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132, respective1, or the positive control ASPH1047. The expression of TGF-beta1 (black column), TGF-beta2 (white column) and TGF-beta3 (striped column) mRNA was determined 24 h after transfection. Significant reduction of the expression of TGF-beta1 mRNA is shown in FIG. 17. The pan-specific TGF-beta1, TGF-beta2 and TGF-beta3 reactive oligonucleotides ASPH0009, ASPH1096, ASPH1131, and ASPH1132 show a significant reduction of the expression of all three isoforms, while the selective TGF-beta1 oligonucleotides significantly inhibit TGF-beta1 mRNA expression.

Example 17

Figure 18A:
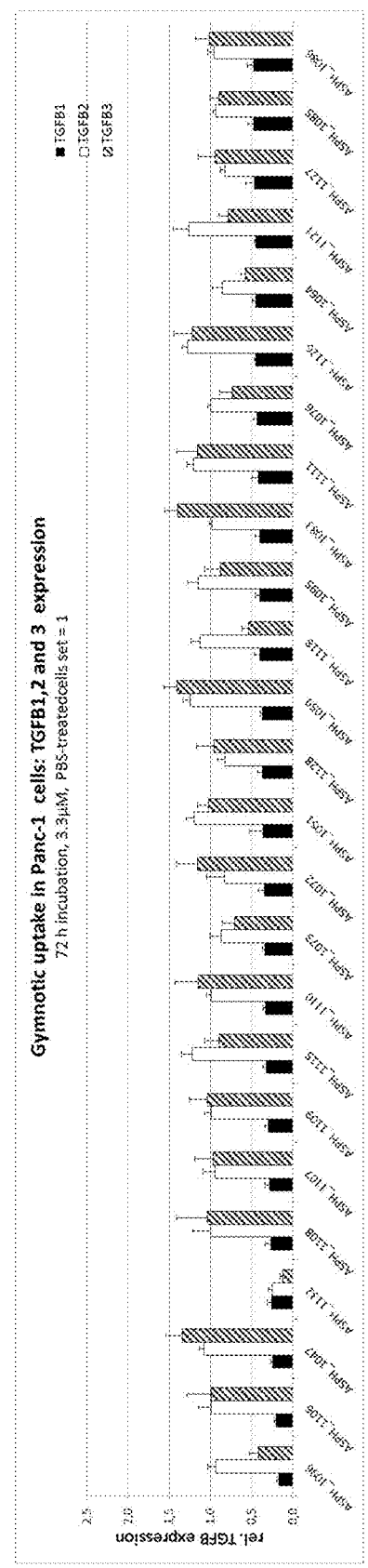
FIG. 18a(i), FIG. 18a(ii), and FIG. 18a(iii) shows the inhibition of the expression of TGF-beta1, TGF-beta2 and TGF-beta3 mRNA in human Panc-1 and RenCa cells. Cells were transfected with different modified oligonucleotides in a dose of 3.3 µM in the absence of any transfection reagent (gymnotic transfection or unassisted transfection or gymnotic delivery), and inhibition of the TGF-beta1 (black column), TGF-beta2 (white column) and TGF-beta3 (striped column) mRNA expression was measured 72 h after transfection.

Either human Panc-1 pancreatic cancer cells (FIG. 18a(i), FIG. 18a(ii), and FIG. 18a(iii)) or mouse RenCa renal cell carcinoma cells (FIG. 18a(i), FIG. 18a(ii), and FIG. 18a(iii)) were treated with 3.3 µM of ASPH09, ASPH1047, ASPH1051, ASPH1059, ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH1114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132, respectively, or the positive control ASPH1047 in the absence of a transfecting agent (gymnotic transfection or gymnotic delivery). The expression of TGF-beta1 (black column), TGF-beta2 (white column) and TGF-beta3 (striped column) mRNA was determined 72 h after transfection. Significant reduction of the expression of TGF-beta1 mRNA is shown in FIG. 17. The pan-specific TGF-beta1, TGF-beta2 and TGF-beta3 reactive oligonucleotides ASPH0009, ASPH1096, ASPH1131, and ASPH1132 show significant reduction of the expression of all three isoforms, while the selective TGF-beta1 oligonucleotides significantly inhibit TGF-beta1 mRNA expression.

Example 18

Mice bearing human Panc-1 pancreatic carcinoma subcutaneous tumors were treated with 1, 3, 10, and 30 mg/kg of ASPH47 under various treatment schedules: Q1Dx1-d6 (single SC injection, termination 5 days later), Q1Dx5-d6 (daily SC injection for 5 days, termination 24 hours later), and Q1Dx5-d10 (daily SC injection for 5 days, termination 5 days later). There was a dose dependent down-regulation of TGF-beta2 mRNA in the kidney of these animals. TGF-beta2 down-regulation was persistent up to 5 days after the last treatment with ASPH47, even after only single administration. TGF-beta 2 expression was detected by bDNA assay (branched DNA assay, which is a sandwich nucleic acid hybridization method that uses bDNA molecules to amplify signal from captured target RNA) and normalized to GAPDH. As shown in FIG. 22, data—representing TGF-beta2 to GAPDH mRNA ratio—are shown as a box plot in which median values and min. and max. values are presented (data expressed as n=10, except n=9 for vehicle and 3 mg/kg Q1Dx1 d6 groups).

Example 19

Mice bearing human Panc-1 pancreatic carcinoma subcutaneous tumors on both left and right flanks were treated with a daily subcutaneous injection of 1, 5, 15 or 50 mg/kg oligonucleotides for five consecutive days. The tumors were collected 24 hours after the last treatment and snap frozen. TGF-beta mRNA expression in tumors was detected by bDNA assay. Data—representing TGF-beta2 to GAPDH mRNA ratio—are shown as a box plot in which median values and min. and max. values are presented (data expressed as n=5). TGF-beta2 mRNA was down-regulated in tumors treated with various oligonucleotides (FIG. 23). There was no significant TGF-beta1 mRNA down-regulation in those groups (data not shown).

Example 20

Figure 24:
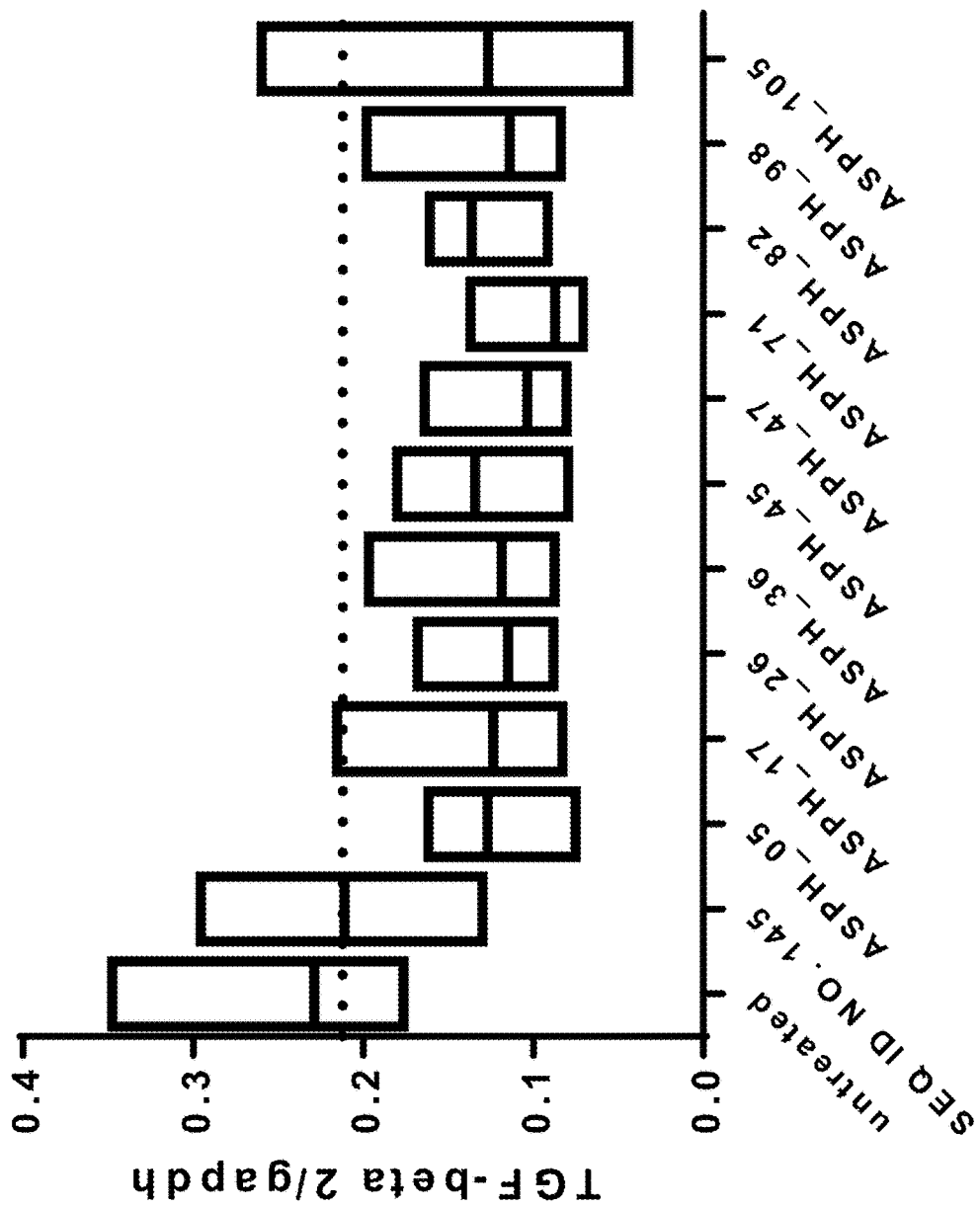
FIG. 24 presents TGF-beta2 mRNA expression in subcutaneous human renal cell carcinomas 786-0 tumors. Mice were treated with a daily injection of 50 mg/kg oligonucleotides for five consecutive days. TGF-beta2 and GAPDH mRNA expression was detected by bDNA. Data—representing TGF-beta2 to GAPDH mRNA ratio—are shown as a box plot in which median values and min. and max. values are presented (data expressed as n=10, except for ASPH71 group n=9).

Mice bearing human 786-0 renal cell carcinoma subcutaneous tumors on both left and right flanks were treated with a daily injection of 50 mg/kg oligonucleotides for five consecutive days. The tumors were collected 24 hours after the last treatment and snap frozen. TGF-beta mRNA expression in tumors was detected by bDNA assay. There was significant down-regulation of TGF-beta2 mRNA in tumors treated with ASPH05, ASPH17, ASPH26, ASPH36, ASPH45, ASPH47, ASPH71, ASPH82, ASPH98, and ASPH105 (FIG. 24). Data—representing TGF-beta2 to GAPDH mRNA ratio—are shown as a box plot in which median values and min. and max. values are presented (data expressed as n=10, except for ASPH71 group n=9).

Example 21

Human Panc-1 pancreatic cancer cells were transfected with 20, 6.67, 2.22, 0.74, 0.25, 0.08 or 0.009 µM of the modified oligonucleotides ASPH47, ASPH1047, ASPH1106, ASPH1132, or ASPH47 in combination with ASPH1047; results are shown in FIG. 26a to 26e). Negative control is the scrambled oligonucleotide (scrLNA) of SEQ ID No. 145 (FIG. 26f). All cells were transfected in the absence of transfecting agent (gymnotic transfection or gymnotic delivery). The modified oligonucleotides were added to the cells for 3 days, which were incubated at 37° C. Thereafter medium was exchanged with fresh oligonucleotide containing medium and cells were incubated for further 4 days at 37° C. TGF-beta1 and TGF-beta2 protein levels in cell supernatants were determined by ELISA. ASPH47 specifically inhibits the expression of TGF-beta2 in a dose-dependent manner and does not have any target inhibiting effect on TGF-beta1 (FIG. 26a). ASPH1047 specifically inhibits the expression of TGF-beta1 and does not have any target inhibiting effect on TGF-beta2 (FIG. 26b), or only a slight TGF-beta2 inhibiting effect at higher concentrations. Also ASPH1106 inhibits TGF-beta1 expression in a dose dependent manner (FIG. 26c). The pan-specific ASPH 1132 shows a dose-dependent inhibition of the expression of TGF-beta1 and TGF-beta2 protein (FIG. 26d). When ASPH47 and ASPH1047 are combined, the expression of both, TGF-beta1 and TGF-beta2 protein is inhibited in a dose dependent manner (FIG. 26e). The scrLNA of SEQ ID No. 145 does not show any inhibiting effect on the expression of neither TGF-beta1 nor TGF-beta2, even if the concentrations were doubled (40, 13.33, 4.44, 1.48, 0.49, 0.16, 0.05, or 0.02 µM) in comparison to the individual concentrations of ASPH47, ASPH1047, ASPH1106, or ASPH1132. Results for TGF-beta1 are indicated in diamonds, and results for TGF-beta2 in squares in FIGS. 26a to 26f.

Example 22

Figure 27A:
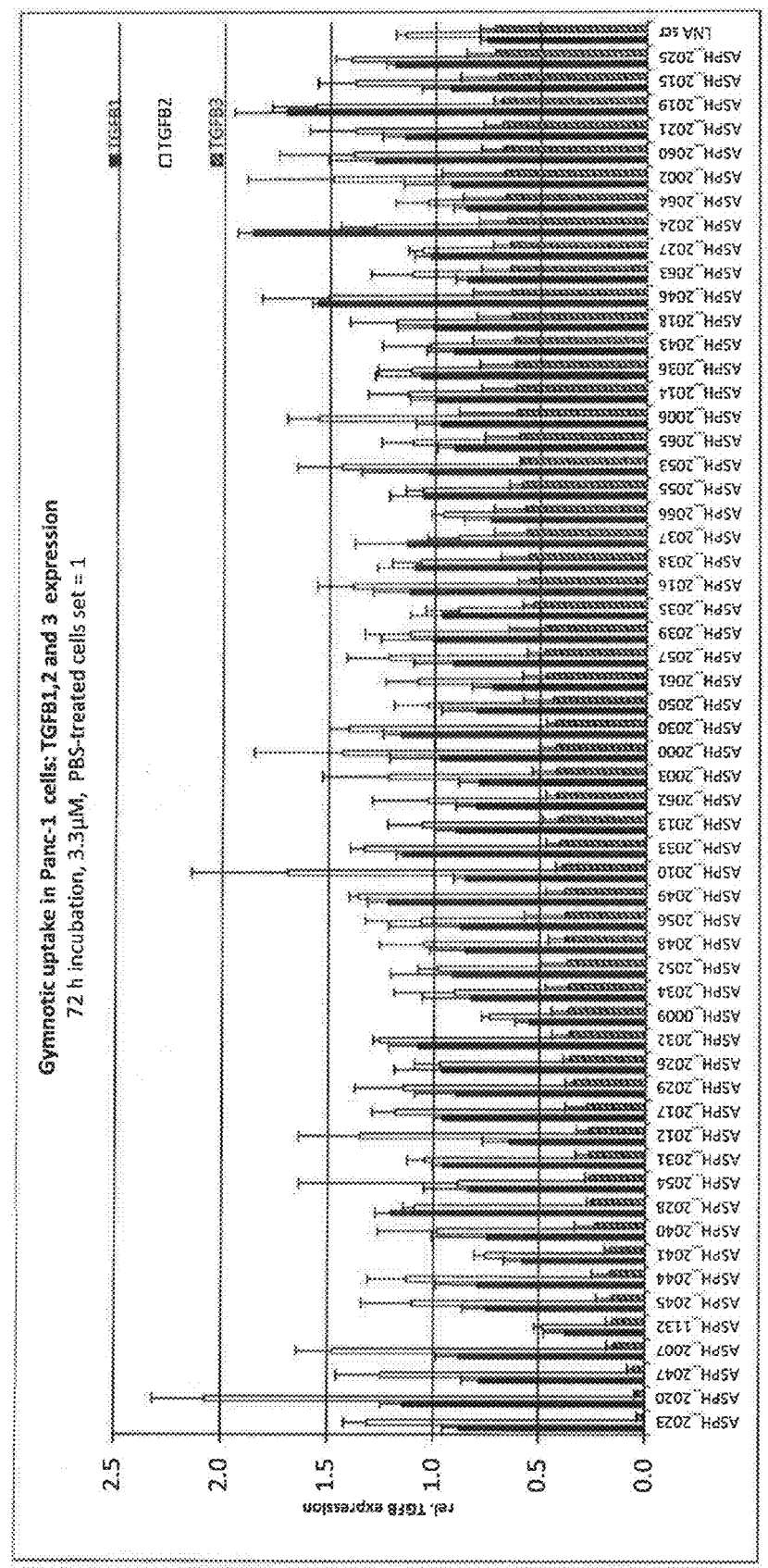
FIG. 27 presents the inhibiting effect of oligonucleotides of the present invention on the expression of TGF-beta1, TGF-beta2, and TGF-beta3. Panc-1 cells (FIG. 27a) or RenCa cells (FIG. 27b) were transfected with 3.3 µM of different TGF-beta specific oligonucleotides in the absence of a transfecting agent. The expression of TGF-beta1 (black column), TGF-beta2 (white column) and TGF-beta3 (striped column) mRNA was determined 72 h after transfection.
Figure 27B:
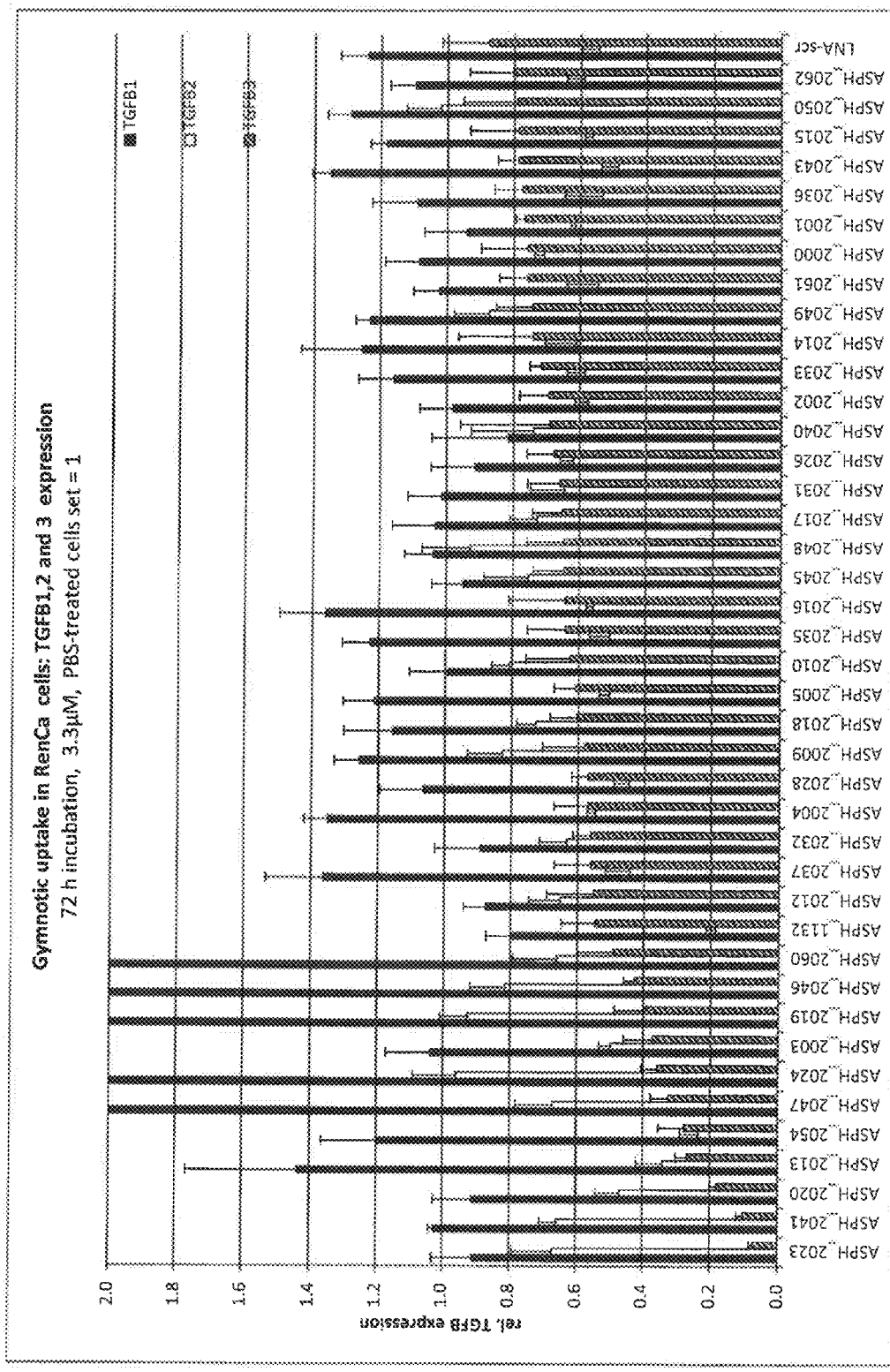

Human Panc-1 pancreatic cancer cells (FIG. 27a) or mouse RenCa renal cell carcinoma cells (FIG. 27b) were treated with 3.3 µM of ASPH0009, ASPH1132, ASPH2000, ASPH2001, ASPH2002, ASPH2003, ASPH2004, ASPH2005, ASPH2006, ASPH2007, ASPH2009, ASPH2010, ASPH2012, ASPH2013, ASPH2014 ASPH2015, ASPH2016, ASPH2017, ASPH2018, ASPH2019, ASPH2020, ASPH2021, ASPH2023, ASPH2024, ASPH2025, ASPH23026, ASPH2027, ASPH2028, ASPH2029, ASPH2030, ASPH2031, ASPH2032, ASPH2033, ASPH2034, ASPH2035, ASPH2036, ASPH2037, ASPH2038, ASPH2039, ASPH2040, ASPH2041, ASPH2043, ASPH2044, ASPH2045, ASPH2046, ASPH2047, ASPH2048, ASPH2049, ASPH2050, ASPH2052, ASPH2053, ASPH2054, ASPH2055, ASPH2056, ASPH2057, ASPH2060, ASPH2061, ASPH2062, ASPH2063, ASPH2064, ASPH2065, or ASPH2066 in the absence of a transfecting agent (gymnotic transfection or gymnotic delivery). The expression of TGF-beta1 (black column), TGF-beta2 (white column) and TGF-beta3 (striped column) mRNA was determined 72 h after transfection. Significant reduction of the expression of TGF-beta3 mRNA is shown in FIGS. 27a and 27b. As anticipated from the sequences, the TGF-beta1, -beta2 and -beta3 reactive oligonucleotide ASPH_0009 (pan-selective) and ASPH_1132 that has 100% homology to mRNAs of human TGF-beta1 and -beta3 but has a mismatch to TGF-beta2 show significant reduction of the expression of all three isoforms. The selective TGF-beta3 oligonucleotides only significantly inhibit TGF-beta3 mRNA expression.

Example 23

Human A172 glioma cells were treated for 24 h with 10 nM (in the presence of a transfecting agent), of ASPH0009, ASPH1132, ASPH2000, ASPH2001, ASPH2002, ASPH2003, ASPH2004, ASPH2006, ASPH2007, ASPH2008, ASPH2009, ASPH2010, ASPH2011, ASPH2012, ASPH2013, ASPH2014, ASPH2016, ASPH2017, ASPH2018, ASPH2020, ASPH2021, ASPH2022, ASPH2023, ASPH2024, ASPH2025, ASPH2026, ASPH2027, ASPH2028, ASPH2029, ASPH2030, ASPH2031, ASPH2032, ASPH2033, ASPH2034, ASPH2035, ASPH2036, ASPH2037, ASPH2038, ASPH2039, ASPH2040, ASPH2041, ASPH2042, ASPH2043, ASPH2044, ASPH2045, ASPH2047, ASPH2049, ASPH2050, ASPH2051, ASPH2052, ASPH2053, ASPH2054, ASPH2056, ASPH2057, ASPH2058, ASPH2059, ASPH2060, ASPH2061, ASPH2062, ASPH2063, or ASPH2066. The expression of TGF-beta1 (black column), TGF-beta2 (white column) and TGF-beta3 (striped column) mRNA was then determined from cell extracts by bDNA assay. Significant reduction of the expression of TGF-beta3 mRNA is shown in FIG. 28. As anticipated from the sequences, the TGF-beta1, -beta2 and -beta3 reactive oligonucleotide) ASPH_0009 (pan-selective) and ASPH_1132 that has 100% homology to mRNAs of human TGF-beta1 and -beta3 but has a mismatch to TGF-beta2 show significant reduction of the expression of all three isoforms. The selective TGF-beta3 oligonucleotides only significantly inhibit TGF-beta3 mRNA expression.

Example 24

Target mRNA Downregulation in Rabbit Cells

Sequences of selected oligonucleotides were aligned with rabbit mRNA sequences of TGF-beta1 and 2. ASPH_0036 (TGF-beta2 selective antisense oligonucleotide, based on human mRNA sequence) showed 100% homology with rabbit TGF-beta2 mRNA, while ASPH_1059 (TGF-beta1 selective antisense oligonucleotide, based on human mRNA sequence) showed 100% homology with rabbit TGF-beta1 mRNA.

Rabbit Rab-9 skin fibroblasts were treated with 5 nM or 20 nM of either ASPH_0036 and ASPH_1059 in the presence of a transfecting agent for 24 hr. The expression of TGF-beta1 and TGF-beta2 mRNA was then determined in cell extracts by bDNA assay. Significant reduction of the expression of TGF-beta1 mRNA (51 and 77% at 5 and 20 nM, respectively) was achieved with ASPH_1059. Significant reduction of TGF-beta2 mRNA (79 and 80% at 5 and 20 nM, respectively) was achieved with ASPH_0036.

Example 25

Tissue Biodistribution and Target mRNA Downregulation Following Systemic Administration of ASPH_0047 in Balb/c Mice Balb/C mice were treated with a single subcutaneous injection of ASPH_0047 (formulated in sterile physiological saline) at 5, 20 and 50 mg/kg animal body weight. Plasma and tissues were collected at the indicated times (from 3 individual animals), immediately snap-frozen and stored at −80° C. until analysis with an AEX-HPLC method (plasma/tissue PK) or for measurement of TGF-β2 and GAPDH mRNA levels by bDNA assay. TGF-β2 mRNA levels were expressed relative to GAPDH mRNA expression level in corresponding samples.

The data depict that a single subcutaneous bolus administration of 50 mg/kg ASPH_0047 resulted in rapid transfer of the drug from subcutaneous to circulating blood compartments ($T_{MAX}$ of ~5-30 min), biphasic pharmacokinetic profile in plasma, with rapid initial elimination phase (within the first 24 hrs), followed by long terminal half-life (FIG. 29a). It is further demonstrated that a marked long-lasting accumulation of the drug in various selected tissues. The major target organ (highest exposure/$C_{MAX}$) is the kidney, then the liver, skin and spleen, and lowest in the brain (data not shown). As also depicted in FIG. 29b, ASPH_0047 remained in the kidney tissue with pharmacological relevant doses (~50 µg/gr, equivalent to 10 µM) from 24 h and for up to 14 days, with consequent long-lasting and marked suppression of TGF-β2 mRNA expression in the kidney tissue, with effective ~80% target mRNA downregulation observed for at least 14 days.

Example 26

Immunodeficient mice were injected subcutaneously with human 786-O renal cell carcinoma cells (FIG. 30A), pancreatic Panc1 cancer cells (FIG. 30B, C), or mouse SMA-560 glioma cells (FIG. 30D). When subcutaneous tumors reached the size of 100-300 mm³ (established tumors), animals were treated subcutaneously, Q1Dx5, with saline (Mock), control oligonucleotide (Control; 50 mg/kg), inactive oligonucleotides in this context (e.g., ASPH_0065 and ASPH_0071; 50 mg/kg) or ASPH_0047 at 50 mg/kg, or the indicated doses. Tumors (FIG. 30A-D) and kidneys (FIG. 30E-F) were collected 24 hr after the last administration. Tumors/kidneys were then further processed for determination of TGF-□2 and GAPDH mRNA levels by bDNA assay. In these experiments, control oligonucleotide was a 18-mer, 3+3 LNA gapmer scrambled sequence. Results are expressed as TGF-beta2/GAPDH mRNA ratio, and each individual tested sample is represented with median values indicated as red line. Under described experimental conditions (schedule and route of administration), systemic repeated administrations of ASPH_0047 in Balb/c mice led to a sequence-specific downregulation of TGF-beta 2 mRNA in established subcutaneous tumors and kidneys.

Example 27

Balb/c mice were injected with mouse Renca cells into renal subcapsule (FIG. 31A, B) or i.v. (FIG. 31C, D) on Day 0. Systemic treatment with vehicle or indicated oligonucleotides started on Day 7 (FIG. 31A; 50 mg/kg, s.c., twice weekly), on Day 1 (FIG. 31B; 12.5 mg/kg, s.c., twice weekly) for two consecutive weeks, or on Day 7 (FIGS. 31C and 31D; indicated doses, s.c., twice weekly) for 26-27 days. Number of lung metastasis was macroscopically evaluated, and level of lung metastasis was determined by either number of metastasis (FIG. 31A, C) or based on lung weight (FIG. 31B, D). Results are represented as box plot; with median values, upper and lower quartiles, and 90th and 10th percentiles. Under described experimental designs, Balb/c mice treated with ASPH_0047 showed a reduced number of lung metastasis or reduced lung weight (lung weight correlates to extent of lung metastasis) in mouse Renca RCC models.

Example 28

Human Panc-1 pancreatic cancer cells were treated with 3.3 µM of the indicated oligonucleotides in the absence of transfecting agent (gymnotic transfection or gymnotic delivery). The expression of TGF-beta1 (black column), TGF-beta2 (white column) and TGF-beta3 (striped column) mRNA was determined 72 h after transfection. Significant reduction of the expression of TGF-beta1 mRNA is shown in FIG. 32. The selective TGF-beta1 oligonucleotides only significantly inhibit TGF-beta1 mRNA expression while the control oligonucleotide LNA-scr does not affect expression of any TGF-beta isoform.

Example 29

Balb/c mice were injected with mouse 4T1 cells into mammary fat pad on Day 0. Systemic treatment with saline (Mock), pan-TGF-beta antibody (1D11), control oligonucleotide (LNA-scr), or ASPH_0047 started on Day 3 (30 mg/kg, s.c., twice weekly) and continued until D28, when animals were sacrificed. Number of lung metastasis was macroscopically evaluated, and level of lung metastasis was determined by either number of metastasis (left panel) or based on lung weight (right panel). Under described experimental design, treatment with ASPH_0047 reduced metastasis to the lungs, whereas the positive control, monoclonal TGF-beta antibody 1D11 had no effect on pulmonary metastasis in this model.

Example 30

CB17 SCID or Balb/c nude mice (n=3-5, except ASPH_0018 n=1 and ASPH_0037 n=2) were treated with 14-15 mg/kg of indicated LNA-modified oligonucleotides for four or five consecutive days (Q1Dx4-5). Plasma was collected 24 h after the last treatment and ALT levels were determined in plasma. Results are expressed as median values. Under this experimental condition, only 6/48 (12.5%) of tested oligonucleotides induced marked increase in plasma ALT (>300 units/l) indicating liver toxicity. The following Table 7 shows liver toxicity of systemically administered LNA-modified oligonucleotides:

| Name | ALT (units/l) |
|---|---|
| ASPH_0001 | 20.5 |
| ASPH_0003 | 20.0 |
| ASPH_0005 | 33.0 |
| ASPH_0009 | 834.0 |
| ASPH_0017 | 55.0 |
| ASPH_0018 | 7723.0 |
| ASPH_0022 | 28.5 |
| ASPH_0026 | 77.0 |
| ASPH_0027 | 75.0 |
| ASPH_0035 | 25.0 |
| ASPH_0036 | 131.5 |
| ASPH_0037 | 161.0 |
| ASPH_0041 | 655.0 |
| ASPH_0045 | 27.5 |
| ASPH_0046 | 3199.0 |
| ASPH_0047 | 42.5 |
| ASPH_0048 | 29.5 |
| ASPH_0065 | 27.0 |
| ASPH_0069 | 32.5 |
| ASPH_0071 | 23.5 |
| ASPH_0080 | 34.0 |
| ASPH_0082 | 31.0 |
| ASPH_0098 | 33.0 |
| ASPH_0105 | 40.0 |
| ASPH_0115 | 985.5 |
| ASPH_0190 | 902.0 |
| ASPH_0191 | 36.5 |
| ASPH_0192 | 49.5 |
| ASPH_0193 | 35.0 |
| ASPH_0005_C1 | 25.5 |
| ASPH_0005_C2 | 35.5 |
| ASPH_0005_C3 | 25.0 |
| ASPH_0036_C1 | 34.0 |
| ASPH_0036_C2 | 26.0 |
| ASPH_0036_C3 | 39.0 |
| ASPH_0045_C1 | 38.5 |
| ASPH_0045_C2 | 23.5 |
| ASPH_0045_C3 | 65.0 |
| ASPH_0047_C1 | 35.5 |
| ASPH_0047_C2 | 30.0 |
| ASPH_0047_C3 | 29.5 |

-continued

| Name | ALT (units/l) |
|---|---|
| ASPH_0047_C4 | 52.5 |
| ASPH_0047_C5 | 28.0 |
| ASPH_0047_C6 | 33.5 |
| ASPH_0047_C7 | 37.0 |
| ASPH_0047_C8 | 32.0 |
| ASPH_0047_C9 | 49.0 |
| ASPH_0047_C10 | 32.5 |

EMBODIMENTS

1. Oligonucleotide consisting of 12 to 18 nucleotides of the TGF-beta2 nucleic acid sequence of SEQ ID NO. 1, wherein one or more nucleotide(s) of the oligonucleotide is/are a LNA modified, wherein the modified nucleotide is a LNA, and/or an ENA, polyalkylene oxide-, 2'-fluoro-, 2'-O-methoxy-, and/or 2'O-methyl-modified nucleotide.

2. Oligonucleotide according to embodiment 1 consisting of 12 to 18 nucleotides of the region of nucleic acid no. 1380 to 1510, no. 1660 to 1680, no. 2390 to 2410, or no. 2740 to 2810 of the TGF-beta2 nucleic acid sequence of SEQ ID NO. 1.

3. Oligonucleotide according to any one of embodiments 1 or 2, wherein the modified nucleotide is located at the 5'- and/or 3'- end of the oligonucleotide.

4. Oligonucleotide according to any one of embodiments 1 to 3, wherein the oligonucleotide comprises a sequence selected from the group consisting of SEQ ID NO. 46, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 12, SEQ ID NO. 13, SEQ ID NO. 14, SEQ ID NO. 15, SEQ ID NO. 16, SEQ ID NO.17, SEQ ID NO. 18, SEQ ID NO. 25, SEQ ID NO. 31, SEQ ID NO. 35, SEQ ID NO. 44, SEQ ID NO. 47, SEQ ID NO. 57, SEQ ID NO. 61, SEQ ID NO. 63, SEQ ID NO. 73, SEQ ID NO. 95, and SEQ ID NO. 103.

5. Oligonucleotide according to embodiment 1 or 4, wherein the oligonucleotide is selected from the group consisting of CAAAGTATTTGGTCTCC (ASPH47), ACCTCCTTGGCGTAGTA (ASPH01), ACCTCCTTGGCGTAGTA (ASPH02), CCTCCTTGGCGTAGTA (ASPH03), CCTCCTTGGCGTAGTA (ASPH04), CTCCTTGGCGTAGTA (ASPH05), CTCCTTGGCGTAGTA (ASPH06), CTCCTTGGCGTAGTA (ASPH07), TCCTTGGCGTAGTA (ASPH08), CAGAAGTTGGCAT (ASPH09), CAGAAGTTGGCAT (ASPH10), CTGCCCGCGGAT (ASPH15), TCTGCCCGCGGAT (ASPH17), TCGCGCTCGCAGGC (ASPH22), GGATCTGCCCGCGGA (ASPH26), GGATCTGCCCGCGGA (ASPH27), CGATCCTCTTGCGCAT (ASPH30), GGCGGGATGGCAT (ASPH35), GACCAGATGCAGGA (ASPH36), CTTGCTCAGGATCTGCC (ASPH37), TCTGTAGGAGGGC (ASPH45), CCTTAAGCCATCCATGA (ASPH48), TCTGAACTAGTACCGCC (ASPH65), TACTATTATGGCATCCC (ASPH69), AGCGTAATTGGTCATCA (ASPH71), GCGACCGTGACCAGAT (ASPH80), AACTAGTACCGCCTTT (ASPH82), GCGCGACCGTGACC (ASPH98), ACCACTAGAGCACC (ASPH105), AGCGCGACCGTGA (ASPH111), GGATCGCCTCGAT (ASPH112), CTAGTACCGCCTT (ASPH115), CCGCGATCGCC (ASPH119), GACCGTGACCAGAT (ASPH121), GACCGTGACCAGAT (ASPH153).

6. Pharmaceutical composition comprising the oligonucleotide according to any one of embodiments 1 to 5 and a pharmaceutically acceptable carrier.

7. Oligonucleotide according to any one of embodiments 1 to 5 or pharmaceutical composition according to claim 6 for use in a method of preventing and/or treating a malignant and/or benign tumor, fibrosis, cirrhosis, scleroderma or related dermatologic diseases, or a CNS disease.

8. Oligonucleotide or pharmaceutical composition for use according to embodiment 7, wherein the tumor is selected from the group consisting of solid tumors, blood born tumors, leukemias, tumor metastasis, hemangiomas, acoustic neuromas, neurofibromas, trachomas, pyogenic granulomas, psoriasis, astrocytoma, acoustic neuroma, blastoma, Ewing's tumor, craniopharyngloma, ependymoma, medulloblastoma, glioma, hemangloblastoma, Hodgkins-lymphoma, medullablastoma, leukaemia, mesothelioma, neuroblastoma, neurofibroma, non-Hodgkins lymphoma, pinealoma, retinoblastoma, sarcoma, seminoma, trachomas, Wilm's tumor, or is selected from the group of bile duct carcinoma, bladder carcinoma, brain tumor, breast cancer, bronchogenic carcinoma, carcinoma of the kidney, cervical cancer, choriocarcinoma, choroidcarcinoma, cystadenocarcinome, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostata cancer, small intestine carcinoma, prostate carcinoma, rectal cancer, renal cell carcinoma, retinoblastoma, skin cancer, small-cell bronchogenic/lung carcinoma, squamous cell carcinoma, sebaceous gland carcinoma, testicular carcinoma, and uterine cancer.

What is claimed is:

1. A method of inhibiting and/or treating a malignant and/or benign tumor, fibrosis, cirrhosis, scleroderma or related dermatologic diseases, or a CNS disease, comprising:
   administering an oligonucleotide to a subject in need thereof,
   wherein said oligonucleotide is:
   CAAAGTATTTGGTCTCC (SEQ. ID. NO. 47) wherein nucleotides in bold letters are LNA modified oligonucleotides, or
   GACCAGATGCAGGA (SEQ ID NO. 2).

2. The method of claim 1, wherein the method is directed to inhibiting and/or treating a malignant and/or benign tumor, and wherein the tumor is at least one of solid tumors, blood born tumors, leukemias, tumor metastasis, hemangiomas, acoustic neuromas, neurofibromas, trachomas, pyogenic granulomas, psoriasis, astrocytoma, acoustic neuroma, blastoma, Ewing's tumor, craniopharyngioma, ependymoma, medulloblastoma, glioma, hemangloblastoma, Hodgkins-lymphoma, medullablastoma, leukaemia, mesothelioma, neuroblastoma, neurofibroma, non-Hodgkins lymphoma, pinealoma, retinoblastoma, sarcoma, seminoma, trachomas, Wilm's tumor, bile duct carcinoma, bladder carcinoma, brain tumor, breast cancer, bronchogenic carcinoma, carcinoma of the kidney, cervical cancer, choriocarcinoma, choroidcarcinoma, cystadenocarcinome, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non- small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma, retinoblastoma, skin cancer, small-cell bronchogenic/lung carcinoma, squamous cell carcinoma, sebaceous gland carcinoma, testicular carcinoma, and uterine cancer.

3. A method of inhibiting and/or treating a malignant and/or benign tumor, fibrosis, cirrhosis, scleroderma or related dermatologic diseases, or a CNS disease, comprising:
   administering a pharmaceutical composition to a subject in need thereof, said pharmaceutical composition comprising:
   an oligonucleotide and a pharmaceutically acceptable carrier;
   wherein said oligonucleotide is:
   CAAAGTATTTGGTCTCC (SEQ. ID. NO. 47) wherein nucleotides in bold letters are LNA modified oligonucleotides, or
   GACCAGATGCAGGA (SEQ ID NO. 2).

4. The method of claim 3, wherein the method is directed to inhibiting and/or treating a malignant and/or benign tumor, and wherein the tumor is at least one of solid tumors, blood born tumors, leukemias, tumor metastasis, hemangiomas, acoustic neuromas, neurofibromas, trachomas, pyogenic granulomas, psoriasis, astrocytoma, acoustic neuroma, blastoma, Ewing's tumor, craniopharyngioma, ependymoma, medulloblastoma, glioma, hemangloblastoma, Hodgkins-lymphoma, medullablastoma, leukaemia, mesothelioma, neuroblastoma, neurofibroma, non-Hodgkins lymphoma, pinealoma, retinoblastoma, sarcoma, seminoma, trachomas, Wilm's tumor, bile duct carcinoma, bladder carcinoma, brain tumor, breast cancer, bronchogenic carcinoma, carcinoma of the kidney, cervical cancer, choriocarcinoma, choroidcarcinoma, cystadenocarcinome, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non- small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma, retinoblastoma, skin cancer, small-cell bronchogenic/lung carcinoma, squamous cell carcinoma, sebaceous gland carcinoma, testicular carcinoma, and uterine cancer.

5. The method of claim 1, wherein the method is directed to treating a malignant and/or benign tumor, fibrosis, cirrhosis, scleroderma or related dermatologic diseases, or a CNS disease.

6. The method of claim 3, wherein the method is directed to treating a malignant and/or benign tumor, fibrosis, cirrhosis, scleroderma or related dermatologic diseases, or a CNS disease.

7. The method of claim 1, wherein the oligonucleotide is CAAAGTATTTGGTCTCC (SEQ. ID. NO. 47) and wherein nucleotides in bold letters are LNA modified oligonucleotides.

8. The method of claim 1, wherein the oligonucleotide is GACCAGATGCAGGA (SEQ ID NO. 2).

9. The method of claim 3, wherein the oligonucleotide is CAAAGTATTTGGTCTCC (SEQ. ID. NO. 47) and wherein nucleotides in bold letters are LNA modified oligonucleotides.

10. The method of claim 3, wherein the oligonucleotide is GACCAGATGCAGGA (SEQ ID NO. 2).

* * * * *

SEQUENCE LISTING

```
<160> NUMBER OF SEQ ID NOS: 402

<210> SEQ ID NO 1
<211> LENGTH: 5882
<212> TYPE: DNA
<213> ORGANISM: Homo sapiens

<400> SEQUENCE: 1
gtgatgttat ctgctggcag cagaaggttc gctccgagcg gagctccaga agctcctgac       60
aagagaaaga cagattgaga tagagataga aagagaaaga gagaaagaga cagcagagcg      120
agagcgcaag tgaaagaggc aggggagggg gatggagaat attagcctga cggtctaggg      180
```

```
agtcatccag gaacaaactg aggggctgcc cggctgcaga caggaggaga cagagaggat    240
ctattttagg gtggcaagtg cctacctacc ctaagcgagc aattccacgt tggggagaag    300
ccagcagagg ttgggaaagg gtgggagtcc aagggagccc ctgcgcaacc ccctcaggaa    360
taaaactccc cagccagggt gtcgcaaggg ctgccgttgt gatccgcagg gggtgaacgc    420
aaccgcgacg gctgatcgtc tgtggctggg ttggcgtttg gagcaagaga aggaggagca    480
ggagaaggag ggagctggag gctggaagcg tttgcaagcg gcggcggcag caacgtggag    540
taaccaagcg ggtcagcgcg cgcccgccag ggtgtaggcc acggagcgca gctcccagag    600
caggatccgc gccgcctcag cagcctctgc ggccctgcg gcacccgacc gagtaccgag    660
cgccctgcga agcgcaccct cctccccgcg gtgcgctggg ctcgccccca gcgcgcgcac    720
acgcacacac acacacacac acacacacgc acgcacacac gtgtgcgctt ctctgctccg    780
gagctgctgc tgctcctgct ctcagcgccg cagtggaagg caggaccgaa ccgctccttc    840
tttaaatata taaatttcag cccaggtcag cctcggcggc cccctcacc cgcgctcccgg   900 cgcccctccc gtcagttcgc cagctgccag ccccgggacc ttttcatctc ttccctttg    960 gccggaggag ccgagttcag atccgccact ccgcacccga gactgacaca ctgaactcca   1020
cttcctcctc ttaaatttat ttctacttaa tagccactcg tctctttttt tccccatctc   1080
attgctccaa gaatttttt cttcttactc gccaaagtca gggttccctc tgcccgtccc    1140
gtattaatat ttccactttt ggaactactg gcctttctt tttaaaggaa ttcaagcagg    1200
atacgttttt ctgttgggca ttgactagat tgtttgcaaa agtttcgcat caaaaacaac    1260
aacaacaaaa aaccaaacaa ctctccttga tctatacttt gagaattgtt gatttctttt    1320
ttttattctg acttttaaaa acaactttt tttccactt tttaaaaaat gcactactgt     1380
gtgctgagcg cttttctgat cctgcatctg gtcacggtcg cgctcagcct gtctacctgc    1440
agcacactcg atatggacca gttcatgcgc aagaggatcg aggcgatccg cgggcagatc    1500
ctgagcaagc tgaagctcac cagtccccca gaagactatc ctgagcccga ggaagtcccc    1560
ccggaggtga tttccatcta caacagcacc agggacttgc tccaggagaa ggcgagccgg    1620
agggcggccg cctgcgagcg cgagaggagc gacgaagagt actacgccaa ggaggtttac    1680
aaaatagaca tgccgcccct cttcccctcc gaaaatgcca tcccgcccac tttctacaga    1740
ccctacttca gaattgttcg atttgacgtc tcagcaatgg agaagaatgc ttccaatttg    1800
gtgaaagcag agttcagagt ctttcgtttg cagaacccaa aagccagagt gcctgaacaa    1860
cggattgagc tatatcagat tctcaagtcc aaagatttaa catctccaac ccagcgctac    1920
atcgacagca aagttgtgaa acaagagca gaaggcgaat ggctctcctt cgatgtaact    1980
gatgctgttc atgaatggct tcaccataaa gacaggaacc tgggatttaa aataagctta    2040
cactgtccct gctgcacttt tgtaccatct aataattaca tcatcccaaa taaaagtgaa    2100
gaactagaag caagatttgc aggtattgat ggcacctcca catataccag tggtgatcag    2160
aaaactataa agtccactag gaaaaaaaac agtgggaaga cccacatctc ctgctaatg    2220 ttattgccct cctacagact tgagtcacaa cagaccaacc ggcggaagaa gcgtgctttg    2280
gatgcggcct attgctttag aaatgtgcag gataattgct gcctacgtcc actttacatt    2340
gatttcaaga gggatctagg gtggaaatgg atacacgaac ccaaagggta caatgccaac    2400
ttctgtgctg gagcatgccc gtatttatgg agttcagaca ctcagcacag cagggtcctg    2460
agcttatata ataccataaa tccagaagca tctgcttctc cttgctgcgt gtcccaagat    2520
ttagaaccct caaccattct ctactacatt ggcaaaacac ccaagattga acagctttct    2580
```

```
aatatgattg taaagtcttg caaatgcagc taaaattctt ggaaaagtgg caagaccaaa    2640
atgacaatga tgatgataat gatgatgacg acgacaacga tgatgcttgt aacaagaaaa    2700
cataagagag ccttggttca tcagtgttaa aaaattttg aaaaggcggt actagttcag     2760
acactttgga agtttgtgtt ctgtttgtta aaactggcat ctgacacaaa aaagttgaa     2820 ggccttattc tacatttcac ctactttgta agtgagagag acaagaagca aatttttttt    2880
aaagaaaaaa ataaacactg gaagaattta ttagtgttaa ttatgtgaac aacgacaaca    2940
acaacaacaa caacaaacag gaaaatccca ttaagtggag ttgctgtacg taccgttcct    3000
atcccgcgcc tcacttgatt tttctgtatt gctatgcaat aggcaccctt cccattctta    3060
ctcttagagt taacagtgag ttatttattg tgtgttacta tataatgaac gtttcattgc    3120
ccttggaaaa taaacaggt gtataaagtg gagaccaaat actttgccag aaactcatgg     3180
atggcttaag gaacttgaac tcaaacgagc cagaaaaaaa gaggtcatat taatgggatg    3240
aaaacccaag tgagttatta tatgaccgag aaagtctgca ttaagataaa gaccctgaaa    3300
acacatgtta tgtatcagct gcctaaggaa gcttcttgta aggtccaaaa actaaaaaga    3360
ctgttaataa aagaaacttt cagtcagaat aagtctgtaa gttttttttt tctttttaa     3420 ttgtaaatgg ttctttgtca gtttagtaaa ccagtgaaat gttgaaatgt tttgacatgt    3480
actggtcaaa cttcagacct taaaatattg ctgtatagct atgctatagg ttttttcctt    3540
tgttttggta tatgtaacca tacctatatt attaaaatag atggatatag aagccagcat    3600
aattgaaaac acatctgcag atctcttttg caaactatta aatcaaaaca ttaactactt    3660
tatgtgtaat gtgtaaattt ttaccatatt ttttatattc tgtaataatg tcaactatga    3720
tttagattga cttaaatttg ggctcttttt aatgatcact cacaaatgta tgtttctttt    3780
agctggccag tactttgag taaagcccct atagtttgac ttgcactaca aatgcatttt     3840 tttttaata acatttgccc tacttgtgct ttgtgtttct ttcattatta tgacataagc     3900
tacctgggtc cacttgtctt ttctttttt tgtttcacag aaaagatggg ttcgagttca     3960
gtggtcttca tcttccaagc atcattacta accaagtcag acgttaacaa atttttatgt    4020
taggaaaagg aggaatgtta tagatacata gaaaattgaa gtaaaatgtt ttcattttag    4080
caaggattta gggttctaac taaaactcag aatctttatt gagttaagaa aagtttctct    4140
accttggttt aatcaatatt tttgtaaaat cctattgtta ttacaaagag gacacttcat    4200
aggaaacatc ttttctttta gtcaggtttt taatattcag ggggaaattg aaagatatat    4260
attttagtcg atttttcaaa agggggaaaaa agtccaggtc agcataagtc attttgtgta    4320
tttcactgaa gttataaggt tttataaaat gttctttgaa ggggaaaagg cacaagccaa    4380
tttttcctat gatcaaaaaa ttcttctctt cctctgagtg agagttatct atatctgagg    4440
ctaaagttta ccttgcttta ataataatt tgccacatca ttgcagaaga ggtatcctca     4500
tgctggggtt aatagaatat gtcagtttat cacttgtcgc ttatttagct ttaaaataaa    4560
aattaatagg caaagcaatg gaatatttgc agtttcacct aaagagcagc ataaggaggc    4620
gggaatccaa agtgaagttg tttgatatgg tctacttctt ttttggaatt tcctgaccat    4680
taattaaaga attggatttg caagtttgaa aactggaaaa gcaagagatg ggatgccata    4740
atagtaaaca gcccttgtgt tggatgtaac ccaatcccag atttgagtgt gtgttgatta    4800 ttttttttgtc ttccactttt ctattatgtg taaatcactt ttatttctgc agacattttc    4860
ctctcagata ggatgacatt tgttttgta ttattttgtc tttcctcatg aatgcactga     4920
```

-continued

```
taatatttta aatgctctat tttaagatct cttgaatctg tttttttttt ttttaatttg    4980
ggggttctgt aaggtctttg tttcccataa gtaaatattg ccatgggagg ggggtggagg    5040
tggcaaggaa ggggtgaagt gctagtatgc aagtgggcag caattatttt tgtgttaatc    5100
agcagtacaa tttgatcgtt ggcatggtta aaaaatggaa tataagatta gctgttttgt    5160
attttgatga ccaattacgc tgtatttaa cacgatgtat gtctgttttt gtggtgctct     5220
agtggtaaat aaattatttc gatgatatgt ggatgtcttt ttcctatcag taccatcatc    5280
gagtctagaa aacacctgtg atgcaataag actatctcaa gctggaaaag tcataccacc    5340
tttccgattg ccctctgtgc tttctccctt aaggacagtc acttcagaag tcatgcttta    5400
aagcacaaga gtcaggccat atccatcaag gatagaagaa atccctgtgc cgtcttttta    5460
ttcccttatt tattgctatt tggtaattgt ttgagattta gtttccatcc agcttgactg    5520
ccgaccagaa aaaatgcaga gagatgtttg caccatgctt tggctttctg gttctatgtt    5580
ctgccaacgc cagggccaaa agaactggtc tagacagtat cccctgtagc cccataactt    5640
ggatagttgc tgagccagcc agatataaca agagccacgt gctttctggg gttggttgtt    5700
tgggatcagc tacttgcctg tcagtttcac tggtaccact gcaccacaaa caaaaaaacc    5760
caccctattt cctccaattt ttttggctgc tacctacaag accagactcc tcaaacgagt    5820
tgccaatctc ttaataaata ggattaataa aaaaagtaat tgtgactcaa aaaaaaaaaa    5880
aa                                                                  5882
```

<210> SEQ ID NO 2
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 2
gaccagatgc agga                                                     14

<210> SEQ ID NO 3
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 3
gcgaccgtga ccagat                                                   16

<210> SEQ ID NO 4
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 4
gcgcgaccgt gacc                                                     14

<210> SEQ ID NO 5
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 5

-continued agcgcgaccg tga                                      13

<210> SEQ ID NO 6
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 6
gaccgtgacc agat                                     14

<210> SEQ ID NO 7
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 7
ctgcccgcgg at 12

<210> SEQ ID NO 8
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 8
tctgcccgcg gat 13

<210> SEQ ID NO 9
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 9
ggatctgccc gcgga 15

<210> SEQ ID NO 10
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 10
cttgctcagg atctgcc 17

<210> SEQ ID NO 11
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 11
gctcaggatc tgcccgcgga 20

<210> SEQ ID NO 12
<211> LENGTH: 13
<212> TYPE: DNA

```
<213> ORGANISM: Artificial Sequence
<220> FEATURE:
<223> OTHER INFORMATION: modified TGF-beta2 oligonucleotide

<400> SEQUENCE: 12
ggatcgcctc gat                                                        13

<210> SEQ ID NO 13
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 13
ccgcggatcg cc                                                         12

<210> SEQ ID NO 14
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 14
acctccttgg cgtagta                                                    17

<210> SEQ ID NO 15
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 15
cctccttggc gtagta                                                     16

<210> SEQ ID NO 16
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 16
ctccttggcg tagta                                                      15

<210> SEQ ID NO 17
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 17
tccttggcgt agta                                                       14

<210> SEQ ID NO 18
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 18

<210> SEQ ID NO 19
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 19
aagtgggcgg gat                                                          13

<210> SEQ ID NO 20
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 20
gcgggatggc at                                                           12

<210> SEQ ID NO 21
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 21
gaaatcacct ccg                                                          13

<210> SEQ ID NO 22
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 22
aagtgggcgg gat                                                          13

<210> SEQ ID NO 23
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 23
tgtagcgctg ggt                                                          13

<210> SEQ ID NO 24
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 24
cgaaggagag cca                                                          13

<210> SEQ ID NO 25
<211> LENGTH: 14
<212> TYPE: DNA
<213> ORGANISM: Artificial Sequence
<220> FEATURE:

<223> OTHER INFORMATION: modified TGF-beta2 oligonucleotide

<400> SEQUENCE: 25
tcgcgctcgc aggc                                                       14

<210> SEQ ID NO 26
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 26
aagtgggcgg gatg                                                       14

<210> SEQ ID NO 27
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 27
atgtagcgct gggt                                                       14

<210> SEQ ID NO 28
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 28
cgaaggagag ccat                                                       14

<210> SEQ ID NO 29
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 29
gaaagtgggc gggat                                                      15

<210> SEQ ID NO 30
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 30
cgaaggagag ccatt                                                      15

<210> SEQ ID NO 31
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 31
cgatcctctt gcgcat                                                     16

```
<210> SEQ ID NO 32
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 32
aagtgggcgg gatggc                                                    16

<210> SEQ ID NO 33
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 33
gatggaaatc acctccg                                                   17

<210> SEQ ID NO 34
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 34
aaacctcctt ggcgtag                                                   17

<210> SEQ ID NO 35
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 35
tagaaagtgg gcgggat                                                   17

<210> SEQ ID NO 36
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 36
ggcgggatgg cat                                                       13

<210> SEQ ID NO 37
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 37
gggtctgtag aaagtg                                                    16

<210> SEQ ID NO 38
<211> LENGTH: 15
<212> TYPE: DNA
<213> ORGANISM: Artificial Sequence
<220> FEATURE:
<223> OTHER INFORMATION: modified TGF-beta2 oligonucleotide
```

-continued

```
<400> SEQUENCE: 38
gaaggagagc cattc                                                      15

<210> SEQ ID NO 39
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 39
ccaggttcct gtctt                                                      15

<210> SEQ ID NO 40
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 40
tctgatcacc actgg                                                      15

<210> SEQ ID NO 41
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 41
tttctgatca ccactgg                                                    17

<210> SEQ ID NO 42
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 42
gtctgtagga gggca                                                      15

<210> SEQ ID NO 43
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 43
agtctgtagg agggca                                                     16

<210> SEQ ID NO 44
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 44
tctgtaggag ggc                                                        13

<210> SEQ ID NO 45
<211> LENGTH: 17
```

```
<212> TYPE: DNA
<213> ORGANISM: Artificial Sequence
<220> FEATURE:
<223> OTHER INFORMATION: modified TGF-beta2 oligonucleotide

<400> SEQUENCE: 45
cagatgccag ttttaac                                                      17

<210> SEQ ID NO 46
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 46
caaagtattt ggtctcc                                                      17

<210> SEQ ID NO 47
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 47
ccttaagcca tccatga                                                      17

<210> SEQ ID NO 48
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 48
gtactggcca gctaa                                                        15

<210> SEQ ID NO 49
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 49
gcctcgatcc tcttgcgcat                                                   20

<210> SEQ ID NO 50
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 50
aaacctcctt ggcgtagtac                                                   20

<210> SEQ ID NO 51
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 51
```
gaaagtgggc gggatggcat                                                    20

<210> SEQ ID NO 52
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 52
gaattgctcg cttaggg                                                       17

<210> SEQ ID NO 53
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 53
cgtcgcggtt gcgttca                                                       17

<210> SEQ ID NO 54
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 54
cgtggcctac accctgg                                                       17

<210> SEQ ID NO 55
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 55
ttctaaagca ataggcc                                                       17

<210> SEQ ID NO 56
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 56
agaatggtta gaggttc                                                       17

<210> SEQ ID NO 57
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 57
tctgaactag taccgcc                                                       17

<210> SEQ ID NO 58
<211> LENGTH: 17
<212> TYPE: DNA
<213> ORGANISM: Artificial Sequence

```
<220> FEATURE:
<223> OTHER INFORMATION: modified TGF-beta2 oligonucleotide

<400> SEQUENCE: 58
cccattaata tgacctc                                                17

<210> SEQ ID NO 59
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 59
tttagttaga accctaa                                                17

<210> SEQ ID NO 60
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 60
cctcagatat agataac                                                17

<210> SEQ ID NO 61
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 61
tactattatg gcatccc                                                17

<210> SEQ ID NO 62
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 62
tgcccacttg catacta                                                17

<210> SEQ ID NO 63
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 63
agcgtaattg gtcatca                                                17

<210> SEQ ID NO 64
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 64
cgttggcaga acataga                                                17
```

<210> SEQ ID NO 65
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 65
gggatactgt ctagacc                                                17

<210> SEQ ID NO 66
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 66
attggcaact cgtttga                                                17

<210> SEQ ID NO 67
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 67
cgtcaggcta atattc                                                 16

<210> SEQ ID NO 68
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 68
ggatgactcc ctagac                                                 16

<210> SEQ ID NO 69
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 69
gtcgcggttg cgttca                                                 16

<210> SEQ ID NO 70
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 70
ctcggtactc ggtcgg                                                 16

<210> SEQ ID NO 71
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 71
ggttcggtcc tgcctt                          16

<210> SEQ ID NO 72
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 72
aataggccgc atccaa                          16

<210> SEQ ID NO 73
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 73
aactagtacc gcctt                           16

<210> SEQ ID NO 74
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 74
tcggtcatat aataac                          16

<210> SEQ ID NO 75
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 75
agaccgtcag gctaa                           15

<210> SEQ ID NO 76
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 76
gtcgcggttg cgttc                           15

<210> SEQ ID NO 77
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 77
ttccactgcg gcgct                           15

<210> SEQ ID NO 78

```
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 78
aaggagcggt tcggt                                                      15

<210> SEQ ID NO 79
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 79
ctcgggtgcg gagtg                                                      15

<210> SEQ ID NO 80
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 80
ctgactttgg cgagt                                                      15

<210> SEQ ID NO 81
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 81
gataggaacg gtacg                                                      15

<210> SEQ ID NO 82
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 82
cactttggat tcccg                                                      15

<210> SEQ ID NO 83
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 83
gtcgcggttg cgtt                                                       14

<210> SEQ ID NO 84
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 84
```

-continued tacaccctgg cggg                                            14

<210> SEQ ID NO 85
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 85
ctcggtactc ggtc                                            14

<210> SEQ ID NO 86
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 86
aggagcggtt cggt                                            14

<210> SEQ ID NO 87
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 87
gtctcgggtg cgga                                            14

<210> SEQ ID NO 88
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 88
tacgggacgg gcag                                            14

<210> SEQ ID NO 89
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 89
cgtcgctcct ctcg                                            14

<210> SEQ ID NO 90
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 90
tagcgctggg ttgg                                            14

<210> SEQ ID NO 91
<211> LENGTH: 14
<212> TYPE: DNA

```
<213> ORGANISM: Artificial Sequence
<220> FEATURE:
<223> OTHER INFORMATION: modified TGF-beta2 oligonucleotide
<400> SEQUENCE: 91
aagcaatagg ccgc 14

<210> SEQ ID NO 92
<211> LENGTH: 14
<212> TYPE: DNA
<213> ORGANISM: Artificial Sequence
<220> FEATURE:
<223> OTHER INFORMATION: modified TGF-beta2 oligonucleotide
<400> SEQUENCE: 92
tacgggcatg ctcc 14

<210> SEQ ID NO 93
<211> LENGTH: 14
<212> TYPE: DNA
<213> ORGANISM: Artificial Sequence
<220> FEATURE:
<223> OTHER INFORMATION: modified TGF-beta2 oligonucleotide
<400> SEQUENCE: 93
aggcgcggga tagg 14

<210> SEQ ID NO 94
<211> LENGTH: 14
<212> TYPE: DNA
<213> ORGANISM: Artificial Sequence
<220> FEATURE:
<223> OTHER INFORMATION: modified TGF-beta2 oligonucleotide
<400> SEQUENCE: 94
tttggattcc cgcc 14

<210> SEQ ID NO 95
<211> LENGTH: 14
<212> TYPE: DNA
<213> ORGANISM: Artificial Sequence
<220> FEATURE:
<223> OTHER INFORMATION: modified TGF-beta2 oligonucleotide
<400> SEQUENCE: 95
accactagag cacc 14

<210> SEQ ID NO 96
<211> LENGTH: 14
<212> TYPE: DNA
<213> ORGANISM: Artificial Sequence
<220> FEATURE:
<223> OTHER INFORMATION: modified TGF-beta2 oligonucleotide
<400> SEQUENCE: 96
gcgttggcag aaca 14

<210> SEQ ID NO 97
<211> LENGTH: 13
<212> TYPE: DNA
<213> ORGANISM: Artificial Sequence
<220> FEATURE:
<223> OTHER INFORMATION: modified TGF-beta2 oligonucleotide
<400> SEQUENCE: 97
ttgctcgctt agg 13

<210> SEQ ID NO 98
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 98
gtcgcggttg cgt                                                    13

<210> SEQ ID NO 99
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 99
ggcgctcggt act                                                    13

<210> SEQ ID NO 100
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 100
atctgaactc ggc                                                    13

<210> SEQ ID NO 101
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 101
cggttggtct gtt                                                    13

<210> SEQ ID NO 102
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 102
tccaccctag atc                                                    13

<210> SEQ ID NO 103
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 103
ctagtaccgc ctt                                                    13

<210> SEQ ID NO 104
<211> LENGTH: 13
<212> TYPE: DNA
<213> ORGANISM: Artificial Sequence
<220> FEATURE:

<223> OTHER INFORMATION: modified TGF-beta2 oligonucleotide

<400> SEQUENCE: 104
ggtcggcagt caa                                                        13

<210> SEQ ID NO 105
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 105
cttgcgacac cc                                                         12

<210> SEQ ID NO 106
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 106
gagcggttcg gt                                                         12

<210> SEQ ID NO 107
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 107
acacagtagt gcat                                                       14

<210> SEQ ID NO 108
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 108
gggtctgtag aaag                                                       14

<210> SEQ ID NO 109
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 109
ggttggagat gtta                                                       14

<210> SEQ ID NO 110
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 110
tgggttggag atgt                                                       14

```
<210> SEQ ID NO 111
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 111
gctgggttgg agat                                                        14

<210> SEQ ID NO 112
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 112
gcgctgggtt ggag                                                        14

<210> SEQ ID NO 113
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 113
agcgctgggt tgga                                                        14

<210> SEQ ID NO 114
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 114
tagcgctggg ttgg                                                        14

<210> SEQ ID NO 115
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 115
gtagcgctgg gttg                                                        14

<210> SEQ ID NO 116
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 116
gatgtagcgc tggg                                                        14

<210> SEQ ID NO 117
<211> LENGTH: 14
<212> TYPE: DNA
<213> ORGANISM: Artificial Sequence
<220> FEATURE:
<223> OTHER INFORMATION: modified TGF-beta2 oligonucleotide
```

```
<400> SEQUENCE: 117
ccattcgcct tctg                                                  14

<210> SEQ ID NO 118
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 118
gagagccatt cgcc                                                  14

<210> SEQ ID NO 119
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 119
agcagggaca gtgt                                                  14

<210> SEQ ID NO 120
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 120
gcaggagatg tggg                                                  14

<210> SEQ ID NO 121
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 121
cggttggtct gttg                                                  14

<210> SEQ ID NO 122
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 122
ccggttggtc tgtt                                                  14

<210> SEQ ID NO 123
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 123
gccggttggt ctgt                                                  14

<210> SEQ ID NO 124
<211> LENGTH: 14
```

-continued

```
<212> TYPE: DNA
<213> ORGANISM: Artificial Sequence
<220> FEATURE:
<223> OTHER INFORMATION: modified TGF-beta2 oligonucleotide

<400> SEQUENCE: 124
agttggcatt gtac                                                            14

<210> SEQ ID NO 125
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 125
ggttagaggt tcta                                                            14

<210> SEQ ID NO 126
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 126
atggttagag gttc                                                            14

<210> SEQ ID NO 127
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 127
agaatggtta gagg                                                            14

<210> SEQ ID NO 128
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 128
agagaatggt taga                                                            14

<210> SEQ ID NO 129
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 129
cgttgtcgtc gtca                                                            14

<210> SEQ ID NO 130
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 130
```
accaaggctc tctt                                                         14

<210> SEQ ID NO 131
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 131
gcttcttgtc tctc                                                         14

<210> SEQ ID NO 132
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 132
ggaacggtac gtac                                                         14

<210> SEQ ID NO 133
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 133
taggaacggt acgt                                                         14

<210> SEQ ID NO 134
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 134
gggataggaa cggt                                                         14

<210> SEQ ID NO 135
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 135
cgcgggatag gaac                                                         14

<210> SEQ ID NO 136
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 136
aggcgcggga tagg                                                         14

<210> SEQ ID NO 137
<211> LENGTH: 14
<212> TYPE: DNA
<213> ORGANISM: Artificial Sequence

```
<220> FEATURE:
<223> OTHER INFORMATION: modified TGF-beta2 oligonucleotide

<400> SEQUENCE: 137
gtcaagctgg atgg                                                              14

<210> SEQ ID NO 138
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 138
tctgtaggag ggc                                                               13

<210> SEQ ID NO 139
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 139
gaccagatgc agga                                                              14

<210> SEQ ID NO 140
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 140
ctccttggcg tagta                                                             15

<210> SEQ ID NO 141
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 141
cctccttggc gtagta                                                            16

<210> SEQ ID NO 142
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 142
cagatgccag ttttaac                                                           17

<210> SEQ ID NO 143
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 143
agcgtaattg gtcatca                                                           17
```

<210> SEQ ID NO 144
<211> LENGTH: 17
<212> TYPE: DNA
<213> ORGANISM: Artificial Sequence
<220> FEATURE:
<223> OTHER INFORMATION: fake sequence

<400> SEQUENCE: 144
aaaaaaaaaa aaaaaaa                                                  17

<210> SEQ ID NO 145
<211> LENGTH: 18
<212> TYPE: DNA
<213> ORGANISM: Artificial Sequence
<220> FEATURE:
<223> OTHER INFORMATION: fake sequence

<400> SEQUENCE: 145
aaaaaaaaaa aaaaaaaa                                                 18

<210> SEQ ID NO 146
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 146
agtatttggt ctcc                                                     14

<210> SEQ ID NO 147
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 147
aagtatttgg tctc                                                     14

<210> SEQ ID NO 148
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 148
caaagtattt ggtctcc                                                  17

<210> SEQ ID NO 149
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 149
aagtatttgg tctcc                                                    15

<210> SEQ ID NO 150
<211> LENGTH: 17
<212> TYPE: DNA
<213> ORGANISM: Artificial Sequence
<220> FEATURE:
<223> OTHER INFORMATION: modified TGF-beta1 oligonucleotide

```
<400> SEQUENCE: 150
agctcgtccc tcctccc                                                    17

<210> SEQ ID NO 151
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 151
gagggctggt ccggaat                                                    17

<210> SEQ ID NO 152
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 152
cgagggctgg tccggaa                                                    17

<210> SEQ ID NO 153
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 153
gagggcggca tggggga                                                    17

<210> SEQ ID NO 154
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 154
gcgggtgctg ttgtaca                                                    17

<210> SEQ ID NO 155
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 155
cgcgggtgct gttgtac                                                    17

<210> SEQ ID NO 156
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 156
gtcgcgggtg ctgttgt                                                    17

<210> SEQ ID NO 157
```

```
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 157
ggtcgcgggt gctgttg                                                    17

<210> SEQ ID NO 158
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 158
ccggtcgcgg gtgctgt                                                    17

<210> SEQ ID NO 159
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 159
cccggtcgcg ggtgctg                                                    17

<210> SEQ ID NO 160
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 160
agcacgcggg tgacctc                                                    17

<210> SEQ ID NO 161
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 161
ttagcacgcg ggtgacc                                                    17

<210> SEQ ID NO 162
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 162
gggctcgtgg atccact                                                    17

<210> SEQ ID NO 163
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 163
```
ccttgggctc gtggatc                                                17

<210> SEQ ID NO 164
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 164
tggcatggta gcccttg                                                17

<210> SEQ ID NO 165
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 165
cgagggctgg tccgga                                                 16

<210> SEQ ID NO 166
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 166
gcgggtgctg ttgtac                                                 16

<210> SEQ ID NO 167
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 167
gcacgcgggt gacctc                                                 16

<210> SEQ ID NO 168
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 168
ccttgggctc gtggat                                                 16

<210> SEQ ID NO 169
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 169
ggcatggtag cccttg                                                 16

<210> SEQ ID NO 170
<211> LENGTH: 14
<212> TYPE: DNA

```
<213> ORGANISM: Artificial Sequence
<220> FEATURE:
<223> OTHER INFORMATION: modified TGF-beta1 oligonucleotide

<400> SEQUENCE: 170
gggtgctgtt gtac                                                    14

<210> SEQ ID NO 171
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 171
tcgcgggtgc tgtt                                                    14

<210> SEQ ID NO 172
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 172
gtcgcgggtg ctgt                                                    14

<210> SEQ ID NO 173
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 173
ctcgtggatc cact                                                    14

<210> SEQ ID NO 174
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 174
atggtagccc ttgg                                                    14

<210> SEQ ID NO 175
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 175
tggcatggta gccc                                                    14

<210> SEQ ID NO 176
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 176
gaagttggca tggt                                                    14
```

-continued

<210> SEQ ID NO 177
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 177
tcgcgggtgc tgt                                                    13

<210> SEQ ID NO 178
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 178
cacccggtcg cgg                                                    13

<210> SEQ ID NO 179
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 179
ccacccggtc gcg                                                    13

<210> SEQ ID NO 180
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 180
cgccaggaat tgt                                                    13

<210> SEQ ID NO 181
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 181
ggctcgtgga tcc                                                    13

<210> SEQ ID NO 182
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 182
tgggctcgtg gat                                                    13

<210> SEQ ID NO 183
<211> LENGTH: 13
<212> TYPE: DNA
<213> ORGANISM: Artificial Sequence
<220> FEATURE:

```
<223> OTHER INFORMATION: modified TGF-beta1 oligonucleotide

<400> SEQUENCE: 183
gcatggtagc cct                                                          13

<210> SEQ ID NO 184
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 184
agttggcatg gta                                                          13

<210> SEQ ID NO 185
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 185
ttgcaggagc gca                                                          13

<210> SEQ ID NO 186
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 186
attagcacgc gggtgac                                                      17

<210> SEQ ID NO 187
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 187
accattagca cgcgggt                                                      17

<210> SEQ ID NO 188
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 188
caccattagc acgcggg                                                      17

<210> SEQ ID NO 189
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 189
ccaccattag cacgcgg                                                      17
```

```
<210> SEQ ID NO 190
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 190
tccaccatta gcacgcg                                                    17

<210> SEQ ID NO 191
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 191
tccaccttgg gcttgcg                                                    17

<210> SEQ ID NO 192
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 192
ttagcacgcg ggtgac                                                     16

<210> SEQ ID NO 193
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 193
accattagca cgcggg                                                     16

<210> SEQ ID NO 194
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 194
caccattagc acgcgg                                                     16

<210> SEQ ID NO 195
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 195
caccattagc acgcg                                                      15

<210> SEQ ID NO 196
<211> LENGTH: 15
<212> TYPE: DNA
<213> ORGANISM: Artificial Sequence
<220> FEATURE:
<223> OTHER INFORMATION: modified TGF-beta1 oligonucleotide
```

```
<400> SEQUENCE: 196
gcggcacgca gcacg                                                    15

<210> SEQ ID NO 197
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 197
tcgatgcgct tccg                                                     14

<210> SEQ ID NO 198
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 198
tagcacgcgg gtga                                                     14

<210> SEQ ID NO 199
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 199
attagcacgc gggt                                                     14

<210> SEQ ID NO 200
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 200
cattagcacg cggg                                                     14

<210> SEQ ID NO 201
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 201
accattagca cgcg                                                     14

<210> SEQ ID NO 202
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 202
caccattagc acgc                                                     14

<210> SEQ ID NO 203
<211> LENGTH: 14
```

-continued

<210> SEQ ID NO 203
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 203
ccaccattag cacg                                                        14

<210> SEQ ID NO 204
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 204
tccaccatta gcac                                                        14

<210> SEQ ID NO 205
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 205
gaccttgctg tact                                                        14

<210> SEQ ID NO 206
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 206
ggaccttgct gtac                                                        14

<210> SEQ ID NO 207
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 207
aggaccttgc tgta                                                        14

<210> SEQ ID NO 208
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 208
cggcacgcag cacg                                                        14

<210> SEQ ID NO 209
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 209
accttgggct tgcg                                                14

<210> SEQ ID NO 210
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 210
ttagcacgcg ggt                                                 13

<210> SEQ ID NO 211
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 211
accattagca cgc                                                 13

<210> SEQ ID NO 212
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 212
cggcacgcag cac                                                 13

<210> SEQ ID NO 213
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 213
caccagctcc atgtcga                                             17

<210> SEQ ID NO 214
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 214
tcgcgggtgc tgttgta                                             17

<210> SEQ ID NO 215
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 215
gtgtccaggc tccaaat                                             17

<210> SEQ ID NO 216
<211> LENGTH: 16
<212> TYPE: DNA
<213> ORGANISM: Artificial Sequence

```
<220> FEATURE:
<223> OTHER INFORMATION: modified TGF-beta1 oligonucleotide

<400> SEQUENCE: 216
gctcgtccct cctccc                                                   16

<210> SEQ ID NO 217
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 217
accagctcgt ccctcc                                                   16

<210> SEQ ID NO 218
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 218
ggaggccccg cccctg                                                   16

<210> SEQ ID NO 219
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 219
catgggggag gcggcg                                                   16

<210> SEQ ID NO 220
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 220
accagctcca tgtcga                                                   16

<210> SEQ ID NO 221
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 221
ggtcgcgggt gctgtt                                                   16

<210> SEQ ID NO 222
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 222
ggaccttgct gtactg                                                   16
```

<210> SEQ ID NO 223
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 223
tccaccttgg gcttgc					16

<210> SEQ ID NO 224
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 224
agctcgtccc tcctc					15

<210> SEQ ID NO 225
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 225
ccagctcgtc cctcc					15

<210> SEQ ID NO 226
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 226
gagggctggt ccgga					15

<210> SEQ ID NO 227
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 227
tcccgagggc tggtc					15

<210> SEQ ID NO 228
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 228
cggcatgggg gaggc					15

<210> SEQ ID NO 229
<211> LENGTH: 15
<212> TYPE: DNA
<213> ORGANISM: Artificial Sequence
<220> FEATURE:
<223> OTHER INFORMATION: modified TGF-beta1 oligonucleotide -continued

<400> SEQUENCE: 229
cagctccatg tcgat                                                    15

<210> SEQ ID NO 230
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 230
accagctcca tgtcg                                                    15

<210> SEQ ID NO 231
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 231
tcgcgggtgc tgttg                                                    15

<210> SEQ ID NO 232
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 232
gtcgcgggtg ctgtt                                                    15

<210> SEQ ID NO 233
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 233
ggtcgcgggt gctgt                                                    15

<210> SEQ ID NO 234
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 234
agcacgcggg tgacc                                                    15

<210> SEQ ID NO 235
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 235
tagcacgcgg gtgac                                                    15

<210> SEQ ID NO 236

```
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 236
cattagcacg cgggt                                                    15

<210> SEQ ID NO 237
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 237
tccaccatta gcacg                                                    15

<210> SEQ ID NO 238
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 238
ccaggaattg ttgct                                                    15

<210> SEQ ID NO 239
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 239
ttgggctcgt ggatc                                                    15

<210> SEQ ID NO 240
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 240
cttgggctcg tggat                                                    15

<210> SEQ ID NO 241
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 241
ttggcatggt agccc                                                    15

<210> SEQ ID NO 242
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 242
```

```
gaagttggca tggta                                                    15

<210> SEQ ID NO 243
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 243
agaagttggc atggt                                                    15

<210> SEQ ID NO 244
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 244
tgtccaggct ccaaa                                                    15

<210> SEQ ID NO 245
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 245
aggaccttgc tgtac                                                    15

<210> SEQ ID NO 246
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 246
caccttgggc ttgcg                                                    15

<210> SEQ ID NO 247
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 247
agctcgtccc tcct                                                     14

<210> SEQ ID NO 248
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 248
cagctcgtcc ctcc                                                     14

<210> SEQ ID NO 249
<211> LENGTH: 14
<212> TYPE: DNA
```

```
<213> ORGANISM: Artificial Sequence
<220> FEATURE:
<223> OTHER INFORMATION: modified TGF-beta1 oligonucleotide

<400> SEQUENCE: 249
accagctcgt ccct                                                 14

<210> SEQ ID NO 250
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 250
cccgagggct ggtc                                                 14

<210> SEQ ID NO 251
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 251
gcggcatggg ggag                                                 14

<210> SEQ ID NO 252
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 252
gtcttgcagg tgga                                                 14

<210> SEQ ID NO 253
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 253
tcgatgcgct tccg                                                 14

<210> SEQ ID NO 254
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 254
ggacaggatc tggc                                                 14

<210> SEQ ID NO 255
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 255 acctcccct ggct                                                  14
```

```
<210> SEQ ID NO 256
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 256
accattagca cgcg                                                         14

<210> SEQ ID NO 257
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 257
cagcagttct tctc                                                         14

<210> SEQ ID NO 258
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 258
tacagctgcc gcac                                                         14

<210> SEQ ID NO 259
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 259
agttggcatg gtag                                                         14

<210> SEQ ID NO 260
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 260
aagttggcat ggta                                                         14

<210> SEQ ID NO 261
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 261
gaagttggca tggt                                                         14

<210> SEQ ID NO 262
<211> LENGTH: 14
<212> TYPE: DNA
<213> ORGANISM: Artificial Sequence
<220> FEATURE:
```

<223> OTHER INFORMATION: modified TGF-beta1 oligonucleotide

<400> SEQUENCE: 262
tccaggctcc aaat				14

<210> SEQ ID NO 263
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 263
accttgctgt actg				14

<210> SEQ ID NO 264
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 264
ttgcaggagc gcac				14

<210> SEQ ID NO 265
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 265
gcagaagttg gcat				14

<210> SEQ ID NO 266
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 266
cgggtgctgt tgta				14

<210> SEQ ID NO 267
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 267
cccagcggca acggaaa			17

<210> SEQ ID NO 268
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 268
caagaggtcc ccgcgcc			17

```
<210> SEQ ID NO 269
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 269
gcgtccccgg cggcaaa                                                  17

<210> SEQ ID NO 270
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 270
ggtcggcgac tcccgag                                                  17

<210> SEQ ID NO 271
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 271
tcggagagag atccgtc                                                  17

<210> SEQ ID NO 272
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 272
atcccacgga aataacc                                                  17

<210> SEQ ID NO 273
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 273
ctcagtatcc cacggaa                                                  17

<210> SEQ ID NO 274
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 274
actgccgaga gcgcgaa                                                  17

<210> SEQ ID NO 275
<211> LENGTH: 17
<212> TYPE: DNA
<213> ORGANISM: Artificial Sequence
<220> FEATURE:
<223> OTHER INFORMATION: modified TGF-beta oligonucleotide
```

```
<400> SEQUENCE: 275
ctgatgtgtt gaagaac                                                  17

<210> SEQ ID NO 276
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 276
tgaggtatcg ccaggaa                                                  17

<210> SEQ ID NO 277
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 277
actgccgcac aactccg                                                  17

<210> SEQ ID NO 278
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 278
cggcccacgt agtacac                                                  17

<210> SEQ ID NO 279
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 279
cccagcggca acggaa                                                   16

<210> SEQ ID NO 280
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 280
tcgcgccaag aggtcc                                                   16

<210> SEQ ID NO 281
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 281
ggtcggcgac tcccga                                                   16

<210> SEQ ID NO 282
<211> LENGTH: 16
```

```
<212> TYPE: DNA
<213> ORGANISM: Artificial Sequence
<220> FEATURE:
<223> OTHER INFORMATION: modified TGF-beta oligonucleotide

<400> SEQUENCE: 282
gtcggagaga gatccg                                                    16

<210> SEQ ID NO 283
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 283
tcagtatccc acggaa                                                    16

<210> SEQ ID NO 284
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 284
cgagagcgcg aacagg                                                    16

<210> SEQ ID NO 285
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 285
actgccgaga gcgcga                                                    16

<210> SEQ ID NO 286
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 286
ggcgtcagca ccagta                                                    16

<210> SEQ ID NO 287
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 287
ggtttccacc attagc                                                    16

<210> SEQ ID NO 288
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 288
```

```
gaggtatcgc caggaa                                                     16

<210> SEQ ID NO 289
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 289
aaccactgcc gcacaa                                                     16

<210> SEQ ID NO 290
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 290
cggcccacgt agtaca                                                     16

<210> SEQ ID NO 291
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 291
cggcggctcg tctca                                                      15

<210> SEQ ID NO 292
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 292
cccagcggca acgga                                                      15

<210> SEQ ID NO 293
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 293
tcgcgccaag aggtc                                                      15

<210> SEQ ID NO 294
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 294
cgtcgcgcca agagg                                                      15

<210> SEQ ID NO 295
<211> LENGTH: 15
<212> TYPE: DNA
<213> ORGANISM: Artificial Sequence
```

```
<220> FEATURE:
<223> OTHER INFORMATION: modified TGF-beta oligonucleotide

<400> SEQUENCE: 295
ggagcaagcg tcccc                                                           15

<210> SEQ ID NO 296
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 296
gtgcgcccga ggtct                                                           15

<210> SEQ ID NO 297
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 297
gtctaggatg cgcgg                                                           15

<210> SEQ ID NO 298
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 298
cagtatccca cggaa                                                           15

<210> SEQ ID NO 299
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 299
ccgagagcgc gaaca                                                           15

<210> SEQ ID NO 300
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 300
ggcgtcagca ccagt                                                           15

<210> SEQ ID NO 301
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 301
gttgctgagg tatcg                                                           15
```

```
<210> SEQ ID NO 302
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 302
accactgccg cacaa                                                          15

<210> SEQ ID NO 303
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 303
cggcccacgt agtac                                                          15

<210> SEQ ID NO 304
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 304
ctcggcgact cctt                                                           14

<210> SEQ ID NO 305
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 305
agcggcaacg gaaa                                                           14

<210> SEQ ID NO 306
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 306
tcgcgccaag aggt                                                           14

<210> SEQ ID NO 307
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 307
tccccggcgg caaa                                                           14

<210> SEQ ID NO 308
<211> LENGTH: 14
<212> TYPE: DNA
<213> ORGANISM: Artificial Sequence
<220> FEATURE:
<223> OTHER INFORMATION: modified TGF-beta oligonucleotide
```

```
<400> SEQUENCE: 308
tgcgcccgag gtct                                                    14

<210> SEQ ID NO 309
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 309
gtctaggatg cgcg                                                    14

<210> SEQ ID NO 310
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 310
ggtcggagag agat                                                    14

<210> SEQ ID NO 311
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 311
cacggaaata acct                                                    14

<210> SEQ ID NO 312
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 312
agagcgcgaa cagg                                                    14

<210> SEQ ID NO 313
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 313
atagtcccgc ggcc                                                    14

<210> SEQ ID NO 314
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 314
tagtagtcgg cctc                                                    14

<210> SEQ ID NO 315
```

```
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 315
atagatttcg ttgt                                                    14

<210> SEQ ID NO 316
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 316
gaggtatcgc cagg                                                    14

<210> SEQ ID NO 317
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 317
gccgcacaac tccg                                                    14

<210> SEQ ID NO 318
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 318
tcgcgccaag agg                                                     13

<210> SEQ ID NO 319
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 319
aagcgtcccc ggc                                                     13

<210> SEQ ID NO 320
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 320
gacgccgtgt agg                                                     13

<210> SEQ ID NO 321
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 321
```

-continued gtcggcgact ccc                                             13

<210> SEQ ID NO 322
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 322
tgcgcccgag gtc                                             13

<210> SEQ ID NO 323
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 323
gtcggagaga gat                                             13

<210> SEQ ID NO 324
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 324
tcccacggaa ata                                             13

<210> SEQ ID NO 325
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 325
tgccgagagc gcg                                             13

<210> SEQ ID NO 326
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 326
tagtcccgcg gcc                                             13

<210> SEQ ID NO 327
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 327
tagtagtcgg cct                                             13

<210> SEQ ID NO 328
<211> LENGTH: 13
<212> TYPE: DNA

```
<213> ORGANISM: Artificial Sequence
<220> FEATURE:
<223> OTHER INFORMATION: modified TGF-beta oligonucleotide

<400> SEQUENCE: 328
catagatttc gtt                                                         13

<210> SEQ ID NO 329
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 329
tttaacttga gcc                                                         13

<210> SEQ ID NO 330
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 330
gaggtatcgc cag                                                         13

<210> SEQ ID NO 331
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 331
actccggtga cat                                                         13

<210> SEQ ID NO 332
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 332
gcccacgtag tac                                                         13

<210> SEQ ID NO 333
<211> LENGTH: 12
<212> TYPE: DNA
<213> ORGANISM: Artificial Sequence
<220> FEATURE:
<223> OTHER INFORMATION: modified TGF-beta oligonucleotide

<400> SEQUENCE: 333
tcggcgactc cc                                                          12

<210> SEQ ID NO 334
<211> LENGTH: 12
<212> TYPE: DNA
<213> ORGANISM: Artificial Sequence
<220> FEATURE:
<223> OTHER INFORMATION: modified TGF-beta oligonucleotide

<400> SEQUENCE: 334
gtcggcgact cc                                                          12
```

```
<210> SEQ ID NO 335
<211> LENGTH: 14
<212> TYPE: DNA
<213> ORGANISM: Artificial Sequence
<220> FEATURE:
<223> OTHER INFORMATION: fake sequence

<400> SEQUENCE: 335
aaaaaaaaaa aaaa                                                        14

<210> SEQ ID NO 336
<211> LENGTH: 16
<212> TYPE: DNA
<213> ORGANISM: Artificial Sequence
<220> FEATURE:
<223> OTHER INFORMATION: fake sequence

<400> SEQUENCE: 336
aaaaaaaaaa aaaaaa                                                      16

<210> SEQ ID NO 337
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 337
caggaagcgc tggcaac                                                     17

<210> SEQ ID NO 338
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 338
ggtgcatgaa ctcactg                                                     17

<210> SEQ ID NO 339
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 339
gtcccctaat ggcttcc                                                     17

<210> SEQ ID NO 340
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 340
atctgtcccc taatggc                                                     17

<210> SEQ ID NO 341
<211> LENGTH: 17
<212> TYPE: DNA
<213> ORGANISM: Artificial Sequence
<220> FEATURE:
```

<223> OTHER INFORMATION: modified TGF-beta3 oligonucleotide

<400> SEQUENCE: 341
ccgggtgctg ttgtaaa                                              17

<210> SEQ ID NO 342
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 342
cctggatcat gtcgaat                                              17

<210> SEQ ID NO 343
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 343
ccctggatca tgtcgaa                                              17

<210> SEQ ID NO 344
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 344
gtagcacctg cttccag                                              17

<210> SEQ ID NO 345
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 345
gggctttcta aatgac                                               16

<210> SEQ ID NO 346
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 346
tgactcccag caggcc                                               16

<210> SEQ ID NO 347
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 347
gtgcatgaac tcactg                                               16

-continued

<210> SEQ ID NO 348
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 348
ggtgcatgaa ctcact                                                   16

<210> SEQ ID NO 349
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 349
atctgtcccc taatgg                                                   16

<210> SEQ ID NO 350
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 350
cgggtgctgt tgtaaa                                                   16

<210> SEQ ID NO 351
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 351
ccgggtgctg ttgtaa                                                   16

<210> SEQ ID NO 352
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 352
cctggatcat gtcgaa                                                   16

<210> SEQ ID NO 353
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 353
ccctggatca tgtcga                                                   16

<210> SEQ ID NO 354
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 354
tttgaatttg atttcc                                                         16

<210> SEQ ID NO 355
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 355
gggcctgagc agaagt                                                         16

<210> SEQ ID NO 356
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 356
gggggctttc taaat                                                          15

<210> SEQ ID NO 357
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 357
tttgtttaca cttcc                                                          15

<210> SEQ ID NO 358
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 358
ccagctaaag gtggg                                                          15

<210> SEQ ID NO 359
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 359
atggctgggt cccaa                                                          15

<210> SEQ ID NO 360
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 360 gagttttcc ttagg                                                           15

<210> SEQ ID NO 361
<211> LENGTH: 15

```
<212> TYPE: DNA
<213> ORGANISM: Artificial Sequence
<220> FEATURE:
<223> OTHER INFORMATION: modified TGF-beta3 oligonucleotide

<400> SEQUENCE: 361
aggggtggca aggca                                                    15

<210> SEQ ID NO 362
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 362
tgactcccag caggc                                                    15

<210> SEQ ID NO 363
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 363
gaagcgctgg caacc                                                    15

<210> SEQ ID NO 364
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 364
gtgcatgaac tcact                                                    15

<210> SEQ ID NO 365
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 365
gtggtgcaag tggac                                                    15

<210> SEQ ID NO 366
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 366
ctaatggctt ccacc                                                    15

<210> SEQ ID NO 367
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 367
```
cccctaatgg cttcc                                               15

<210> SEQ ID NO 368
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 368
atctgtcccc taatg                                               15

<210> SEQ ID NO 369
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 369
gatctgtccc ctaat                                               15

<210> SEQ ID NO 370
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 370
agatctgtcc cctaa                                               15

<210> SEQ ID NO 371
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 371
ggtgctgttg taaag                                               15

<210> SEQ ID NO 372
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 372
ccgggtgctg ttgta                                               15

<210> SEQ ID NO 373
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 373
gatcatgtcg aattt                                               15

<210> SEQ ID NO 374
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 374
cctggatcat gtcga                                                    15

<210> SEQ ID NO 375
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 375
ccctggatca tgtcg                                                    15

<210> SEQ ID NO 376
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 376
gatttccatc acctc                                                    15

<210> SEQ ID NO 377
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 377
ttgaatttga tttcc                                                    15

<210> SEQ ID NO 378
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 378
agcagttctc ctcca                                                    15

<210> SEQ ID NO 379
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 379
gcctgagcag aagtt                                                    15

<210> SEQ ID NO 380
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 380
gggcaagggc ctgag                                                    15

<210> SEQ ID NO 381
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 381
cccacacttt cttta                                                    15

<210> SEQ ID NO 382
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 382
tagcacctgc ttcca                                                    15

<210> SEQ ID NO 383
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 383
cgggggcttt ctaa                                                     14

<210> SEQ ID NO 384
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 384
ccattcatgc tttc                                                     14

<210> SEQ ID NO 385
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 385
aagcgctggc aacc                                                     14

<210> SEQ ID NO 386
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 386
accagagccc tttg                                                     14

<210> SEQ ID NO 387
<211> LENGTH: 14
<212> TYPE: DNA
<213> ORGANISM: Artificial Sequence
<220> FEATURE:
<223> OTHER INFORMATION: modified TGF-beta3 oligonucleotide -continued

<400> SEQUENCE: 387
cccctaatgg cttc                                                          14

<210> SEQ ID NO 388
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 388
gtcccctaat ggct                                                          14

<210> SEQ ID NO 389
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 389
atctgcccct aat                                                           13

<210> SEQ ID NO 390
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 390
agatctgtcc ccta                                                          14

<210> SEQ ID NO 391
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 391
cgggtgctgt tgta                                                          14

<210> SEQ ID NO 392
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 392
atcatgtcga attt                                                          14

<210> SEQ ID NO 393
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 393
ccctggatca tgtc                                                          14

<210> SEQ ID NO 394

```
<210> SEQ ID NO 394
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 394
cctttgaatt tgat                                                    14

<210> SEQ ID NO 395
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 395
ttgcggaagc agta                                                    14

<210> SEQ ID NO 396
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 396
gcctgagcag aagt                                                    14

<210> SEQ ID NO 397
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 397
gggggctttc taa                                                     13

<210> SEQ ID NO 398
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 398
agcgctggca acc                                                     13

<210> SEQ ID NO 399
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 399
cccctaatgg ctt                                                     13

<210> SEQ ID NO 400
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 400
```

```
tccctaatg gct                                                    13

<210> SEQ ID NO 401
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 401
tcatgtcgaa ttt                                                   13

<210> SEQ ID NO 402
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 402
atcatgtcga att                                                   13
```